United States Patent
Donahoe et al.

(10) Patent No.: US 9,791,449 B2
(45) Date of Patent: Oct. 17, 2017

(54) OVARIAN CANCER STEM CELLS AND METHODS OF ISOLATION AND USES THEREOF

(75) Inventors: Patricia K. Donahoe, Boston, MA (US); David T. MacLaughlin, Gloucester, MA (US); Jose Teixeira, Boston, MA (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 174 days.

(21) Appl. No.: 14/123,551

(22) PCT Filed: Jun. 1, 2012

(86) PCT No.: PCT/US2012/040489
§ 371 (c)(1),
(2), (4) Date: Feb. 24, 2014

(87) PCT Pub. No.: WO2012/167101
PCT Pub. Date: Dec. 6, 2012

(65) Prior Publication Data
US 2014/0194366 A1 Jul. 10, 2014

Related U.S. Application Data

(60) Provisional application No. 61/493,081, filed on Jun. 3, 2011.

(51) Int. Cl.
*G01N 33/574* (2006.01)
*A61K 31/416* (2006.01)
*G01N 33/50* (2006.01)

(52) U.S. Cl.
CPC ..... *G01N 33/57449* (2013.01); *A61K 31/416* (2013.01); *G01N 33/5073* (2013.01); *G01N 2333/70585* (2013.01); *G01N 2333/70596* (2013.01); *G01N 2800/52* (2013.01)

(58) Field of Classification Search
CPC .......................... G01N 33/5073; A61K 31/416
See application file for complete search history.

(56) References Cited

U.S. PATENT DOCUMENTS

| | | |
|---|---|---|
| 7,504,225 B2 | 3/2009 | Ring |
| 9,289,492 B2 | 3/2016 | Donahoe |
| 2003/0119080 A1 | 6/2003 | Mangano |
| 2004/0037815 A1 | 2/2004 | Clarke |
| 2007/0026469 A1 | 2/2007 | Fuchs |
| 2007/0254319 A1 | 11/2007 | Donnenberg |
| 2008/0187938 A1 | 8/2008 | Wicha |
| 2010/0093556 A1 | 4/2010 | Clarke et al. |

FOREIGN PATENT DOCUMENTS

| | | | |
|---|---|---|---|
| WO | 2009/012357 | 1/2009 | |
| WO | WO2009126310 | * 10/2009 | ........... G01N 33/574 |

OTHER PUBLICATIONS

Wei et al. PNAS. Nov. 2, 2010; 107(44): 18874-18879.*
Wei et al. PNAS. Nov. 2, 2010; 107(44): 18874-18879 and Supporting Information pp. 1-8.*
Ahmed et al. (Current Cancer Drug Targets. 2010; 10: 268-278).*
Gao et al. (Oncogene. 2010; 29:2672-2680).*
Papakostas et al., Protein Expr Purif, 70(1):32-8 (2010). "Development of an efficiently cleaved, bioactive, highly pure FLAG-tagged recombinant human Mullerian inhibiting substance."
Wei et al., Proc Natl Acad Sci USA, 107(44):18874-18879 (2010). "Mullerian inhibiting substance preferentially inhibits stem/progenitors in human ovarian cancer cell lines compared with chemotherapeutics."
Albert et al., "Murine Epidermal Label-Retaining Cells Isolated by Flow Cytometry do not Express the Stem Cell Markers CD34, Sca-1, or Flk-1", J Invest Dermatol 117(4) 943-948 (2001).
Al-Hajj et al., "Prospective identification of tumorigenic breast cancer cells", Proc Natl Acad Sci USA 100(7) 3983-3989 (2003).
Alvarez-Buylla et al., "For the Long Run: Maintaining Germinal Niches in the Adult Brain", Neuron 41(5) 683-686 (2004).
Arango et al., "Conditional deletion of beta-catenin in the mesenchyme of the developing mouse uterus results in a switch to adipogenesis in the myometrium", Dev Biol 288(1) 276-283 (2005).
Auersperg et al., "E-cadherin induces mesenchymal-to-epithelial transition in human ovarian surface epithelium", Proc Natl Acad Sci USA 96(11) 6249-6254 (1999).
Behbod et al., "Will Cancer Stem Cells Provide New Therapeutic Targets", Carcinogenesis 26(4) 703-711 (2005).
Berns, "Stem Cells for Lung Cancer", Cell 121(6) 811-813 (2005).
Bhatt et al., "Novel Method for the Isolation and Characterisation of Putative Prostatic Stem Cell", Cytometry 54(2) 89-99 (2003).
Bjersing et al., "Ovulation and the Mechanism of Follicle Rupture. I. Light Microscope Changes in Rabbit Ovarian Follicles Prior to Induced Ovulation", Cell Tissue Res 149(3) 287-300 (1974).
Bjersing et al., "Ovulation and the Role of the Ovarian Surface Epithelium", Experientia 31(5) 605-608 (1975).
Blanpain et al. "Self-Renewal, Multipotency, and the Existence of Two Cell Populations within an Epithelial Stem Cell Niche", Cell 118(5) 635-648 (2004).
Braun et al., "Epidermal Label-Retaining Cells: Background and Recent Applications" J Investig Dermatol Symp Proc 9(3) 196-201 (2004).
Bukovsky et al., "Origin of germ cells and formation of newprimary follicles in adult human ovaries", Reprod Biol Endocrinol 28;2:20 (2004).
Cannistra et al., "Progress in the Management of Gynecological Cancer: Consensus Summary Statement", J Clin Oncol 21(10 Suppl) 129s-132s (2003).
Cannistra, "Cancer of the Ovary", N. Engl J Med 351(24) 2519-2529 (2004).

(Continued)

Primary Examiner — Scott Long
(74) Attorney, Agent, or Firm — Nixon Peabody LLP

(57) ABSTRACT

The present invention generally relates to methods, assays, compositions and kits related to a subpopulation of ovarian cancer stem cells which are selected or enriched by chemotherapeutic agents and inhibited by MIS (Mullerian Inhibiting Substance) and MIS mimetics. In particular, the present invention relates to a population of CD44+/CD24+/EpCam+/ECad− subpopulation of ovarian cancer stem cells. The present invention also provides methods to screen a subject with ovarian cancer to identify if they have an ovarian cancer comprising CD44+/CD24+/EpCam+/ECad− ovarian cancer stem cells, and methods to identify and enrich or isolate for such ovarian cancer cell populations.

6 Claims, 30 Drawing Sheets

(56) References Cited

OTHER PUBLICATIONS

Cheng et al., "Lineage infidelity of epithelial ovarian cancers is controlled by HOX genes that specify regional identity in the reproductive tract" Nat Med 11(5) 531-537 (2005).
Clow et al., "Changes in the mouse ovarian surface epithelium with age and ovulation number" Mol Cell Endocrinol 191(1) 105-111 (2002).
Donnenberg et al., "Constitutive multiple drug resistance in tumor stem cells", American Association for Cancer Research 46:479 (2005).
Doyle et al., "Multidrug resistance mediated by the breast cancer resistance protein BCRP (ABCG2)", Oncogene 22 (47) 7340-7358 (2003).
Drapkin et al., "Expression of Candidate Tumor Markers in Ovarian Carcinoma and Benign Ovary: Evidence for a Link Between Epithelial Phenotype and Neoplasia", Hum Pathol 35(8) 1014-1021 (2004).
Eggan et al., "Ovulated oocytes in adult mice derive from non-circulating germ cells", Nature 441(7097) 1109-1114 (2006).
Fuchs et al., "Socializing with the Neighbors: Stem Cells and Their Niche", Cell 116(6) 769-778 (2004).
Goodell et al., "Isolation and Functional Properties of Murine Hematopoietic Stem Cells that are Replicating in Vivo", J Exp Med 183(4) 1797-1806 (1996).
Gottesman et al., "Biochemistry of Multidrug Resistance Mediated by the Multidrug Transporter", Annu Rev Biochem 62:385-427 (1993).
Gottesman et al., "Multidrug resistance in cancer: Role of ATP-dependent transporters", Nat Rev Cancer 2(1) 48-58 (2002).
Ha et al., "Mullerian Inhibiting Substance Inhibits Ovarian Cell Growth through an Rb-independent Mechanism", J Biol Chem 275(47) 37101-37109 (2000).
Haraguchi et al., "Characterization of a Side Population of Cancer Cells from Human Gastrointestinal System", Stem Cell 24(3) 506-513 (2006).
Heinzelmann-Schwarz et al., "Overexpression of the Cell Adhesion Molecules DDR1, Claudin 3, and Ep-CAM in Metaplastic Ovarian Epithelium and Ovarian Cancer", Clin Cancer Res 10(13) 4427-4436 (2004).
Hirschmann-Jax et al., "A distinct "side population" of cells with high drug efflux capacity in human tumor cells", Proc Natl Acad Sci USA 101(39) 14228-14233 (2004).
Imitola et al., "Neural Stem/Progenitor Cells Express Costimulatory Molecules That Are Differentially Regulated by Inflammatory and Apoptotic Stimuli", Am J Pathol 164(5) 1615-1625 (2004).
Jonker et al., "Contribution of the ABC Transporters BCRPL and Mdr1a/1b to the Side Population Phenotype in Mammary Gland and Bone Marrow of Mice", Stem Cell 23(8) 1059-1065 (2005).
Kenney et al., "Identification of Stem Cell Units in the Terminal End Bud and Duct of the Mouse Mammary Gland", J Biomed Biotechnol 1(3) 133-143 (2001).
Kim et al., "Identification of Epithelial Cell Adhesion Molecule Autoantibody in Patients with Ovarian Cancer", Clin Cancer Res 9(13) 4782-4791 (2003).
Kondo et al., "Biology of Hematopoietic Stem Cells and Progenitors: Implications for Clinical Application", Annu Rev Immunol 21; 759-806 (2003).
Kondo et al., "Peristence of a small subpopulation of cancer-like cells in the C6 glioma cell line", PNAS 101(3) 781-786 (2004).
Konstantinopoulos et al., "Integrated Analysis of Multiple Microarray Datasets Identifies a Reproducible Survival Predictor in Ovarian Cancer", PLoS One 6(3) e18202 (2011).
Leedham et al., "Intestinal stem cells", J. Cell. Mol. Med., 9(1) 11-24 (2005).
Li et al., "Stem Cell Niche: Structure and Function", Annu Rev Cell Dev Biol 21:605-631 (2005).
Li et al., "Identification of Pancreatic Cancer Stem Cells", Cancer Res 67:1030-1037 (2007).
Liu et al., "Airway Glandular Development and Stem Cells", Curr Top Dev Biol 64:33-56 (2004).
Lowry et al., "Defining the impact of the beta-catenin/Tcf transactivation on epithelial stem cells", Genes Dev 19:1596-1611 (2005).
Maliepaard et al., "Overexpression of the BCRP/MXR/ABCP Gene in a Topotecan-selected Ovarian Tumor Cell Line", Cancer Res 59(18) 4559-4563 (1999).
Mao et al., "Role of the Breast Cancer Resistance Protein (ABCG2) in Drug Transport", AAPS J 7(1) E118-133 (2005).
Mills et al., "The intestinal stem cell niche: There grows the neighborhood", Proc Natl Acad Sci USA 98(22) 12334-12336 (2001).
Morris et al., "Evidence That a Slowly cycling Subpopulation of Adult Murine Epidermal Cells Retains Carcinogen", Cancer Res 46(6) 3061-3066 (1986).
Morris et al., "Highly Persistent Label-Retaining Cells in the Hair Follicles of Mice and Their Fate Following Induction of Anagen", J Invest Dermatol 112(4) 470-475 (1999).
Morris et al., "Slowly cycling (label-retaining) epidermal cells behave like clonogenic stem cells in vitro", Cell Prolif 27(5) 279-289 (1994).
Morrison et al., "The Long-Term Repopulating Subset of Hematopoietic Stem Cells Is Deterministic and Isolatable by Phenotype", Immunity 1(8) 661-673 (1994).
Murdoch et al., "Ovulation-Induced DNA Damage in Ovarian Surface Epithelial Cells of Ewes: Prospective Regulatory Mechanisms of Repair/Survival and Apoptosis", Biol Reprod 65(5) 1417-1472 (2001).
Oliver et al., "The renal papilla is a niche for adult kidney stem cells", J Clin Invest 114(6) 795-804 (2004).
Parker et al., "Cancer Statistics, 1997", CA Cancer J Clin 47(1) 5-27 (1997).
Patrawala et al., "Side Population Is Enriched in Tumorigenic, Stem-Like Cancer Cells, whereas ABCG2+ and ABCG2- Cancer Cells Are Similarly Tumorigenic", Cancer Res 65(14) 6207-6219 (2005).
Pieretti-Veanmarcke et al., "Recombinant Human Mullerian Inhibiting Substance Inhibits Long-term Growth of MIS Type II Receptor-Directed Transgenic Mouse Ovarian Cancers in vivo", Clin Cancer Res 12(5) 1593-1598 (2006).
Poste et al., "On the Genesis and Regulation of Cellular Heterogeneity in Malignant Tumors", Invasion Metastasis 2 (3) 137-176 (1982).
Poste et al., "Evolution of tumor cell heterogeneity during progressive growth of individual lung metastases", Proc Natl Acad Sci USA 79(21) 6574-6578 (1982).
Preffer et al., "Lineage-Negative Side-Population 9SP) Cells with Restricted Hematopoietic Capacity Circulate in Normal Human Adult Blood: Immunophenotypic and Functional Characterization", Stem Cells 20(5) 417-427 (2002).
Reya et al., "Stem cells, cancer, and cancer stem cells", Nature 414(6859) 105-111 (2001).
Scully et al., "Recent Progress in Ovarian Cancer", Hum Pathol 1(1) 73-98 (1970).
Seigel et al., "Cancer stem cell characteristics in retinoblastoma", Mol Vis 11:729-737 (2005).
Sell, "Stem cell origin of cancer and differentiation therapy", Crit Rev Oncol Hematol 51(1) 1-28 (2004).
Siegel et al., "Cancer Statistics, 2013", CA Cancer J Clin 63(1) 11-30 (2013).
Smalley et al., "An improved definition of mouse mammary epithelial side population cells", Cytotherapy 7(6) 497-508 (2005).
Smalley et al., "The Mammary Gland "Side Population": A Putative Stem/Progenitor Cell Marker?", J Mammary Gland Biol Neoplasia 10(1) 37-47 (2005).
Spradling et al., "Stem cells find their niche", Nature 414(6859) 98-104 (2001).
Szotek et al., "Ovarian cancer side population defines cells with stem cell-like characteristics and Mullerian Inhibiting Substance responsiveness", Proc Natl Acad Sci USA 103(30) 11154-11159 (2006).

(56) References Cited

OTHER PUBLICATIONS

Szotek et al., "Adult Mouse Myometrial Label-Retaining Cells Divide in Response to Gonadotropin Stimulation", Stem Cells 25(5) 1317-1325 (2007).
Tan et al., "Proliferating Cell Nuclear Antigen Immunoreactivity in the Ovarian Surface Epithelium of Mice of Varying Ages and Total Lifetime Ovulation Number Following Ovulation", Biol Reprod 71(5) 1501-1507 (2004).
Teixeira et al., "Mullerian Inhibiting Substance: An Instructive Development Hormone with Diagnostic and Possible Therapeutic Applications", Endocrine Reviews 22(5) 657-674 (2001).
Tsujimura et al., "Proximal location of mouse prostate epithelial stem cells: A model of prostatic homeostasis", J cell Biol 157(7) 1257-1265 (2002).
Tu et al., "Stem-cell origin of metastasis and heterogeneity in solid tumors", Lancet Oncol 3(8) 508-513 (2002).
Tumbar et al., "Defining the Epithelial Stem Cell Niche in Skin", Science 303(5656) 359-363 (2004).
Vidrich et al., "Intestinal stem cells and mucosal gut development", Curr Opin Gastroenterol 19(6) 583-590 (2003).
Watt et al., "Out of Eden: Stem Cells and Their Niches", Science 287(5457) 1427-1430 (2000).
Welm et al., "Sca-1(pos) Cells in the Mouse Mammary Gland Represent an Enriches Progenitor Cell Population", Dev Biol 245(1) 42-56 (2002).
Welm et al., "Isolation and characterization of functional mammary gland stem cells", Cell Prolif 36(Suppl 1) 17-32 (2003).
Williams et al., "A Stem Cell Niche Theory of Intestinal Crypt Maintenance Based on a Study of Somatic Mutation in Colonic Mucosa", Am J Pathol 141(4) 773-776 (1992).
Wong et al., "Regulation of Intestinal Stem Cells", J Investig Dermatol Symp Proc 9(3) 224-228 (2004).
Wu et al., "In Vivo Labeling and Analysis of Epidermal Stem Cells", Methods Mol Biol 289:73-78 (2005).
Wulf et al., "A leukemic stem cell with intrinsic drug efflux capacity in acute myeloid leukemia", Blood 98(4) 1166-1173 (2001).
Yan et al., "Two-Amino Acid Molecular Switch in an Epithelial Morphogen That Regulates Binding to Two Distinct Receptors", Science 290(5491) 523-527 (2000).
Young et al., "A brief history of the pathology of the gonads", Mod Pathol 2:S3-S17 (2005).
Zhan et al., "Müullerian inhibiting substance regulates its receptor/SMAD signaling and causes mesenchymal transition of the coelomic epithelial cells early in Müllerian duct regression", Development 133(1) 2359-2369 (2006).

\* cited by examiner

| INJECTION OF CELLS | | TIME TO TUMOR APPEARANCE (WEEK) | | | | | | | | |
|---|---|---|---|---|---|---|---|---|---|---|
| | | 1 | 2 | 3 | 4 | 5 | 6 | 7 | 8 | |
| $10^3$ | 3+E- | 0 | 0 | 0 | 0 | 2 | 5 | 8 | | P=0.001 |
| | 3-E+ | 0 | 0 | 0 | 0 | 0 | 2 | 3 | | |
| $10^2$ | 3+E- | 0 | 0 | 0 | 0 | 0 | 2 | 5 | 9 | P=0.002 |
| | 3-E+ | 0 | 0 | 0 | 0 | 0 | 0 | 2 | 3 | |

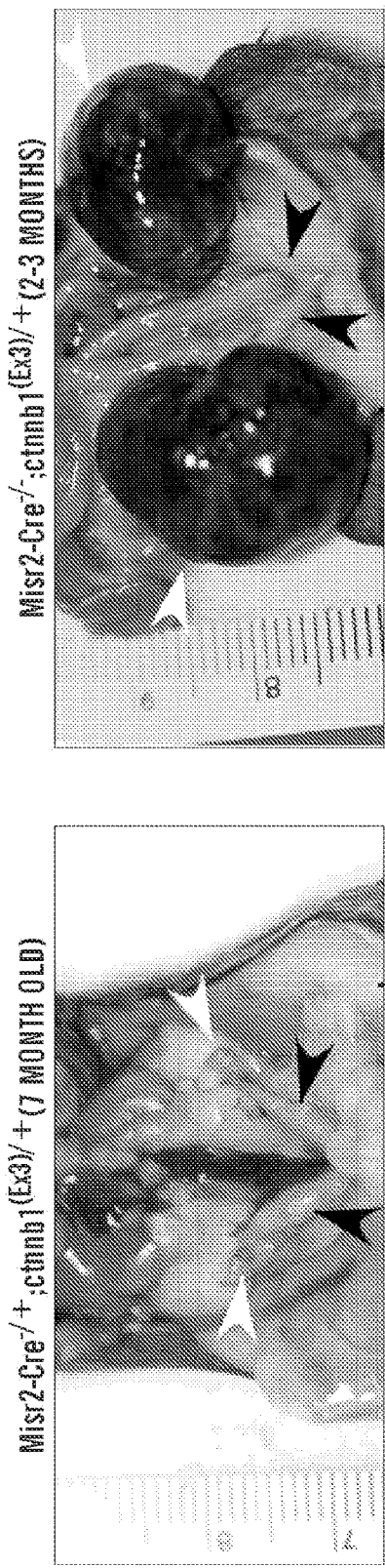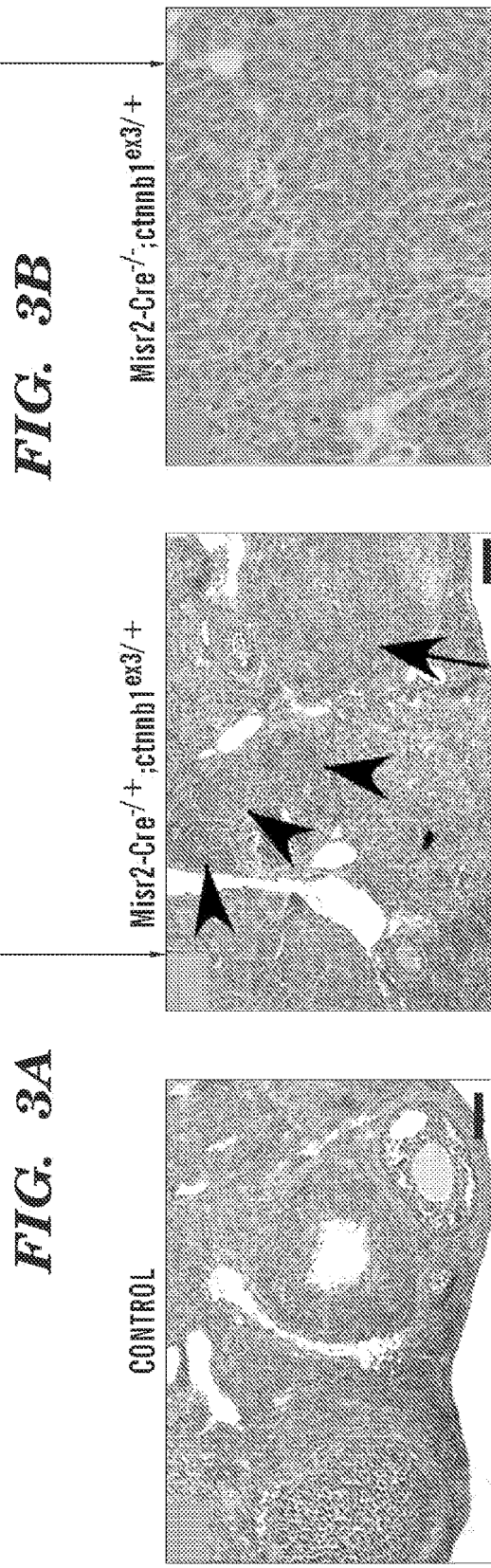
FIG. 3A
FIG. 3B
FIG. 3C
FIG. 3D
FIG. 3E

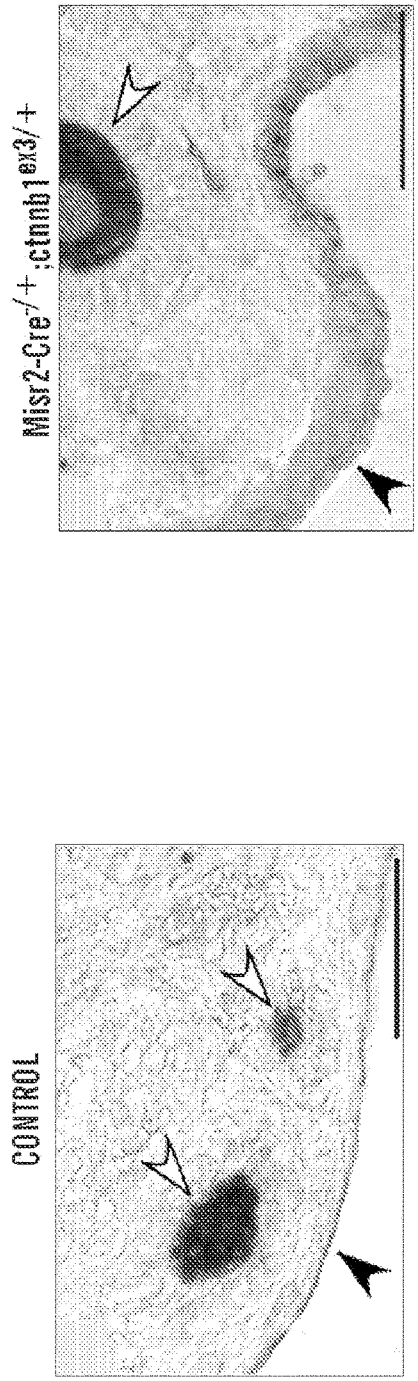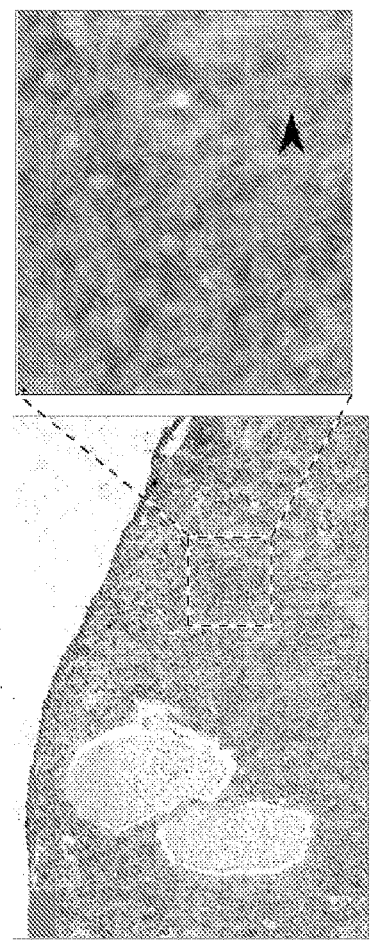
FIG. 3F   FIG. 3G   FIG. 3H

TABLE 1.
PLURIPOTENCY AND X-INACTIVATION IN STEM CELLS

| | SEPARATION | LIN28 | LIN28B | LET7 | Oct-4 | Sox2 | Cmyc | Nanog | KLF4 | ESRBB | Wnt5a | DAX1 | Xist |
|---|---|---|---|---|---|---|---|---|---|---|---|---|---|
| OVCAR 5 | 3+Ecad- | + | | + | - | - | + | - | - | - | - | NT | - |
| | 3-Ecad+ | - | | + | - | + | + | - | - | - | - | NT | - |
| | Neat | + | - | + | - | + | + | - | NT | - | + | NT | - |
| iPS (HUMAN FIBROBLASTS) | N/A | + | + | + | + | + | + | + | - | - | + | NT | + |
| XENOGRAFTS | 3+Ecad- | + | | | | | + | | | | + | | |
| | 3-Ecad+ | - | | | | + | + | + | | | - | | |
| | 3+ | | | | | | | | | | | | |
| | 3- | | | | | | | | | | | | |
| ASCITES | 3+ | - | | + | | | | | | | | | + |
| | 3- | - | | - | | | | | | | | | + |
| OVCAR 5 MIS (100µg/ml) 20h | 3+Ecad- | + | | + | | | | | | | | | |
| | 3-Ecad+ | - | | - | | | | | | | | | |
| OVCAR 5 DOX (60nM) 20h | 3+Ecad- | + | | + | | | | | | | | | |
| | 3-Ecad+ | - | | - | | | | | | | | | |
| SKOV3 | Neat | | - | + | | + | + | - | | | - | | - |

FIG. 7

SCREENING OF PLURIPOTENCY FACTORS BY RT-PCR

|  | SEPARATION | LIN28 | LIN28B | Oct-4 | Sox2 | Cmyc | Nanog | KLF4 |
|---|---|---|---|---|---|---|---|---|
| OVCAR 5 | 3+Ecad- | + | - | - | - | + | - | - |
|  | 3-Ecad+ | - | - | - | + | + | - | - |
|  | Neat | + |  |  |  |  |  |  |
| XENOGRAFTS | 3+Ecad- | + |  |  | - | + | - | - |
|  | 3-Ecad+ | - |  |  | + | + | - | - |

SEQUENCE LISTING

<160> NUMBER OF SEQ ID NOS: 57

<210> SEQ ID NO 1
<211> LENGTH: 2065
<212> TYPE: DNA
<213> ORGANISM: Homo sapiens

<400> SEQUENCE: 1

```
gcatgttgac acatcaggcc cagctctatc actgggagg gagataggct gccagggaca      60
gaaagggctc tttgagaagg ccactctgcc tggagtgggg gcgccgggca ctgtccccca     120
aggtcgcggc agaggagata ggggtctgtc ctgcacaaac accccaccct ccactcggct     180
```

| | |
|---|---|
| cacttaaggc aggcagccca gccccctggca gcacccacga tgcgggacct gcctctcacc | 240 |
| agcctggccc tagtgctgtc tgccctgggg gctctgctgg ggactgaggc cctcagagca | 300 |
| gaggagccag ctgtgggcac cagtggcctc atcttccgag aagacttgga ctggcctcca | 360 |
| ggcagcccac aagagcctct gtgcctggtg gcactgggcg ggacagcaa tggcagcagc | 420 |
| tcccccctgc gggtggtggg ggctctaagc gcctatgagc aggccttcct ggggccgtg | 480 |
| cagagggccc gctggggccc ccgagacctg gccaccttcg gggtctgcaa caccggtgac | 540 |
| aggcaggctg ccttgccctc tctacggcgg ctggggggcct ggctgcggga ccctggggggg | 600 |
| cagcgcctgg tggtcctaca cctggaggaa gtgacctggg agccaacacc tcgctgagg | 660 |
| ttccaggagc ccccgcctgg aggagctggc cccccagagc tggcgctgct ggtgctgtac | 720 |
| cctgggcctg gccctgaggt cactgtgacg agggctgggc tgccgggtgc ccagagcctc | 780 |
| tgcccctccc gagacacccg ctacctggtg ttagcggtgg accgccctgc gggggcctgg | 840 |
| cgcggctccg ggctggcctt gaccctgcag ccccgcggag aggactcccg gctgagtacc | 900 |
| gcccggctgc aggcactgct gttcggcgac gaccaccgct gcttcacacg gatgaccccg | 960 |
| gccctgctcc tgctgccgcg gtccgagccc gcgccgctgc ctgcgcacgg ccagctggac | 1020 |
| accgtgccct tcccgccgcc caggccatcc gcggaactcg aggagtcgcc acccagcgca | 1080 |
| gacccctccc tggagacgct cacgcgcctg gtgcgggcgc tgcgggtccc ccggcccgg | 1140 |
| gcctccgcgc cgcgcctggc cctggatccg gacgcgctgg ccggcttccc gcagggccta | 1200 |
| gtcaacctgt cggaccccgc ggcgctggag cgcctactcg acggcgagga gccgctgctg | 1260 |
| ctgctgctga ggcccactgc ggccaccacc ggggatcctg cgcccctgca cgaccccacg | 1320 |
| tcggcgccgt gggccacggc cctggcgcgc cgcgtggctg ctgaactgca agcggcggct | 1380 |
| gccgagctgc gaagcctccc gggtctgcct ccggccacag ccccgctgct ggcgcgcctg | 1440 |
| ctcgcgctct gcccaggtgg ccccggcggc ctcggcgatc ccctgcgagc gctgctgctc | 1500 |
| ctgaaggcgc tgcagggcct gcgcgtggag tggcgcgggc gggatccgcg cgggccgggt | 1560 |
| cgggcacagc gcagcgcggg ggccaccgcc gccgacgggc cgtgcgcgct gcgcgagctc | 1620 |
| agcgtagacc tccgcgccga cgctccgta ctcatccccg agacctacca ggccaacaat | 1680 |
| tgccagggcg tgtgcggctg gcctcagtcc gaccgcaacc cgcgctacgg caaccacgtg | 1740 |
| gtgctgctgc tgaagatgca ggccgtgggg ccgccctgg cgcgcccacc ctgctgcgtg | 1800 |
| cccaccgcct acgcgggcaa gctgctcatc agcctgtcgg aggagcgcat cagcgcgcac | 1860 |
| cacgtgccca acatggtggc caccgagtgt ggctgccggt gacccctgcg ccgcgcggac | 1920 |
| tcctgccccg agggtccgga cgcgccccag ctcgcgcccc ttcccatatt tattcggacc | 1980 |
| ccaagcatcg ccccaataaa gaccagcaag caaccggcaa aaaaaaaaaa aaaaaaaaaa | 2040 |
| aaaaaaaaa aaaaaaaaa aaaaa | 2065 |

<210> SEQ ID NO 2
<211> LENGTH: 560
<212> TYPE: PRT
<213> ORGANISM: Homo sapiens

<400> SEQUENCE: 2

Met Arg Asp Leu Pro Leu Thr Ser Leu Ala Leu Val Leu Ser Ala Leu
1               5                   10                  15

Gly Ala Leu Leu Gly Thr Glu Ala Leu Arg Ala Glu Glu Pro Ala Val
            20                  25                  30

Gly Thr Ser Gly Leu Ile Phe Arg Glu Asp Leu Asp Trp Pro Pro Gly

```
            35                  40                  45
Ser Pro Gln Glu Pro Leu Cys Leu Val Ala Leu Gly Gly Asp Ser Asn
 50                  55                  60

Gly Ser Ser Ser Pro Leu Arg Val Val Gly Ala Leu Ser Ala Tyr Glu
 65                  70                  75                  80

Gln Ala Phe Leu Gly Ala Val Gln Arg Ala Arg Trp Gly Pro Arg Asp
                     85                  90                  95

Leu Ala Thr Phe Gly Val Cys Asn Thr Gly Asp Arg Gln Ala Ala Leu
                    100                 105                 110

Pro Ser Leu Arg Arg Leu Gly Ala Trp Leu Arg Asp Pro Gly Gly Gln
                115                 120                 125

Arg Leu Val Val Leu His Leu Glu Glu Val Thr Trp Glu Pro Thr Pro
            130                 135                 140

Ser Leu Arg Phe Gln Glu Pro Pro Gly Gly Ala Gly Pro Pro Glu
145                 150                 155                 160

Leu Ala Leu Leu Val Leu Tyr Pro Gly Pro Gly Pro Glu Val Thr Val
                    165                 170                 175

Thr Arg Ala Gly Leu Pro Gly Ala Gln Ser Leu Cys Pro Ser Arg Asp
                180                 185                 190

Thr Arg Tyr Leu Val Leu Ala Val Asp Arg Pro Ala Gly Ala Trp Arg
            195                 200                 205

Gly Ser Gly Leu Ala Leu Thr Leu Gln Pro Arg Gly Glu Asp Ser Arg
210                 215                 220

Leu Ser Thr Ala Arg Leu Gln Ala Leu Leu Phe Gly Asp His Arg
225                 230                 235                 240

Cys Phe Thr Arg Met Thr Pro Ala Leu Leu Leu Pro Arg Ser Glu
                245                 250                 255

Pro Ala Pro Leu Pro Ala His Gly Gln Leu Asp Thr Val Pro Phe Pro
                260                 265                 270

Pro Pro Arg Pro Ser Ala Glu Leu Glu Glu Ser Pro Pro Ser Ala Asp
                275                 280                 285

Pro Phe Leu Glu Thr Leu Thr Arg Leu Val Arg Ala Leu Arg Val Pro
                290                 295                 300

Pro Ala Arg Ala Ser Ala Pro Arg Leu Ala Leu Asp Pro Asp Ala Leu
305                 310                 315                 320

Ala Gly Phe Pro Gln Gly Leu Val Asn Leu Ser Asp Pro Ala Ala Leu
                    325                 330                 335

Glu Arg Leu Leu Asp Gly Glu Glu Pro Leu Leu Leu Leu Arg Pro
                340                 345                 350

Thr Ala Ala Thr Thr Gly Asp Pro Ala Pro Leu His Asp Pro Thr Ser
                355                 360                 365

Ala Pro Trp Ala Thr Ala Leu Ala Arg Arg Val Ala Ala Glu Leu Gln
                370                 375                 380

Ala Ala Ala Ala Glu Leu Arg Ser Leu Pro Gly Leu Pro Pro Ala Thr
385                 390                 395                 400

Ala Pro Leu Leu Ala Arg Leu Ala Leu Cys Pro Gly Gly Pro Gly
                    405                 410                 415

Gly Leu Gly Asp Pro Leu Arg Ala Leu Leu Leu Lys Ala Leu Gln
                420                 425                 430

Gly Leu Arg Val Glu Trp Arg Gly Arg Asp Pro Arg Gly Pro Gly Arg
                435                 440                 445

Ala Gln Arg Ser Ala Gly Ala Thr Ala Ala Asp Gly Pro Cys Ala Leu
450                 455                 460
```

Arg Glu Leu Ser Val Asp Leu Arg Ala Glu Arg Ser Val Leu Ile Pro
465                 470                 475                 480

Glu Thr Tyr Gln Ala Asn Asn Cys Gln Gly Val Cys Gly Trp Pro Gln
            485                 490                 495

Ser Asp Arg Asn Pro Arg Tyr Gly Asn His Val Val Leu Leu Leu Lys
        500                 505                 510

Met Gln Ala Arg Gly Ala Ala Leu Ala Arg Pro Pro Cys Cys Val Pro
        515                 520                 525

Thr Ala Tyr Ala Gly Lys Leu Leu Ile Ser Leu Ser Glu Glu Arg Ile
        530                 535                 540

Ser Ala His His Val Pro Asn Met Val Ala Thr Glu Cys Gly Cys Arg
545                 550                 555                 560

<210> SEQ ID NO 3
<211> LENGTH: 1863
<212> TYPE: DNA
<213> ORGANISM: Homo sapiens

<400> SEQUENCE: 3
gtatctgaag aaagatttgg ccaggggcag ctgtgctggc ttatgctctt ctccttctgc      60
tgctgccatc ctccagcaag atgctagggt ctttggggct ttgggcatta cttcccacag     120
ctgtggaagc accccaaac aggcgaacct gtgtgttctt tgaggcccct ggagtgcggg      180
gaagcacaaa gacactggga gagctgctag atacaggcac agagctcccc agagctatcc     240
gctgcctcta cagccgctgc tgctttggga tctggaacct gacccaagac cgggcacagg     300
tggaaatgca aggatgccga acagtgatg agccaggctg tgagtccctc cactgtgacc      360
caagtccccg agcccacccc agccctggct ccactctctt cacctgctcc tgtggcactg     420
acttctgcaa tgccaattac agccatctgc ctcctccagg gagccctggg actcctggct     480
cccagggtcc ccaggctgcc ccaggtgagt ccatctggat ggcactggtg ctgctggggc     540
tgttcctcct cctcctgctg ctgctgggca gcatcatctt ggccctgcta cagcgaaaga    600
actacagagt gcgaggtgag ccagtgccag agccaaggcc agactcaggc agggactgga    660
gtgtggagct gcaggagctg cctgagctgt gtttctccca ggtaatccgg gaaggaggtc    720
atgcagtggt ttgggccggg cagctgcaag gaaaactggt tgccatcaag gccttcccac    780
cgaggtctgt ggctcagttc caagctgaga gagcattgta cgaacttcca ggcctacagc    840
acgaccacat tgtccgattt atcactgcca gccggggggg tcctggccgc ctgctctctg    900 ggccccctgct ggtactggaa ctgcatccca agggctccct gtgccactac ttgacccagt    960
acaccagtga ctggggaagt tccctgcgga tggcactgtc cctggcccag ggcctggcat   1020
ttctccatga ggagcgctgg cagaatggcc aatataaacc aggtattgcc caccgagatc   1080
tgagcagcca gaatgtgctc attcgggaag atggatcgtg tgccattgga gacctgggcc   1140
ttgccttggt gctccctggc ctcactcagc ccctgcctg accccctact caaccacaag   1200
gcccagctgc catcatggaa gctggcaccc agaggtacat ggcaccagag ctcttggaca   1260
agactctgga cctacaggat tggggcatgg ccctccgacg agctgatatt tactcttttgg   1320 ctctgctcct gtgggagata ctgagccgct gcccagattt gaggcctgac agcagtccac   1380
cacccttcca actggcctat gaggcagaac tgggcaatac ccctacctct gatgagctat   1440
gggccttggc agtgcaggag aggaggcgtc cctacatccc atccacctgg cgctgctttg   1500
ccacagaccc tgatgggctg agggagctcc tagaagactg ttgggatgca gacccagaag   1560

```
cacggctgac agctgagtgt gtacagcagc gcctggctgc cttggcccat cctcaagaga    1620
gccacccctt tccagagagc tgtccacgtg gctgcccacc tctctgccca gaagactgta    1680
cttcaattcc tgccctacc atcctcccct gtaggcctca gcggagtgcc tgccacttca     1740
gcgttcagca aggcccttgt tccaggaatc ctcagcctgc ctgtacccct tctcctgtgt    1800
aaatatgcag tttatgtgtc atcaatgtac atgccaacat aaatatggcg attgtatagc    1860
tgt                                                                  1863
```

<210> SEQ ID NO 4
<211> LENGTH: 573
<212> TYPE: PRT
<213> ORGANISM: Homo sapiens

<400> SEQUENCE: 4

```
Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
            20                  25                  30

Arg Gly Ser Thr Lys Thr Leu Gly Glu Leu Leu Asp Thr Gly Thr Glu
        35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Pro Gly Ser
        115                 120                 125

Pro Gly Thr Pro Gly Ser Gln Gly Pro Gln Ala Ala Pro Gly Glu Ser
    130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
        275                 280                 285

His Tyr Leu Thr Gln Tyr Thr Ser Asp Trp Gly Ser Ser Leu Arg Met
    290                 295                 300

Ala Leu Ser Leu Ala Gln Gly Leu Ala Phe Leu His Glu Glu Arg Trp
305                 310                 315                 320
```

Gln Asn Gly Gln Tyr Lys Pro Gly Ile Ala His Arg Asp Leu Ser Ser
              325                 330                 335

Gln Asn Val Leu Ile Arg Glu Asp Gly Ser Cys Ala Ile Gly Asp Leu
          340                 345                 350

Gly Leu Ala Leu Val Leu Pro Gly Leu Thr Gln Pro Pro Ala Trp Thr
      355                 360                 365

Pro Thr Gln Pro Gln Gly Pro Ala Ala Ile Met Glu Ala Gly Thr Gln
  370                 375                 380

Arg Tyr Met Ala Pro Glu Leu Leu Asp Lys Thr Leu Asp Leu Gln Asp
385                 390                 395                 400

Trp Gly Met Ala Leu Arg Arg Ala Asp Ile Tyr Ser Leu Ala Leu Leu
              405                 410                 415

Leu Trp Glu Ile Leu Ser Arg Cys Pro Asp Leu Arg Pro Asp Ser Ser
          420                 425                 430

Pro Pro Pro Phe Gln Leu Ala Tyr Glu Ala Glu Leu Gly Asn Thr Pro
      435                 440                 445

Thr Ser Asp Glu Leu Trp Ala Leu Ala Val Gln Glu Arg Arg Arg Pro
  450                 455                 460

Tyr Ile Pro Ser Thr Trp Arg Cys Phe Ala Thr Asp Pro Asp Gly Leu
465                 470                 475                 480

Arg Glu Leu Leu Glu Asp Cys Trp Asp Ala Asp Pro Glu Ala Arg Leu
              485                 490                 495

Thr Ala Glu Cys Val Gln Gln Arg Leu Ala Ala Leu Ala His Pro Gln
          500                 505                 510

Glu Ser His Pro Phe Pro Glu Ser Cys Pro Arg Gly Cys Pro Pro Leu
      515                 520                 525

Cys Pro Glu Asp Cys Thr Ser Ile Pro Ala Pro Thr Ile Leu Pro Cys
  530                 535                 540

Arg Pro Gln Arg Ser Ala Cys His Phe Ser Val Gln Gln Gly Pro Cys
545                 550                 555                 560

Ser Arg Asn Pro Gln Pro Ala Cys Thr Leu Ser Pro Val
              565                 570

<210> SEQ ID NO 5
<211> LENGTH: 2719
<212> TYPE: DNA
<213> ORGANISM: Homo sapiens

<400> SEQUENCE: 5
tttaggaacg caccgtgcac atgcttggtg gtcttgttaa gtggaaactg ctgctttaga      60
gtttgtttgg aaggtccggg tgactcatcc caacatttac atccttaatt gttaaagcgc     120
tgcctccgag cgcacgcatc ctgagatcct gagcctttgg ttaagaccga gctctattaa     180
gctgaaaaga taaaaactct ccagatgtct tccagtaatg tcgaagtttt tatcccagtg     240
tcacaaggaa acaccaatgg cttccccgcg acagtttcca atgacctgaa ggcatttact     300
gaaggagctg tgttaagttt tcataacatc tgctatcgag taaaactgaa gagtggcttt     360
ctaccttgtc gaaaccagt tgagaaagaa atattatcga atatcaatgg gatcatgaaa     420
cctggtctca acgccatcct gggacccaca ggtggaggca atcttcgtt attagatgtc     480 ttagctgcaa ggaaagatcc aagtggatta tctggagatg ttctgataaa tggagcaccg     540
cgacctgcca atttcaaatg taattcaggt tacgtggtac aagatgatgt tgtgatgggc     600
actctgacgg tgagagaaaa cttacagttc tcagcagctc ttcggcttgc aacaactatg     660

| | |
|---|---|
| acgaatcatg aaaaaaacga acggattaac agggtcattg aagagttagg tctggataaa | 720 |
| gtggcagact ccaaggttgg aactcagttt atccgtggtg tgtctggagg agaaagaaaa | 780 |
| aggactagta taggaatgga gcttatcact gatccttcca tcttgtcctt ggatgagcct | 840 |
| acaactggct tagactcaag cacagcaaat gctgtccttt tgctcctgaa aaggatgtct | 900 |
| aagcagggac gaacaatcat cttctccatt catcagcctc gatattccat cttcaagttg | 960 |
| tttgatagcc tcaccttatt ggcctcagga agacttatgt tccacgggcc tgctcaggag | 1020 |
| gccttgggat actttgaatc agctggttat cactgtgagg cctataataa ccctgcagac | 1080 |
| ttcttcttgg acatcattaa tggagattcc actgctgtgg cattaaacag agaagaagac | 1140 |
| tttaaagcca cagagatcat agagccttcc aagcaggata agccactcat agaaaaatta | 1200 |
| gcggagattt atgtcaactc ctccttctac aaagagacaa aagctgaatt acatcaactt | 1260 |
| tccgggggtg agaagaagaa gaagatcaca gtcttcaagg agatcagcta caccacctcc | 1320 |
| ttctgtcatc aactcagatg ggtttccaag cgttcattca aaaacttgct gggtaatccc | 1380 |
| caggcctcta tagctcagat cattgtcaca gtcgtactgg gactggttat aggtgccatt | 1440 |
| tactttgggc taaaaaatga ttctactgga atccagaaca gagctggggt tctcttcttc | 1500 |
| ctgacgacca accagtgttt cagcagtgtt tcagccgtgg aactctttgt ggtagagaag | 1560 |
| aagctcttca tacatgaata catcagcgga tactacagag tgtcatctta tttccttgga | 1620 |
| aaactgttat ctgatttatt acccatgagg atgttaccaa gtattatatt tacctgtata | 1680 |
| gtgtacttca tgttaggatt gaagccaaag gcagatgcct tcttcgttat gatgtttacc | 1740 |
| cttatgatgg tggcttattc agccagttcc atggcactgg ccatagcagc aggtcagagt | 1800 |
| gtggtttctg tagcaacact tctcatgacc atctgttttg tgtttatgat gatttttttca | 1860 |
| ggtctgttgg tcaatctcac aaccattgca tcttggctgt catggcttca gtacttcagc | 1920 |
| attccacgat atggatttac ggctttgcag cataatgaat ttttgggaca aaacttctgc | 1980 |
| ccaggactca atgcaacagg aaacaatcct tgtaactatg caacatgtac tggcgaagaa | 2040 |
| tatttggtaa agcagggcat cgatctctca ccctggggct tgtggaagaa tcacgtggcc | 2100 |
| ttggcttgta tgattgttat tttcctcaca attgcctacc tgaaattgtt atttcttaaa | 2160 |
| aaatattctt aaatttcccc ttaattcagt atgatttatc ctcacataaa aaagaagcac | 2220 |
| tttgattgaa gtattcaatc aagttttttt gttgttttct gttcccttgc catcacactg | 2280 |
| ttgcacagca gcaattgttt taaagagata catttttaga aatcacaaca aactgaatta | 2340 |
| aacatgaaag aacccaagac atcatgtatc gcatattagt taatctcctc agacagtaac | 2400 |
| catggggaag aaatctggtc taatttatta atctaaaaaa ggagaattga attctggaaa | 2460 |
| ctcctgacaa gttattactg tctctggcat ttgtttcctc atctttaaaa tgaataggta | 2520 |
| ggttagtagc ccttcagtct taatacttta tgatgctatg gtttgccatt atttaatata | 2580 |
| tgacaaatgt attaatgcta tactggaaat gtaaaattga aaatatgttg gaaaaaagat | 2640 |
| tctgtcttat agggtaaaaa aagccaccgg tgatagaaaa aaaatctttt tgataagcac | 2700 |
| attaaagtta atagaactt | 2719 |

<210> SEQ ID NO 6
<211> LENGTH: 655
<212> TYPE: PRT
<213> ORGANISM: Homo sapiens

<400> SEQUENCE: 6

Met Ser Ser Ser Asn Val Glu Val Phe Ile Pro Val Ser Gln Gly Asn

-continued

```
1               5                   10                  15
Thr Asn Gly Phe Pro Ala Thr Ala Ser Asn Asp Leu Lys Ala Phe Thr
                20                  25                  30
Glu Gly Ala Val Leu Ser Phe His Asn Ile Cys Tyr Arg Val Lys Leu
            35                  40                  45
Lys Ser Gly Phe Leu Pro Cys Arg Lys Pro Val Glu Lys Glu Ile Leu
50                  55                  60
Ser Asn Ile Asn Gly Ile Met Lys Pro Gly Leu Asn Ala Ile Leu Gly
65                  70                  75                  80
Pro Thr Gly Gly Gly Lys Ser Ser Leu Leu Asp Val Leu Ala Ala Arg
                    85                  90                  95
Lys Asp Pro Ser Gly Leu Ser Gly Asp Val Leu Ile Asn Gly Ala Pro
                100                 105                 110
Arg Pro Ala Asn Phe Lys Cys Asn Ser Gly Tyr Val Val Gln Asp Asp
                115                 120                 125
Val Val Met Gly Thr Leu Thr Val Arg Glu Asn Leu Gln Phe Ser Ala
        130                 135                 140
Ala Leu Arg Leu Ala Thr Thr Met Thr Asn His Glu Lys Asn Glu Arg
145                 150                 155                 160
Ile Asn Arg Val Ile Gln Glu Leu Gly Leu Asp Lys Val Ala Asp Ser
                165                 170                 175
Lys Val Gly Thr Gln Phe Ile Arg Gly Val Ser Gly Gly Glu Arg Lys
            180                 185                 190
Arg Thr Ser Ile Gly Met Glu Leu Ile Thr Asp Pro Ser Ile Leu Phe
        195                 200                 205
Leu Asp Glu Pro Thr Thr Gly Leu Asp Ser Ser Thr Ala Asn Ala Val
    210                 215                 220
Leu Leu Leu Leu Lys Arg Met Ser Lys Gln Gly Arg Thr Ile Ile Phe
225                 230                 235                 240
Ser Ile His Gln Pro Arg Tyr Ser Ile Phe Lys Leu Phe Asp Ser Leu
                245                 250                 255
Thr Leu Leu Ala Ser Gly Arg Leu Met Phe His Gly Pro Ala Gln Glu
                260                 265                 270
Ala Leu Gly Tyr Phe Glu Ser Ala Gly Tyr His Cys Glu Ala Tyr Asn
            275                 280                 285
Asn Pro Ala Asp Phe Phe Leu Asp Ile Ile Asn Gly Asp Ser Thr Ala
        290                 295                 300
Val Ala Leu Asn Arg Glu Glu Asp Phe Lys Ala Thr Glu Ile Ile Glu
305                 310                 315                 320
Pro Ser Lys Gln Asp Lys Pro Leu Ile Glu Lys Leu Ala Glu Ile Tyr
                325                 330                 335
Val Asn Ser Ser Phe Tyr Lys Glu Thr Lys Ala Glu Leu His Gln Leu
                340                 345                 350
Ser Gly Gly Glu Lys Lys Lys Ile Thr Val Phe Lys Glu Ile Ser
            355                 360                 365
Tyr Thr Thr Ser Phe Cys His Gln Leu Arg Trp Val Ser Lys Arg Ser
        370                 375                 380
Phe Lys Asn Leu Leu Gly Asn Pro Gln Ala Ser Ile Ala Gln Ile Ile
385                 390                 395                 400
Val Thr Val Val Leu Gly Leu Val Ile Gly Ala Ile Tyr Phe Gly Leu
                405                 410                 415
Lys Asn Asp Ser Thr Gly Ile Gln Asn Arg Ala Gly Val Leu Phe Phe
                420                 425                 430
```

```
Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
            500                 505                 510

Leu Met Met Val Ala Tyr Ser Ala Ser Met Ala Leu Ala Ile Ala
            515                 520                 525

Ala Gly Gln Ser Val Val Ser Val Ala Thr Leu Leu Met Thr Ile Cys
        530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
            580                 585                 590

Pro Gly Leu Asn Ala Thr Gly Asn Asn Pro Cys Asn Tyr Ala Thr Cys
        595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655

<210> SEQ ID NO 7
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccggcccagt aagaatgcaa cttaactcga gttaagttgc attcttactg ggttttg      58

<210> SEQ ID NO 8
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccggcaaagg agacaggtgc tacaactcga gttgtagcac ctgtctcctt tgttttg      58

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
```
ccggcatctg taagtggttc aacgtctcga gacgttgaac cacttacaga tgttttg    58

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcggacttct ccggggccag    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcgcagccac ctgcaaactg    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcagtttgca ggtggctgcg    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gctggggtgg cagcttgcat    20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agccccttgg atattccagt c    21

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aatgtgaatt ccactggttc tcct                                           24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
accttggctg ccgtctctgg c                                              21

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agcaaagcct cccaatccca aaca                                           24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tctccaacat cctgaacctc agct                                           24

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaggccttct gcgtcacacc a                                              21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cggcggcaat agcatggcga                                                20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cggcatcgcg gttttttgcgt                                               20

```
<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cggcggcaat agcatggcga                                                 20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcggcgccgg ggagatacat                                                 20

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgagtcagtg aacagggaat gggt                                            24

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acctacgtgt ggccccaagg aat                                             23

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggcagcttgg aaggcagatg ca                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tcggaccaca tccttctcga gc                                              22
```

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 28
cccgagcaag gacgcgactc                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 29
cgcgggaggc tgctggtttt                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 30
gcagccacct ggcgagtctg                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 31
ccgccagcgg ttattcgggg                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 32
tgccccgaat aaccgctggc                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 33
cgccaggttg aagggagccg                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgggcatctg taagtggttc                                               20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cagacccttg gctgacttct                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggggcaagtg gagacggtgc                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cctgggcgct gcccatcatc                                               20

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
atatttgcgt tccgctgggt gc                                            22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttgggattgg ccgcgaagtt cc                                            22

<210> SEQ ID NO 40

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tggatttggg agaactgcgc tgc                                            23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
caggaaacct gctctggcag cat                                            23

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
accgggagct ggtgcatcct                                                20

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tcttggacat tggggctggc ac                                             22

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atatttgcgt tccgctgggt gc                                             22

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttgggattgg ccgcgaagtt cc                                             22

<210> SEQ ID NO 46
<211> LENGTH: 22
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
acccaactac cagctgtggg gt                                              22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcggaacagg tcggacatca cc                                              22

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cgccagacgt aaacagctcc gaatt                                           25

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aggcagatgg tttaagagtg cct                                             23

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccctgtggta ccgagcacct g                                               21

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aatagggccc tgcgggtcac                                                 20

<210> SEQ ID NO 52
<211> LENGTH: 20
<212> TYPE: DNA

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
tggtctggcc cgaagcgtcc                                                    20

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 53 gcagggatc ttacgctcgg cta                                                 23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
ggagccaaaa gggtcatcat ctc                                                23

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
agaagactgt ggatggcccc tc                                                 22

<210> SEQ ID NO 56
<211> LENGTH: 1846
<212> TYPE: DNA
<213> ORGANISM: Homo sapiens

<400> SEQUENCE: 56
ggcacgaggg cagctgtgct ggcttatgct cttctccttc tgctgctgcc atcctccagc        60
aagatgctag ggtctttggg gctttgggca ttacttccca cagctgtgga agcaccccca       120
aacaggcgaa cctgtgtgtt ctttgaggcc cctggagtgc ggggaagcac aaagacactg       180
ggagagctgc tagatacagg cacagagctc cccagagcta tccgctgcct ctacagccgc       240
tgctgctttg ggatctggaa cctgacccaa gaccgggcac aggtggaaat gcaaggatgc       300
cgagacagtg atgagccagg ctgtgagtcc ctccactgtg acccaagtcc ccgagcccac       360
cccagccctg gctccactct cttcacctgc tcctgtggca ctgacttctg caatgccaat       420
tacagccatc tgcctcctcc agggagccct gggactcctg ctcccaggg tccccaggct       480 gccccaggtg agtccatctg gatggcactg gtgctgctgg ggctgttcct cctcctcctg       540
ctgctgctgg gcagcatcat cttggccctg ctacagcgaa agaactacag agtgcgaggt       600
gagccagtgc cagagccaag gccagactca ggcagggact ggagtgtgga gctgcaggag       660
ctgcctgagc tgtgtttctc ccaggtaatc cgggaaggag gtcatgcagt ggtttgggcc       720

```
gggcagctgc aaggaaaact ggttgccatc aaggccttcc caccgaggtc tgtggctcag    780
ttccaagctg agagagcatt gtacgaactt ccaggcctac agcacgacca cattgtccga    840
tttatcactg ccagccgggg gggtcctggc cgcctgctct ctgggcccct gctggtactg    900
gaactgcatc ccaagggctc cctgtgccac tacttgaccc agtacaccag tgactgggga    960
agttccctgc ggatggcact gtccctggcc cagggcctgg catttctcca tgaggagcgc   1020
tggcagaatg ccaatataaa accaggtatt gcccaccgag atctgagcag ccagaatgtg   1080
ctcattcggg aagatggatc atgtgccatt ggagacctgg ccttgccttt ggtgctccct   1140
ggcctcactc agcccctgc ctggacccct actcaaccac aaggcccagc tgccatcatg    1200
gaagctggca cccagaggta catggcacca gagctcttgg acaagactct ggacctacag   1260 gattgggca tggccctccg acgagctgat atttactctt tggctctgct cctgtgggag    1320
atactgagcc gctgcccaga tttgaggcct gacagcagtc caccacccct ccaactggcc   1380
tatgaggcag aactgggcaa tacccctacc tctgatgagc tatgggcctt ggcagtgcag   1440
gagaggaggc gtccctacat cccatccacc tggcgctgct ttgccacaga ccctgatggg   1500
ctgagggagc tcctagaaga ctgttgggat gcagacccag aagcacggct gacagctgag   1560
tgtgtacagc agcgcctggc tgccttggcc catcctcaag agagccaccc ctttccagag   1620
agctgtccac gtggctgccc acctctctgc ccagaagact gtacttcaat tcctgcccct   1680
accatcctcc cctgtaggcc tcagcggagt gcctgccact cagcgttca gcaaggccct    1740 tgttccagga atcctcagcc tgcctgtacc ctttctcctg tgtaaatatg cagtttatgt   1800
gtcatcaatg tacatgccaa cataaatatg gcgattgtat agctgt                 1846

<210> SEQ ID NO 57
<211> LENGTH: 4445
<212> TYPE: DNA
<213> ORGANISM: Homo sapiens

<400> SEQUENCE: 57
gtcagcgctg cctgagctcg tcccctggat gtccgggtct ccccaggcgg ccacccgccg     60
gctcccatcg tgacctccag ccgcagcgcc tcccacgccg ccgccgcgc gaggggagcg    120 ctcgggcgcg ccgggtgtgg ttgggggaag gggttgtgcc gcgcgcgggc tgcgtgctgt    180
gcccactcaa aaggttccgg gcgcgcagga gggaagaggc agtgcccgcc actcccactg    240
agattgagag acgcggcaag gaggcagcct gtggaggaac tgggtaggat ttaggaacgc    300
accgtgcaca tgcttggtgg tcttgttaag tggaaactgc tgctttagag tttgtttgga    360
aggtccgggt gactcatccc aacatttaca tccttaattg ttaaagcgct gcctccgagc    420
gcacgcatcc tgagatcctg agcctttggt taagaccgag ctctattaag ctgaaaagat    480
aaaaactctc cagatgtctt ccagtaatgt cgaagttttt atcccagtgt cacaaggaaa    540
caccaatggc ttccccgcga cagcttccaa tgacctgaag gcatttactg aaggagctgt    600
gttaagtttt cataacatct gctatcgagt aaaactgaag agtggctttc taccttgtcg    660
aaaaccagtt gagaaagaaa tattatcgaa tatcaatggg atcatgaaac ctggtctcaa    720
cgccatcctg ggacccacag gtggaggcaa atcttcgtta ttagatgtct tagctgcaag    780
gaaagatcca agtggattat ctggagatgt tctgataaat ggagcaccgc gacctgccaa    840
tttcaaatgt aattcaggtt acgtggtaca agatgatgtt gtgatgggca ctctgacggt    900
gagagaaaac ttacagttct cagcagctct tcggcttgca acaactatga cgaatcatga    960
```

```
aaaaaacgaa cggattaaca gggtcattca agagttaggt ctggataaag tggcagactc    1020
caaggttgga actcagttta tccgtggtgt gtctggagga gaaagaaaaa ggactagtat    1080
aggaatggag cttatcactg atccttccat cttgttcttg gatgagccta caactggctt    1140
agactcaagc acagcaaatg ctgtcctttt gctcctgaaa aggatgtcta agcagggacg    1200
aacaatcatc ttctccattc atcagcctcg atattccatc ttcaagttgt ttgatagcct    1260
caccttattg gcctcaggaa gacttatgtt ccacgggcct gctcaggagg ccttgggata    1320 cttttgaatca gctggttatc actgtgaggc ctataataac cctgcagact tcttcttgga    1380
catcattaat ggagattcca ctgctgtggc attaaacaga gaagaagact ttaaagccac    1440
agagatcata gagccttcca agcaggataa gccactcata gaaaaattag cggagattta    1500
tgtcaactcc tccttctaca agagacaaa agctgaatta catcaacttt ccggggtga    1560 gaagaagaag aagatcacag tcttcaagga gatcagctac accacctcct tctgtcatca    1620
actcagatgg gtttccaagc gttcattcaa aaacttgctg ggtaatcccc aggcctctat    1680
agctcagatc attgtcacag tcgtactggg actggttata ggtgccattt actttgggct    1740
aaaaaatgat tctactggaa tccagaacag agctggggtt ctcttcttcc tgacgaccaa    1800
ccagtgtttc agcagtgttt cagccgtgga actcttgtg gtagagaaga agctcttcat    1860
acatgaatac atcagcggat actacagagt gtcatcttat ttccttggaa aactgttatc    1920
tgatttatta cccatgagga tgttaccaag tattatattt acctgtatag tgtacttcat    1980
gttaggattg aagccaaagg cagatgcctt cttcgttatg atgtttaccc ttatgatggt    2040
ggcttattca gccagttcca tggcactggc catagcagca ggtcagagtg tggtttctgt    2100
agcaacactt ctcatgacca tctgttttgt gtttatgatg atttttttcag gtctgttggt    2160 caatctcaca accattgcat cttggctgtc atggcttcag tacttcagca ttccacgata    2220
tggatttacg gctttgcagc ataatgaatt tttgggacaa aacttctgcc caggactcaa    2280
tgcaacagga aacaatcctt gtaactatgc aacatgtact ggcgaagaat atttggtaaa    2340
gcagggcatc gatctctcac cctggggctt gtggaagaat cacgtggcct tggcttgtat    2400
gattgttatt ttcctcacaa ttgcctacct gaaattgtta tttcttaaaa atatattctta    2460 aatttcccct taattcagta tgatttatcc tcacataaaa agaagcact ttgattgaag    2520 tattcaatca gttttttttg ttgttttctg ttcccttgcc atcacactgt tgcacagcag    2580
caattgtttt aaagagatac attttttagaa atcacaacaa actgaattaa acatgaaaga    2640
acccaagaca tcatgtatcg catattagtt aatctcctca gacagtaacc atggggaaga    2700
aatctggtct aatttattaa tctaaaaaag gagaattgaa ttctggaaac tcctgacaag    2760
ttattactgt ctctggcatt tgtttcctca tctttaaaat gaataggtag gttagtagcc    2820
cttcagtctt aatactttat gatgctatgg tttgccatta tttaataaat gacaaatgta    2880
ttaatgctat actggaaatg taaaattgaa aatatgttgg aaaaaagatt ctgtcttata    2940
gggtaaaaaa agccaccgtg atagaaaaa atcttttg ataagcacat taagttaat    3000 agaacttact gatattcctg tctagtggta taatatctca ggaatcttgg ctgagggttt    3060
ggaactgtgg gtagagtaga gggccaggag tccagtaata gaattcttgc accatttctg    3120
gaacattcta gctctgggag gtcacgtaac cttcttgggg tagttcagtg gtttagtggt    3180
ttataatcca ggtgtgcgtc agaatcatct gaggaacttt gctaaaatac aaaaatctgg    3240
cctaagtagc tccagatcta ccttcataaa ggaatctgac cactcctgga tttggtaatt    3300
tccaagttct gaaaatttta cttaggattt aataactatt aacatctgtc cctacatagg    3360
```

```
ttttctttcc tacttatata ccttatgttc tcttcattct aaccttcatc agtaataggg     3420
aaatgtttta attttatttt tttagttgaa gggtaatgta ccaaaaaata tagttcagtg     3480
aattaaaatg aacacacatg tgcaaccatc aattcaggtc aagaaataga agattgtagc     3540
acacaaaagc ctactcagcc attctcccag tcactacttc cttccttacc cctgggttat     3600
ttttgaaatg acacttgatg tatttccctc tgttgctgtt atgagaacat tgctacagcc     3660
aagtgttgtg tttctgtgtg cataggttga tacttaatta tctccccact ttttaataaa     3720
cttttaattt ggaaataatt ttagattgac agaaaagttg caaagatagt gaggaaagtt     3780
cctgtctact ctttgctcag cttcccttaa tgttaacatt ttatatagca agatgcattt     3840
gtcaaagcta acaagttaac attggtacaa tcactgttaa ttaaactgca cacaatattc     3900
agatttcacc acttttccac taatattctt tcattgttct aggattcaat tcaggagacc     3960
acatttcatc tagccctctt ttttaaaagt aaatactttt cagcacttac aggagttaac     4020
tgagctgggg catcatggtg tatagacgcc ctgacactgg tcatcttgga attcatttag     4080
tttgtcagtg ggtgccctga cattctgtca caacatcaat ttgggaacat ggcattatat     4140
ttttatcttt gaactttttt cttttggat gacatttgat taatgcgtca tcttggaaca      4200
cattatcttt tttcttggtt atgtgatcag gaagattaat cagtttttcc tgttcttggt     4260
ataattcctg cttttcacat acctgtccct tacagttctc tatatatacc cttcccttat     4320
tacacagaga gaaatatcta tctatacttt ttacacaaaa tatacttcaa aagaaacaaa     4380
acagccacaa ttattaactt tttaaataaa tgagaattta attatatcct aaaaaaaaaa     4440
aaaaa                                                                 4445
```

OVARIAN CANCER STEM CELLS AND METHODS OF ISOLATION AND USES THEREOF

CROSS REFERENCE TO RELATED APPLICATIONS

This Application claims benefit under 35 U.S.C. §119(e) to U.S. Provisional Application 61/493,081, filed, Jun. 3, 2011 the entire contents of which are incorporated herein by reference.

CROSS REFERENCE TO RELATED APPLICATIONS

This Application is a 35 U.S.C. §371 National Phase Entry Application of International Application No. PCT/US2012/040489 filed Jun. 1, 2012, which designates the U.S., and which claims benefit under 35 U.S.C. §119(e) of U.S. Provisional Application No. 61/493,081, filed Jun. 3, 2011, the entire contents of each of which are incorporated herein by reference in their entireties.

GOVERNMENT SUPPORT

The present application was made with Government support under Grant Numbers NIH R01 CA17393 awarded by the National Institutes for Health (NIH). The Government of the United States has certain rights in the invention.

SEQUENCE LISTING

The instant application contains a Sequence Listing which has been submitted in ASCII format via EFS-Web and is hereby incorporated by reference in its entirety. Said ASCII copy, created on Dec. 2, 2013, is named 030258-070842-US_SL.txt and is 44,231 bytes in size.

FIELD OF THE INVENTION

The present invention relates generally to methods and compositions to treat cancer, and more particularly to treating and/or preventing ovarian cancer, in particular where the ovarian cancer comprises CD44+, CD24+, EpCam+ and E-Cadherin− ovarian cancer stem cells. The present invention further provides methods to identify and/or enrich for populations of CD44+, CD24+, EpCam+ and E-Cadherin− ovarian cancer stem cells, and method of use, and kits for isolation thereof.

BACKGROUND

Ovarian cancer may be a prototypical stem cell disease since of its 25,000 new cases per year in the United States 70% recur and die despite early favorable initial clinical responses to surgery and cytotoxic drug therapy. Little progress has been made in improving cure rates as early peritoneal seeding and metastatic spread accounts for the fact that less than 25% of women are diagnosed at the more favorable stage I. The critical barrier to improvement in ovarian cancer therapy is the high incidence of recurrence often attributed to multi-drug resistance; thus, novel therapies must be found. Women with late-stage ovarian cancer usually develop chemotherapeutic-resistant recurrence. It has been theorized that a rare cancer stem cell, which is responsible for the growth and maintenance of the tumor, is also resistant to conventional chemotherapeutics.

Mullerian Inhibiting Substance (MIS) (Teixeira et al. 2001), a 140 kDa glycoprotein disulfide linked homodimer secreted by fetal testes, causes Mullerian duct regression in vertebrate embryos. Epithelial ovarian cancer recapitulates the original histology of the embryonic Mullerian ducts and its various subtypes (Scully 1977); for example, serous cystadenocarcinoma resembles embryonic Fallopian tube, endometrioid carcinoma, the endometrium, and mucinous carcinoma, the cervix. MISRII is expressed in the majority of epithelial ovarian cancers (Masiakos et al. 1999; Bakkum-Gamez et al. 2008; Song et al. 2009) and MIS inhibits their growth in vitro and in vivo, without obvious toxicity after prolonged therapy in vivo (Pieretti-Vanmarcke et al. 2006b). Also, MIS acts synergistically or additively with commonly used cancer drugs to control tumor growth (Pieretti-Vanmarcke et al. 2006a). There is a growing body of research reporting that ovarian cancers and cell lines are heterogeneous, with populations that are resistant to drugs but remain responsive to MIS. MIS particularly targets a population (3+) of cells with stem/progenitor characteristics that respond poorly to chemotherapeutic agents currently in clinical use for ovarian cancer (Wei et al, 2010).

Isolation and molecular scrutiny of a stem/progenitor-enriched population of cancer cells may provide new insights into events leading to early transformation or initiation, progression, maintenance, and recurrence of human ovarian cancers. The identification of markers for these cancer stem/progenitor cells in human ovarian cancer is important in order to develop markers for earlier detection, to discover new therapeutic targets, and to modify therapeutic protocols to include stem cell targets.

The inventors have previously isolated cells by exclusion of Hoechst 34422 dye enriched for a "side population", where these cells had stem/progenitor properties in ovarian cancers from transgenic mice and human ovarian cancer cell lines; They have further enriched this unique population by selecting for cells that expressed three markers (CD44, CD24, and Epcam) from a total of 130 markers compatible for use with flow cytometry and thereby isolated a population of more highly purified human ovarian cancer cells endowed with "stem/progenitor" characteristics (Wei et al, 2010). Cells with the CD44, CD24, and Epcam triple positive (3+) markers were detected in primary ovarian cancers, ovarian cancer cell lines, and normal fimbria as a surrogate cell of origin of ovarian epithelial carcinomas (16), based on the hypothesis that normal somatic and tumor stem/progenitor cells would share many molecular characteristics. The 3+ cells showed stem cell characteristics of 1) shorter tumor free intervals after limiting dilution in vivo and 2) increased colony formation and 3) enhanced migration in vitro.

Stem cells are thought to have properties of pluripotency, defined as the ability to differentiate into multiple cell lineages. Recent studies have shown that it is possible to reprogram adult somatic cells by overexpression of key pluripotency factors. Four transcription factors, Oct3/4, Sox2, KLF4, and c-Myc, were found to be sufficient to induce pluripotency in adult mouse (Takahashi, 2006) and human (Park, 2008) fibroblasts. Subsequently, a substitution of the microRNA-binding protein, Lin28, for c-Myc also was successful in reprogramming human fibroblasts (Yu, 2007; Lako, 2009). Since Lin28 overexpression has been detected in a number of human cancers, including ovarian cancer (Viswanathan, 2009), and has been shown to derepress Let-7, a known microRNA capable of suppressing oncogenes, we studied Lin28 expression in ovarian cancer cell lines and transgenic cancers. Lin28, through its miRNA target Let-7, is thought to regulate the expression of cell cycle-related genes and to contribute to cancer stem/progenitor cell self-renewal and differentiation.

SUMMARY OF THE INVENTION

In accordance with the present invention, the inventors have discovered a population of ovarian cancer cells that are ovarian cancer stem cells or tumor-initiating cells. More importantly, the inventors have discovered that a portion of previously identified 3+ population (e.g., ovarian cancer stem cells which are CD44+, CD24+ and EpCam+) comprises two distinct populations, a 3+E-Cadherin positive population (e.g., 3+/Ecad+) and a 3+E-Cadherin negative population. The inventors also discovered that the 3+E-Cadherin negative population (e.g., CD44+, CD24+, EpCam+, ECad-, here referred to as "3+/Ecad-") have increased growth in vitro and in vivo and resistance to chemotherapeutic agents, and their proliferation and/or growth can be inhibited by Mullerian Inhibiting Substance (MIS) or a small molecule MIS mimetic, SP600125, or analogues or variants thereof. Since MIS causes the MIS RII epithelial population in the embryonic coelomic to migrate (Zhan et al, 2006; Fojino et al, 2010) into the mesenchyme and become vimentin positive and to loose expression of E Cadherin, the Ecadherin was chosen as an important negative marker for an MIS responsive stem cell marker.

Surprisingly, the inventors herein have discovered that the growth of the population of 3+/Ecad- cells are stimulated by chemotherapeutic agents. Accordingly, current chemotherapeutic agents, such as doxorubicin and cisplatin enrich for these 3+/Ecad- cells. While the inventors have discovered that these 3+/Ecad- cells are enriched by chemotherapeutic agents, they are inhibited by MIS, SP600125, and inhibitors of Lin28, or any combination thereof.

In particular, the inventors demonstrate herein the isolation from multiple ovarian cancer cell lines an ovarian cancer stem cell-enriched population which is 3+/Ecad-, marked by CD44, CD24, and Epcam (3+) and by negative selection for Ecadherin (Ecad-). This 3+/Ecad- ovarian cancer stem cell population comprises less than 1% of ovarian cancer cells and has increased colony formation and shorter tumor-free intervals in vivo after limiting dilution. Surprisingly, the inventors demonstrate that these 3+/Ecad- ovarian cancer stem cells are not only resistant to chemo-ovarian cancer stem cells are not only resistant to chemotherapeutics such as doxorubicin, but also are stimulated by it, as evidenced by the significantly increased number of colonies in treated 3+/Ecad- cells. Similarly, proliferation of the 3+/Ecad- cells in monolayer increased with treatment, by either doxorubicin or cisplatin, compared with the unseparated or cancer stem cell-depleted 3+/Ecad+ cells.

However, the inventors have also discovered that these 3+/Ecad+ cells are sensitive to Mullerian inhibiting substance (MIS), which decreased colony formation. MIS inhibits ovarian cancer cells by inducing G1 arrest of the 3+/Ecad- subpopulation through the induction of cyclin dependent kinase inhibitors. 3+E/cad- cells selectively expressed LIN28, which colocalized by immunofluorescence with the 3+ cancer stem cell markers in the human ovarian carcinoma cell line, OVCAR-5, and is also highly expressed in transgenic murine models of ovarian cancer and in other human ovarian cancer cell lines. Accordingly, converse to current understanding about chemotherapeutics, the inventors have discovered that chemotherapeutics may be stimulative to ovarian cancer stem cells and demonstrate that selective inhibition of the subpopulation of 3+E/cad- ovarian cancer stem cells by treating with MIS, or mimetics thereof or targeting LIN28 should be considered in the development of therapeutics (Meirelles et al, 2012).

Accordingly, this 3+/Ecad- population of ovarian cancer was demonstrated to be more highly enriched than the 3+/Ecad+ population alone for stem/progenitor characteristics and was also resistant to chemotherapeutic agents but sensitive to MIS.

Herein, the inventors also demonstrate that LIN28, a microRNA (miRNA)-binding protein known to regulate expression of cell cycle-related genes and to contribute to cancer stem cell self-renewal and differentiation (17, 18), was the only pluripotency marker among those known to reprogram pluripotency in somatic cells that was increased in these 3+/Ecad- cancer stem cell-enriched population. In addition, LIN28 was demonstrated to also be increasingly expressed in transgenic mouse ovarian cancer models made more aggressive with progressive loss of Misr2 (13). Furthermore, receptor-mediated MIS functional activity correlated with both cell cycle arrest and specific up-regulation of the cyclin-dependent kinase (CDK) inhibitor p15. Accordingly, based on the inventors discovery, it is highly recommended and beneficial to the treatment of ovarian cancer in subjects to test both the stem and the non-stem population in each patient for presence of 3+/Ecad- cells, and thus sensitivity to chemotherapeutic agents and to treat such subjects with biologics such as MIS, or mimetics thereof as the first step in cancer therapy and/or after the bulk of the tumor has been reduced by treatment with chemotherapeutic agents, when planning treatment strategies for ovarian cancer, and optionally also targeting of LIN28 as an alternative or another strategy to improve suppression of this 3+/Ecad- stem cell population.

Accordingly, one aspect of the present invention relates to a method of treating ovarian cancer in a subject, where the method is a two-phase treatment regimen based on identifying if a subject has a subpopulation of 3+/Ecad- ovarian cancer stem cells in the ovarian cancer, and if such 3+/Ecad+ cells are identified, such a subject is treated with one or more or a combination of MIS, a MIS mimetic, or an inhibitor of Lin28 prior to treatment with a chemotherapeutic agent. In such embodiments, a subject can be screened for the presence of 3+/Ecad- cells prior to beginning ovarian cancer therapy, and if a subject is identified to have an ovarian cancer comprising 3+/Ecad- ovarian stem cell population, then the subject is treated with one or more, or a combination of MIS, a MIS mimetic such as SP600125, an inhibitor of Lin28 before beginning treatment with a chemotherapeutic agent such as, for example, cisplatin, doxorubicin (DOX), etc. In some embodiments, after the first phase of treatment of the subject with one or more, or a combination of MIS, a MIS mimetic such as SP600125, and an inhibitor of Lin28, the subject can be re-screened a second time to identify if there is persistence of 3+/Ecad- ovarian cancer stem cells, and if the subject is identified as not to have 3+/Ecad- cells, then the subject is amenable to the second phase of treatment with one or more conventional chemotherapy agents as disclosed herein, for example, but not limited to cisplatin and/or doxiorubicin (DOX).

Accordingly, in some embodiments, the present invention relates to isolating and/or identifying a population of ovarian cancer stem cells in a subject which are CD44+, CD24+, EpCam+ and ECad-, whereby a subject identified to have an ovarian cancer comprising such CD44+, CD24+, EpCam+ ECad- ovarian cancer stem cells is identified to be suitable for treatment with a therapy comprising Mullerian Inhibiting Substance (MIS) or a small molecule MIS mimetic, SP600125, or derivatives thereof.

Another aspect of the present invention relates to an assay to identify a subject with 3+/Ecad− ovarian cancer stem cells. In some embodiments, the present invention relates to an assay for determining the risk of a chemotherapy-resistant ovarian cancer in a subject with ovarian cancer, the assay comprising the steps of: (a) contacting a first biological sample, wherein the first biological sample comprises ovarian cancer cells, ascites, or ovarian cancer biopsy cells obtained from the subject at a first time point, (b) measuring the amount of CD44+/CD24+/Epcam+/Ecad− (3+/Ecad−) cells in the first biological sample, (c) wherein the subject is at risk of a chemotherapy resistant ovarian cancer if there is presence of at least about 0.1% of CD44+/CD24+/Epcam+/Ecad− (3+/Ecad−) cells in the first biological sample. In some embodiments, the assay further comprises the step of (d) wherein the subject is not at risk of a chemotherapy resistant ovarian cancer if there is less than 0.1% 3+/Ecad− cells. In some embodiments, where a subject is identified to have the presence of at least 0.1% CD44+/CD24+/Epcam+/Ecad− (3+/Ecad−) cells, the subject is administered a composition comprising one or more, or a combination of MIS or a small molecule MIS mimetic, SP600125, or derivatives thereof, or inhibitors of Lin28. In some embodiments, where a subject is identified not to have the presence of CD44+/CD24+/Epcam+/Ecad− (3+/Ecad−) cells (e.g., has 3+/Ecad+ ovarian cancer cells), the subject is administered a composition comprising chemotherapeutic agents. In such embodiments, the assay can be performed on a biological sample obtained from the subject at a first time point, e.g., before beginning an ovarian cancer treatment regimen, and/or at another time point, e.g., during a treatment regimen (e.g., after treatment with MIS, or mimetic thereof) to monitor the presence or absence of 3+/Ecad− cells, and/or at a time point before beginning the administration of a chemotherapeutic agent to the subject. In some embodiments, performing the assay before beginning administration of a chemotherapeutic agent is useful to ensure absence of 3+/Ecad− ovarian cancer stem cells which can be stimulated and enriched by the chemotherapeutic agent.

The inventors have herein discovered that an ovarian cancer stem cell population which is CD44+, CD24+, EpCam+ and ECad− contributes to, or is responsible for drug resistance in human ovarian cancer, and that combinations of chemotherapeutic agents with MIS or SP600125 may be effective adjuvant therapies in controlling total tumor growth.

Accordingly, in some embodiments, a subject identified to have an ovarian cancer comprising CD44+, CD24+, EpCam+ ECad− ovarian cancer stem cells is identified to have an ovarian cancer which is resistant to traditional chemotherapeutic agents, e.g., such as but not limited to cisplatin, deoxyrubicin, taxol, paclitaxel and the like. In some embodiments, a subject identified to have an ovarian cancer comprising CD44+, CD24+, EpCam+ ECad− ovarian cancer stem cells is identified as having a recurrent cancer.

In the present study, the inventors performed flow cytometry and Fluorescent Activated Cell Sorting (FACS) to identify a more highly enriched stem/progenitor cell population in human primary ascites cells taken from patients with ovarian cancer. The inventors examined the contribution of E-cadherin to stem/progenitor selection since its loss has been reported to lead to epithelial to mesenchymal transformation during progressive tumorigenesis in breast cancer (Weinberg et al.) and since the surface epithelium of the ovary, which expresses the MIS receptor Type II (MIS RII) and is normally characterized by both epithelial and mesenchymal expression (Szotek et al, 2008; Zhan et al, 2006; Masiakos et al, 1999), becomes predominantly mesenchymal as tumor initiation occurs. Combined with E-cadherin negative selection (Ecad−), the inventors demonstrate increased cancer stem/progenitor characteristics and MIS responsiveness in the isolated ascites cells. The inventors also demonstrated that MIS action is receptor mediated resulting in phosphorylation of SMAD 1/5/8 which results in cell cycle arrest and upregulation of the cell cycle inhibitor p16, which correlates with downregulation of LIN28, an RNA binding protein regulator belonging to the microRNA (miR) family of Let7's (Gupta et al, 2009).

The inventors also demonstrate that these drug-resistant CD44+, CD24+, EpCam+ and ECad− (3+/Ecad−) cells remain as a therapy-evading cells and lead to recurrence in ovarian cancer, and were discovered to be more tumorigenic in animals than ovarian cancer cells that are drug-sensitive. MIS by normally functioning on the surface epithelium of the ovary and in the Fallopian tube as a potent tumor suppressor may be such a novel therapy by targeting ovarian cancer stem/progenitor cell populations.

Furthermore, this select population of CD44+, CD24+, EpCam+ and ECad− ovarian cancer cell lines was demonstrated to have increased colony and tumor forming properties, and also had an increased expression of the pluripotency factor Lin28 as determined by quantitative PCR, both in vitro and when injected in vivo, as was observed in the transgenic animals with aggressive compared to indolent tumors.

Accordingly, in one embodiment the present invention is related to methods to identify and enrich for a population of CD44+, CD24+, EpCam+ and ECad− (e.g., 3+/Ecad− cells) ovarian stem cells.

Another embodiment of the present invention is related to methods to identify and enrich for a population of CD44+, CD24+, EpCam+ and ECad− (e.g., 3+/Ecad− cells) ovarian cancer stem cells.

Another embodiment of the present invention is related to methods to screen for agents that inhibit the growth and/or kill CD44+, CD24+, EpCam+ and ECad− (e.g., 3+/Ecad− cells) ovarian cancer stem cells as compared to 3+/Ecad+ cells or non-stem ovarian cancer cells.

In another embodiment, the present invention relates to methods for the treatment of ovarian cancer by targeting CD44+, CD24+, EpCam+ and ECad− (e.g., 3+/Ecad− cells) ovarian cancer stem cells. In such embodiments, a method to prevent and/or treat a subject with ovarian cancer is provided, where the subject is identified to have ovarian cancer comprising CD44+, CD24+, EpCam+ and ECad− (e.g., 3+/Ecad− cells) ovarian cancer stem cells, and the subject is administered a pharmaceutical composition comprising MIS or a derivative, fragment, analogue or homologue thereof. In some embodiments, the subject is also administered additional cancer therapies, for example chemotherapies, radiotherapy, immune therapy and other agent.

In another aspect of the invention, methods to treat ovarian cancers by targeting cancer stem cells are disclosed, the method comprising targeting the CD44+, CD24+, EpCam+ and ECad− (e.g., 3+/Ecad− cells) ovarian cancer stem cells with agents that are agonists to the MIS receptor type II (MISRII). Examples of agonists of MISRII are MIS protein and derivatives and variants thereof. Other agonists of MISRII are MIS mimetics, for example pyrazoloanthrone and derivatives thereof.

In some embodiments, the methods of the present invention relate to the treatment of ovarian cancers by targeting ovarian cancer stem cells, the method comprising administering a pharmaceutical composition comprising MIS or derivatives or analogues thereof to the subject identified to have ovarian cancer comprising CD44+, CD24+, EpCam+ and ECad− (e.g., 3+/Ecad− cells) ovarian cancer stem cells. In some embodiments, the pharmaceutical composition administered to the subject comprises additional therapies, for example agents that function chemotherapeutic agents.

In one aspect of the invention, the present invention relates to methods to prevent and/or treat a subject with ovarian cancer, wherein the method comprises the steps (i) of identifying the presence of CD44+, CD24+, EpCam+ and ECad− (e.g., 3+/Ecad− cells) ovarian cancer stem cells in a subject using the methods as disclosed herein, and wherein if the subject is identified to have ovarian cancer comprising CD44+, CD24+, EpCam+ and ECad− (e.g., 3+/Ecad− cells) ovarian cancer stem cells, the subject is administered a pharmaceutical composition comprising MIS or a derivative, homologue, analogue or fragment thereof.

As a non-limiting example, pharmaceutical compositions comprising at least one agent that activates MISRII can be administered to a subject with ovarian cancer comprising CD44+, CD24+, EpCam+ and ECad− (e.g., 3+/Ecad− cells) ovarian cancer stem cells in an effective amount for the treatment of ovarian cancer, wherein the ovarian cancer comprises CD44+, CD24+, EpCam+ and ECad− (e.g., 3+/Ecad− cells) ovarian cancer stem cells.

In another embodiment, methods for diagnosing a subject at risk of having a recurrent ovarian cancer are disclosed. In some embodiments, the methods comprise assessing the presence of CD44+, CD24+, EpCam+ and ECad− (e.g., 3+/Ecad− cells) ovarian cancer stem cells in a subject as disclosed herein, for example assessing a biological sample obtained from the subject for (i) positive expression of CD44+, CD24+, EpCam+ and (ii) negative expression of ECad−, wherein if the biological sample comprises CD44+, CD24+, EpCam+ and ECad− (e.g., 3+/Ecad− cells) ovarian cancer stem cells, the subject is identified as being at risk of a recurrent ovarian cancer. In some embodiments, the biological sample is from a biopsy. In some embodiments, the biological sample is primary ascites.

In some embodiments, the present invention provides a method for identifying and isolating CD44+, CD24+, EpCam+ and ECad− (e.g., 3+/Ecad− cells) ovarian cancer stem cells which comprises contacting a population of ovarian cells with agents which bind to CD44, CD24, EpCam, and separating and selecting cells which are positive for CD44, CD24, EpCam, and then further negatively selecting from these CD44+, CD24+, EpCam+ cells which are Ecad− cells (e.g., separate the ECad+ and ECad− cells, and select the ECad− cells), where the cells that are CD44+, CD24+, EpCam+ and ECad− (e.g., 3+/Ecad− cells) ovarian cancer stem cells identify ovarian cancer stem cells and can be isolated.

In some embodiments, agents that are reactive to CD44, CD24, EpCam and ECad can be any binding agent or any agent which binds to, and can be used to identify the nucleic acid encoding CD44, CD24, EpCam and ECad respectively and/or agents which bind to, and can be used to identify proteins of CD44, CD24, EpCam and ECad respectively. In some embodiments, the agent is a nucleic acid, nucleic acid analogue, protein or fragment thereof. In some embodiments, the agent is further labeled with a detectable marker, for example a fluorescent marker, or a label that can be used to isolate the agent that is associated. Such a label is, for example but not limited to metallic beads and streptavidin. In some embodiments, an agent that is reactive to CD44, CD24, EpCam and ECad can be any binding agent or any agent which is a protein or polypeptide, for example but not limited to an antibody with binding affinity for CD44, CD24, EpCam and ECad, or fragment thereof, for example an anti-CD44 antibody, an anti-CD24 antibody, an anti-EpCam antibody, and an anti-ECad antibody. In some embodiments, a protein agent is a protein binding-partner to CD44, CD24, EpCam and ECad or a fragment thereof, for example a ligand or co-factor to CD44, CD24, EpCam and ECad.

In another aspect, the present invention provides methods for identifying and isolating CD44+, CD24+, EpCam+ and ECad− (e.g., 3+/Ecad− cells) ovarian cancer stem cells comprising contacting a population of ovarian cells with antibodies with binding affinity for CD44, CD24, EpCam and ECad and separating cells that are CD44−, CD24−, EpCam− from those which are CD44+, CD24+, EpCam+ (e.g., 3+ cells) and then further separating the 3+ cells into ECad− and ECad+ cells, and selecting the 3+/Ecad− cells from the 3+/ECad+ cells, where the 3+/Ecad− cells are identified as ovarian cancer stem cells and can be isolated. In some embodiments, one can identify and isolate CD44+, CD24+, EpCam+ and ECad− (e.g., 3+/Ecad− cells) using any method known to ordinary skill in the art.

Method to isolate and separate the CD44+, CD24+, EpCam+ and ECad− (e.g., 3+/Ecad− cells) ovarian cancer stem cells as disclosed herein are well known in the art and can include, for example separation methods such as, but are not limited to fluorescence cell sorting (FACS), flurometry, flow cytometry, or microscopy techniques.

In some embodiments, the CD44+, CD24+, EpCam+ and ECad− ovarian cancer stem cells are identified in a population of ovarian cancer cells, for example a population of ovarian cancer cells present in a biological sample. Such biological samples may be a tissue sample, for example a tumor tissue sample or biopsy tissue sample, for example a biopsy of a cancer or tumor, for example ovarian cancer biopsy. In some embodiments, the tissue sample is obtained from a subject, for example a mammalian, for example but not limited to a human subject.

In some embodiments, the population of CD44+, CD24+, EpCam+ and ECad− (3+/Ecad−) ovarian cancer cell is isolated from a population of ovarian cancer cells, ovarian cancer cells, vulvar epidermal carcinoma cells, cervical carcinoma cells, endometrial edenocarinaoma cells and ovarian adenocarcinoma cells. In alternative embodiments, the population of CD44+, CD24+, EpCam+ and ECad− (3+/Ecad−) ovarian cells isolated from a population of primary ascite cells, and in some embodiments, the population of CD44+, CD24+, EpCam+ and ECad− (3+/Ecad−) ovarian cells can be isolated from a population of ovarian cancer cell line cells, for example human or rodent ovarian cancer cell lines. Examples of human and mouse ovarian cancer cells are well known by person skilled in the art, for example, human ovarian cancer cells can include but are not limited to IGROV-1, SKOV3, OVCAR-5,8, or 3 human cancer cell lines. Examples of mouse ovarian cancer cell lines include, for example but are not limited to MOVCAR7 or 8 or 4306 ovarian cancer cell lines.

In some embodiments, the CD44+, CD24+, EpCam+ and ECad− (e.g., 3+/Ecad− cells) ovarian cancer stem cells as disclosed herein are further characterized. Such further characterization includes assessment of multi-drug resistance sensitivity, for example the CD44+, CD24+, EpCam+ and ECad− (e.g., 3+/Ecad− cells) ovarian cancer stem cells as disclosed herein were discovered to have multi-drug resistance.

Another aspect of the present invention relates to methods to treating ovarian cancer in a subject by targeting CD44+, CD24+, EpCam+ and ECad− (e.g., 3+/Ecad− cells) ovarian cancer stem cells. In such an embodiment, a method for treating a subject with ovarian cancer comprising administering to the subject an effective amount of MIS or a homologue or variant or derivative thereof, wherein the subject is identified to have an ovarian cancer comprising CD44+, CD24+, EpCam+ and ECad− (e.g., 3+/Ecad− cells) ovarian cancer stem cells. In some embodiments, the subject has recurrent ovarian cancer.

In some embodiments, the MIS is a functional derivative, analogue or variant thereof. For example, a functional derivative of MIS is a pyrazoloanthrone or derivative or analogue thereof. In some embodiments, a functional derivative of MIS is SP600125, which is disclosed in U.S. application Ser. No. 13,328,387, which is incorporated herein in its entirety by reference. In alternative embodiments, the MIS is recombinant human MIS. In some embodiments, the effective amount of MIS is an effective amount of a pharmaceutical composition comprising MIS or a variant or derivative thereof. In some embodiments, the pharmaceutical composition further comprises a pharmaceutically acceptable carrier. In additional embodiments, the pharmaceutical composition optionally further comprises a chemotherapeutic agent or an inhibitor of BCRP1.

In further embodiments, MIS can further comprise a targeting moiety, for example a targeting moiety where the targeting moiety targets CD44+, CD24+, EpCam+ and ECad− (e.g., 3+/Ecad− cells). As a non-limiting example, such a targeting moiety useful in the methods of the present invention is a binding partner to CD44, and/or CD24, and/or EpCam, for example a protein ligand to CD44, and/or CD24, and/or EpCam and/or a co-factor of CD44, and/or CD24, and/or EpCam.

In some embodiments, the administration of MIS is administered more than once, and in further embodiments, the MIS or derivative thereof is administered before, after or at the same time as the additional therapy.

In some embodiments, the subject is further administered one or more additional therapies, for example but not limited to chemotherapy, radiotherapy, thermotherapy, immunotherapy, hormone therapy, laser therapy and surgery. In alternative embodiments, the chemotherapy is selected from chemotherapeutic agents, for example but not limited to paclitaxel, cisplatin, doxorubicin, or analogues thereof.

In some embodiments, the pharmaceutical composition comprising MIS, and optionally comprising additional agents is administered to the subject via intravenous, intradermal, intramuscular, intraarterial, intralesional, percutaneous, subcutaneous, intratumoral, or by aerosol routes. In some embodiments, the subject is administered prophylactic administration and/or therapeutic administration.

In some embodiments, the subject to be treated is a mammal, for example a human. In some instances, the subject undergone one or more cancer therapies, for example but not limited to cancer therapies such as surgery, chemotherapy, radiotherapy, thermotherapy, immunotherapy, hormone therapy and laser therapy.

In another aspect of the present invention, methods to determine if a subject is at risk of having a recurrent ovarian cancer are provided, comprising assessing the presence of CD44+, CD24+, EpCam+ and ECad− (e.g., 3+/Ecad− cells) ovarian cancer stem cells in a biological sample from the subject, where if the biological sample comprises CD44+, CD24+, EpCam+ and ECad− (e.g., 3+/Ecad− cells) ovarian cancer stem cells, the subject is identified as being at risk of having a metastasis or recurrent ovarian cancer.

In another aspect of the present invention relates to a method to identify agents that reduce the self-renewal capacity of a population of CD44+, CD24+, EpCam+ and ECad− (e.g., 3+/Ecad− cells) ovarian cancer stem, comprising contacting a population of CD44+, CD24+, EpCam+ and ECad− (e.g., 3+/Ecad− cells) ovarian cancer stem cells with an agent, and measuring the proliferation of the population of CD44+, CD24+, EpCam+ and ECad− (e.g., 3+/Ecad− cells), whereby an agent that decreases the proliferation as compared to a reference agent or absence of an agent identifies an agent that inhibits the self-renewal capacity of the CD44+, CD24+, EpCam+ and ECad− (e.g., 3+/Ecad− cells) ovarian cancer stem cell. In such embodiments, the agent is any agent, for example but not limited to nucleic acids, nucleic acid analogues, small molecule, proteins, aptamers, ribosomes etc. Proliferation assays useful in the methods are commonly known by persons of ordinary skill in the art, for example but not limited to the methytiazoletetrazolium (MTT) proliferation assay, colony formation assay according to the methods as disclosed herein in the Examples.

In another aspect of the present invention, methods of treating a subject affected with cancer are also provided, the method comprising assessing the presence of CD44+, CD24+, EpCam+ and ECad− (e.g., 3+/Ecad− cells) ovarian cancer stem cells in a biological sample obtained from the subject, wherein a clinician reviews the results and if the results indicate the presence of CD44+, CD24+, EpCam+ and ECad− (e.g., 3+/Ecad− cells) ovarian cancer stem cells in the biological sample, the clinician directs the subject to be treated with an effective amount of a pharmaceutical composition comprising MIS or a homologue or variant or derivative thereof.

Another aspect of the present invention relates to methods to determine if a subject is at risk of having a recurrent ovarian cancer, the method comprising assessing the presence of CD44+, CD24+, EpCam+ and ECad− (e.g., 3+/Ecad− cells) ovarian cancer stem cells by the methods as disclosed herein, and if the biological sample is identified to comprise CD44+, CD24+, EpCam+ and ECad− (e.g., 3+/Ecad− cells) ovarian cancer stem cells, the subject is at risk of having a metastasis or recurrent ovarian cancer. In such embodiments, the subject can be administered an anti-cancer agent or therapy such as administration of MIS or an analogue or derivative thereof according to the methods as disclosed herein, or any other cancer therapy known by a person of ordinary skill in the art.

Another aspect of the present invention relates to methods for identifying and/or isolating and/or enriching for a population of CD44+, CD24+, EpCam+ and ECad− (e.g., 3+/Ecad− cells) ovarian stem cells, the method comprising contacting a population of cells comprising ovarian cells with agents reactive to CD44, CD24 and EpCam and separating reactive positive cells from non-reactive cells, wherein the reactive positive cells are then further separated into ECad+ and ECad− cells, wherein the CD44+, CD24+, EpCam+ and ECad− ovarian cancer stem cells are collected and isolated.

In some embodiments, the present invention further provides a method to identify agents that reduce the self-renewal capacity of an ovarian cancer stem cell, comprising contacting a CD44+, CD24+, EpCam+ and ECad− (e.g., 3+/Ecad− cells) ovarian cancer stem cell as identified according the methods as disclosed herein with an agent, and measuring the proliferation of the CD44+, CD24+, EpCam+ and ECad− ovarian cancer cell, whereby an agent that decreases the proliferation as compared to a reference agent or absence of an agent identifies an agent that inhibits the self-renewal capacity of the ovarian cancer stem cell.

In another embodiment, the present invention further provides a method for identifying agents which kill or decrease the rate of proliferation of ovarian cancer stem cells, the method comprising: (a) culturing a population of CD44+, CD24+, EpCam+ and ECad− ovarian cancer stem cells as identified according to the methods as disclosed herein, (b) culturing a population of somatic ovarian stem cells as identified according to the methods as disclosed herein, (c) adding to the media of the population of CD44+, CD24+, EpCam+ and ECad− ovarian cancer stem cells one or more agents and adding to the media of the population of somatic ovarian stem cells one or more of the same agents; (d) measuring the rate of proliferation of the population of CD44+, CD24+, EpCam+ and ECad− (3+/Ecad−) ovarian cancer stem cells and measuring the rate of proliferation of the population of somatic ovarian stem cells and/or measuring the rate of proliferation of a population of CD44+/CD24+/Epcam+/Ecad+(3+/Ecad+) cells; ((e) ????? comparing the rate of proliferation of the population of CD44+, CD24+, EpCam+ and ECad− (3+/Ecad−) ovarian cancer stem cells with rate of proliferation of the population of somatic ovarian stem cells and or population of 3+/Ecad+ cells, wherein an agent which decreases the rate of proliferation of the CD44+, CD24+, EpCam+ and ECad− (e.g., 3+/Ecad− cells) ovarian cancer stem cells as compared to the rate of proliferation of somatic ovarian stem cells or 3+/Ecad+ cells identifies an agent that kills or decreases the rate of proliferation of an ovarian cancer stem cell). In some embodiments, agents used in the methods to identify agents that kill or decrease the rate of proliferation of an ovarian cancer stem cell, such an agent is a nucleic acid, nucleic acid analogue, small molecule, protein, peptiomimetic, antibody, peptide, aptamer, ribozyme, and variants and fragments thereof. Further, proliferation assays useful in identifying agents that kill or decrease the rate of proliferation of an ovarian cancer stem cell are the methytiazoletetrazolium (MTT) proliferation assay or the colony forming unit (CFU) assay, as disclosed herein.

Accordingly, one aspect of the present invention provides a method to identify an ovarian cancer stem cell in a population of cells, comprising measuring the expression product of CD24, CD44, EpCam and E-Cadherin, wherein if a cell is positive for the expression of CD24, CD44, EpCam and negative for the expression of E-Cadherin, the cell is identified as an ovarian cancer stem cell.

Another aspect of the present invention relates to a method to isolate a population of ovarian cancer stem cells in a population of cells, comprising: (i) measuring the expression product of CD24, CD44, EpCam, and selecting the cells which are positive for expression of CD24, CD44, EpCam, and (ii) measuring the expression product of E-Cadherin in the selected cells and selecting for the cells which are negative for the expression of E-Cadherin, wherein the selected cells which are positive for the expression of CD24, CD44, EpCam and negative for the expression of E-Cadherin are an isolated population of ovarian cancer stem cells. In some embodiments, the steps can be performed in any order. In some embodiments, the ovarian cancer stem cells are responsive to MIS inhibition. In some embodiments, the ovarian cancer stem cells are resistant to chemotherapeutic agents, e.g., chemotherapeutic agents selected from the group, but not limited to Dexorubicin, taxol, cisplatin, paclitaxel and derivatives thereof.

Another aspect of the present invention relates to an assay for detecting the presence of ovarian cancer stem cells in a biological sample, the assay comprising: (a) transforming the expression product of CD24, CD44, EpCam and E-Cadherin in a biological sample into detectable targets; (b) measuring the level of the detectable targets; wherein the positive expression of CD24, CD44, EpCam and the negative expression of E-Cadherin indicates the presence of ovarian cancer stem cells in a biological sample.

Another aspect of the present invention relates to a method to identify a recurrent ovarian cancer in a subject, comprising measuring the expression product of CD24, CD44, EpCam and E-Cadherin in a biological sample obtained from the subject, wherein if the biological sample is positive for the expression of CD24, CD44, EpCam and negative for the expression of E-Cadherin, the subject is identified as being at risk of having a recurrent ovarian cancer. In some embodiments, such a method further comprises administering to the subject identified at being at risk of recurrent cancer a Mullerian Inhibiting Substance (MIS) therapeutic, or a mimetic or analogue thereof. In some embodiments, MIS is human recombinant MIS (hrMIS) or a pro-hormone or homodimer thereof. In some embodiments, a mimetic of MIS is SP600125 or a derivative thereof. In some embodiments, the subject is a mammalian subject, e.g., a human subject.

Another aspect of the present invention relates to a method of determining if a subject has an ovarian cancer which is resistant to chemotherapeutic treatment, comprising: (a) selecting a subject with ovarian cancer, and (b) measuring the expression products of CD24, CD44, EpCam and E-Cadherin in a biological sample obtained from the subject, wherein if the biological sample is positive for the expression of CD24, CD44, EpCam and negative for the expression of E-Cadherin, the subject is identified as having a having a ovarian cancer which is resistant to chemotherapeutic treatment.

Another aspect of the present invention relates to an isolated population of ovarian cancer stem cells, wherein the ovarian cancer stem cells are positive for the expression of CD24, CD44, EpCam and negative for the expression of E-Cadherin. In some embodiments, the ovarian cancer stem cell is also positive for the expression of Lin28. In some embodiments, the ovarian cancer stem cells are mammalian ovarian cancer stem cells, e.g., human ovarian cancer stem cells.

Another aspect of the present invention relates to the use of the isolated population of CD44+. CD24+, EpCam+ and E-Cadherin− ovarian cancer stem cells in an assay to identify an agent which inhibits the proliferation of the population of cells, comprising; (a) contacting the isolated population of CD44+. CD24+, EpCam+ and E-Cadherin− cells with at least one agent; and (b) measuring the proliferation of the population of cells in the presence and absence of the agent, wherein a decrease in the proliferation in the population of cells in the presence of the agent as compared to the absence, identifies an agent which inhibits the proliferation of ovarian cancer stem cells. In some embodiments, the proliferation is measured by colony formation assay or MTT assay as disclosed herein.

In further aspect, the present invention provides a method of treating a subject affected with cancer, the method comprising assessing the presence of CD44+, CD24+, EpCam+ and ECad− (e.g., 3+/Ecad− cells) ovarian cancer stem cells in a biological sample obtained from the subject, wherein a clinician reviews the results and if the results indicate the presence of CD44+, CD24+, EpCam+ and ECad− (e.g., 3+/Ecad− cells) ovarian cancer stem cells in the biological sample, the clinician directs the subject to be treated with an effective amount of a pharmaceutical composition comprising MIS or a homologue or variant or derivative thereof. In some embodiments, the biological sample is a tissue sample, for example a tissue sample such as a cancer or a tumor, and/or a biopsy tissue sample. In some embodiments, the tissue sample comprises ovarian cancer cells, vulvar epidermal carcinoma cells, cervical carcinoma cells, endometrial adenocarinaoma cells and ovarian adenocarcinoma cells. In a particular embodiment, the tissue sample comprises ascite cells.

In some embodiments, where agent is used to identify and/or enrich for a population of CD44+, CD24+, EpCam+ and ECad− (e.g., 3+/Ecad− cells) ovarian cancer stem cells, the agent can be a nucleic acid or protein or analogues or fragments thereof. For example, an agent can be reactive to an expression product, for example protein and/or gene transcript such as mRNA, or fragments of an expression product, encoded by genes CD44, CD24, EpCam, E-cadherin. In some embodiment, the gene transcript is selected from the group consisting of RNA, messenger RNA, or genomic DNA. In some embodiments, a nucleic acid agent is DNA, RNA or nucleic acid analogues, such as PNA (peptide nucleic acid), pc-PNA (pseudo-complementary PNA), LNA (locked nucleic acid) and analogues and derivatives thereof. In some embodiments, a protein agent useful in the methods as disclosed herein is an antibody or antibody fragment thereof. In further embodiments, an agent reactive to the genes to identify somatic ovarian stem cell population and/or an ovarian cancer stem cell populations are small molecule agents or aptamer agents or antibody fragment agents.

In some embodiments, the present invention relates to a method to identify a ovarian cancer stem cell in a population of cells, comprising measuring the expression of CD24, CD44, EpCam and E-Cadherin in a cell, wherein if a cell is positive for the expression of CD24, CD44, EpCam and negative for the expression of E-Cadherin, the cell is identified as an ovarian cancer stem cell.

Another aspect of the present invention relates to a method to isolate a population of ovarian cancer stem cells in a population of cells, comprising: (a) measuring the expression of CD24, CD44, EpCam in a cell, and selecting the cells which are positive for expression of CD24, CD44, EpCam, and (b) measuring the expression product of E-Cadherin in the selected cells and selecting for the cells which are negative for the expression of E-Cadherin, and selecting for cells which are positive for the expression of CD24, CD44, EpCam and negative for the expression of E-Cadherin which are an isolated a subpopulation of ovarian cancer stem cells. In some embodiments, such CD44+/CD24+/EpCam+/Ecad− (3+/Ecad−) ovarian cancer stem cells are responsive to inhibition of proliferation by MIS or a mimetic thereof. In some embodiments, the CD44+/CD24+/EpCam+/Ecad− (3+/Ecad−) ovarian cancer stem cells are resistant to chemotherapeutic agents, such as, but not limited to, dexorubicin, taxol, cisplatin, paclitaxel and derivatives thereof.

In some embodiments, the population of CD44+/CD24+/EpCam+/Ecad− (3+/Ecad−) ovarian cancer stem cells are isolated or enriched from a biological sample, such as, for example, but not limited to ovarian cells, ascites, ovarian cell line, ovarian cancer biopsy sample.

Another aspect of the present invention relates to an assay for detecting the presence of ovarian cancer stem cells in a biological sample, the assay comprising: (a) transforming the expression of CD24, CD44, EpCam and E-Cadherin in ovarian cells in a biological sample into detectable targets; (b) measuring the level of the detectable targets; wherein the presence of detectable targets for CD24, CD44, EpCam and the absence of detectable targets for E-Cadherin in indicates the presence of ovarian cancer stem cells in a biological sample. In some embodiments, transforming can be any method known in the art to detect an expression product (e.g., mRNA or protein) in a cell. For example, but by no way a limitation, one method to transform the expression products of CD24, CD44, EpCam and/or E-Cad in a cell is to attach an antibody with a direct or indirect detectable signal to the proteins of CD24, CD44, EpCam and/or E-Cad. Another method to transform the expression product of CD44. CD24, EpCam and/or E-cad is to hybridize a nucleic acid probe with a direct or indirect detectable signal to the mRNA of CD24, CD44, EpCam and/or E-Cad.

Another aspect of the present invention relates to an assay comprising: (a) contacting a biological sample from a subject with at least one detectable antibody specific to CD44, CD24, EpCam and Ecadherin; (b) washing the sample to remove unbound antibodies, (c) measuring the intensity of the signal from the bound, detectable antibody to CD44, CD24, EpCam and E-cadherin, (d) comparing the measured intensity of the signal of CD44, CD24, EpCam and Ecadherin to a reference value for each of CD44, CD24, EpCam and Ecadherin levels of expression, and if there is a measured intensity of CD44, CD24, EpCam is at or increased relative to a reference value for each of CD44, CD24, EpCam expression levels, or if the measured intensity of ECad is below a reference value for ECad expression and (e) identifying the subject has having increased probability of having chemotherapeutic resistant ovarian cancer.

Another aspect of the present invention relates to an assay comprising: (a) contacting a biological sample from a subject with at least one detectable antibody specific to CD44, CD24, and EpCam, (b) washing the sample to remove unbound antibodies, (c) selecting for cells where the intensity of the signal from the bound, detectable antibody to CD44, CD24, EpCam is at or above a reference level for each of CD44, CD24. EpCam respectively, (d) contacting the cells from step (c) with a detectable antibody specific to Ecadherin, (e) washing the sample to remove unbound antibodies, (f) selecting for cells where the intensity of the signal from the bound, detectable antibody to Ecadherin is below a reference level for Ecad expression level, (g) identifying the subject has having increased probability of having chemotherapeutic resistant ovarian cancer where the cells selected have the intensity of Ecadherin below a reference level for Ecadherein.

For example, in some embodiments of all aspects of the present invention, the expression of CD44, CD24, EpCam can be compared to a reference level, where the reference level is the level of expression of CD44, CD24, EpCam for a population of cells where there is presence of CD44, CD24, EpCam protein or mRNA. For example, in some embodiments of all aspects of the present invention, the expression of CD44, CD24, EpCam can be compared to a reference level, where the reference level is the level of expression of CD44, CD24, EpCam for a population of cells where there is positive expression (e.g., the presence) of CD44, CD24, EpCam protein or mRNA. In some embodiments of all aspects of the present invention, the expression of ECad can be compared to a reference level, where the reference level is the level of expression of ECad for a population of cells where there is positive expression (e.g., the presence) of Ecad protein or mRNA.

In all aspects of the present invention, the assays can be performed in an automated, high-throughput manner, for example, using a robotic system.

Another aspect of the present invention relates to a method of treating a subject with ovarian cancer comprising administering a pharmaceutically effective amount of MIS or a MIS mimetic, e.g., SP600125 to the subject having ovarian cancer, wherein the ovarian cancer is determined to comprise a population of the CD44+/CD24+/EpCam+/Ecad− cells, and wherein the subject is not administered an effective amount of a chemotherapeutic agent if said subject is determined to have CD44+/CD24+/EpCam+/ECad− cells.

In some embodiments of all aspects disclosed herein, MIS is recombinant human MIS (rhMIS) or a pro-hormone or homodimer thereof. In some embodiments of all aspects disclosed herein, a MIS mimetic is SP600125 or a derivative thereof. In some embodiments of all aspects disclosed herein, a subject is a mammalian subject, such as a human subject.

Another aspect of the present invention relates to a method of determining if a subject is responsive to MIS or a MIS mimetic comprising assaying a biological sample from the subject for the presence of CD44+/CD24+/Epcam+/Ecad− cells, wherein MIS or a MIS mimetic is administered to a subject if CD44+/CD24+/EpCam+/Ecad− cells are present, and administering to the subject a chemotherapeutic agent if CD44+/CD24+/EpCam+/ECad− cells are absent.

Another aspect of the present invention relates to a method to determine if a subject with ovarian cancer can be treated with a chemotherapeutic, the method comprising assaying a biological sample from the subject for the presence of CD44+/CD24+/Epcam+/Ecad− cells, wherein administering to the subject a chemotherapeutic agent if CD44+/CD24+/EpCam+/ECad− cells are absent.

Another aspect of the present invention relates to a method of determining if a subject with ovarian cancer has an increased probability of being resistant to chemotherapeutics, comprising assaying a biological sample from the subject for the presence of CD44+/CD24+/Epcam+/Ecad− cells, the presence of CD44+/CD24+/EpCam+/ECad− cells indicates the subject has increased probability of being resistant to chemotherapeutics.

Another aspect of the present invention relates to an isolated population of ovarian cancer stem cells, wherein the ovarian cancer stem cells are positive for the expression of CD24, CD44, EpCam and negative for the expression of E-Cadherin. In some embodiments, the CD24+/CD44+/EpCam+/Ecad− ovarian cancer stem cells are further positive for the expression of Lin28. In some embodiments, the CD24+/CD44+/EpCam+/Ecad− ovarian cancer stem cells are mammalian ovarian cancer stem cells, such as human CD24+/CD44+/EpCam+/Ecad− ovarian cancer stem cells.

Another aspect of the present invention relates to the use of the isolated population of CD44+/CD24+/EpCam+/ECad− ovarian cancer stem cells in an assay to identify an agent which inhibits the proliferation of said CD44+/CD24+/EpCam+/ECad− ovarian cancer stem cells population of cells, comprising; (a) contacting the isolated population of CD44+/CD24+/EpCam+/ECad− ovarian cancer stem cells with at least one agent; and (b) measuring the proliferation of the population of CD44+/CD24+/EpCam+/ECad− ovarian cancer stem cells in the presence and absence of the agent, wherein an decrease in the proliferation in the population of cells in the presence of the agent as compared to the absence, identifies an agent which inhibits the proliferation of ovarian cancer stem cells. In some embodiments, cell proliferation can be measured by colony formation assay.

In some embodiments, the CD24+/CD44+/EpCam+/Ecad− cell population can be used in assays to screen for ovarian cancer therapeutics. Another aspect of the present invention relates to a method for screening potential ovarian cancer therapeutics which comprises: (a) growing CD44+/CD24+/EpCam+/ECad− ovarian cancer stem cells in the presence of a compound suspected as being a chemotherapeutic, (b) growing said CD44+/CD24+/EpCam+/ECad− ovarian cancer stem cell in the absence of said compound, (c) determining the rate of growth of said CD44+/CD24+/EpCam+/ECad− cells in the presence of said compound and the rate of said CD44+/CD24+/EpCam+/ECad− ovarian cancer cells in the absence of said compound, and (d) comparing the growth rate of said CD44+/CD24+/EpCam+/ECad− cells, wherein a slower rate of growth of said CD44+/CD24+/EpCam+/ECad− cell in the presence of said compound is indicative of a ovarian cancer therapeutic.

A further embodiment of the present invention relates to kits to identify or enrich for a population of CD44+, CD24+, EpCam+ and ECad− (e.g., 3+/Ecad− cells) ovarian cancer stem cells in a biological sample, the kit comprising agents reactive to CD44, CD24, EpCam, ECad and can optionally further comprise agents reactive to Lin28. In some embodiments, the kits comprise agent that are nucleic acid agents, nucleic acid analogue agents or protein agents or fragments or analogues thereof. In some embodiments, the protein agents are antibody, anitmer, aptamer or fragments thereof, and in some embodiments, the kits can be in the form of ELISAs and/or protein chip array formats. In alternative embodiments, where the agent is a nucleic acid agent, the kit can be in the format of, for example a microarray chip or nucleic acid binding chip. In some embodiments, the kits as disclosed herein can be used for isolation of the ovarian stem cell of interest.

BRIEF DESCRIPTION OF FIGURES

This patent or application file contains at least one drawing executed in color. Copies of this patent or patent application publication with color drawing(s) will be provided by the Office upon request and payment of the necessary fee.

FIG. 1A shows colonies of CD44/CD24/Epcam triple positive (3+/Ecad+) and 3+/Ecad− cells isolated from SKOV-3 human ovarian cancer cell line by FACS which were plated at 500, 1000, and 2000 cells. FIG. 1B shows quantification of results of growth of 3+/Ecad− and 3−Ecad+ cells isolated from OVCAR-5 human ovarian cancer cell line by FACS which were plated at 100,000, 50,000, and 25,000 cells in 12-well plates coated by metrigel. After incubation for 14 days at 37° C., colonies were stained (FIG. 1A) and counted (FIG. 1B). CD44/CD24/Epcam triple positive with loss of Ecadherin (3+/Ecad−) (FIG. 1A) formed more colonies than triple negative with Ecadherin (3−Ecad+) (FIG. 1B). FIG. 1C shows 3+/Ecad− and 3+/Ecad+ cells isolated from primary ascites from ovarian cancer patients were plated at 50,000 cells in low-melting agarose in 12-well plates and incubated for 2-3 wk, and then colonies were counted. 3+/Ecad− formed more colonies than 3+/Ecad+ when colony counts were compared in three patients (*P<0.05). FIG. 1D shows results of growth of 3+/Ecad− and 3−Ecad+ cells isolated from primary ascites from ovarian cancer patients by FACS which were plated at 100,000, 50,000, and 25,000 cells in 12-well plates coated by matrigel. After incubation for 28 days at 37° C., colonies were stained (FIG. 1C) and counted (FIG. 1D). CD44/CD24/Epcam triple positive with loss of Ecadherin (3+/Ecad−) (FIG. 1C) formed more colonies than triple negative with Ecadherin (3−Ecad+) (FIG. 1D). FIG. 1E shows 3+/Ecad− and 3−Ecad+ cells sorted from OVCAR-5 were plated on agarose, and FIG. 1F shows 3+/Ecad− and 3−Ecad+ cells sorted from OVCAR-5 were plated on agarose serially diluted ($10^3$, $10^2$ cells). FIG. 1G shows a table of 3+/Ecad− and 3+/Ecad+ cells separated from OVCAR-5 were serially diluted ($10^3$, $10^2$ cells), resuspended in 1:1 PBS/Matrigel, and injected s.c. into 5-wk-old female NOD/SCID mice (nine mice for each group). Kaplan-Meier analysis of $10^3$ ($P<0.001$) and $10^2$ ($P<0.002$) for 3+/Ecad− compared with 3+/Ecad+ cells shows a significant difference in time to tumor appearance (tumor-free interval). Tick bars indicate SD; significant difference in tumor free interval using log-rank and Wilcoxan tests for significance (see Statistical Methods). FIG. 1H shows 3+/Ecad− and 3+/Ecad+ cells isolated from primary ascites from ovarian cancer patients were plated at 50,000 cells in low-melting agarose in 12-well plates and incubated for 2-3 wk, and then colonies were counted. 3+/Ecad− formed more colonies than 3+/Ecad+ when colony counts were compared in three patients (*$P<0.05$). Two-tail t-test of $10^2$ cells shows that 3+/Ecad− cells formed larger tumors than did 3−Ecad+ cells ($p<0.008$). (Bars=standard deviation).

FIG. 2A shows stained colonies for 3+/Ecad− and 3+/Ecad+ cells isolated from OVCAR-5 human ovarian cancer cell line by FACS were plated at 2000 cells in six-well plates, and treated with MIS (30 ug/ml) or Doxorubicin (30 nM) or media (as a control) for 14 days at 37° C. The area stained with Giemsa was equated to colony formation. The colony are formed by 3+/Ecad− cells was greater than that formed by 3−/Ecad+ cells. MIS treatment inhibited colony formation of the 3+/Ecad− cells as compared to doxorubicin (DOX). (n=3 separate experiments). FIG. 2B shows the quantitative results of counting of 3+/Ecad− and 3+/Ecad+ cells isolated from OVCAR-5 human ovarian cancer cell line by FACS which were plated at 2000 cells in six-well plates, and treated with MIS (30 ug/ml) or Doxorubicin (30 nM) or media (as a control) for 14 days at 37° C. 3+/Ecad− formed more colonies than did 3−Ecad+ cells ($p<0.0001$).

FIGS. 3A-3H show tumor suppressor Misr2 correlates negatively with Lin28 in progressively aggressive ovarian cancer tumor tissues. FIG. 3A shows tumor tissues from transgenic mice in which Misr2-Cre−/+ drives constitutively active (CA) β-catenin (Misr2-Cre−/+; ctnnb1ex3/+), and FIG. 3B shows tumor tissue in transgenic mice in which the second Misr2 allele is inactivated (Misr2-Cre−/−; ctnnb1ex3/+). FIGS. 3C, 3D, and 3E show histochemistry staining of ovaries fixed in 4% paraformaldehyde and stained with H&E staining FIG. 3D shows that β-catenin transgenic mice grow small indolent tumors in the ovarian surface epithelium. FIG. 3E shows that when the second allele of the Misr2 is inactivated the transgenic mice grow large ovarian cyst tumors with histological characteristics of endometrioid transition ovarian carcinomas. FIGS. 3F, 3G and 3H show immunohistochemical (IHC) analysis of the ovaries with Lin28 antibody. FIG. 3F shows that Lin28 is detectable in the surface epithelium of the normal ovary of the Misr2-Cre−/+ mice, and as shown in FIG. 3G, is upregulated in the malignant epithelium of the Misr2-Cre−/+; ctnnb1ex3/+ mice. FIG. 3H shows that Lin28 is diffusely expressed in tumors of Misr2-Cre−/−; ctnnb1ex3/+ mice.

FIG. 4A shows lysates from human HOSE 4 and HOSE 6 cell lines derived from normal ovarian surface epithelial cells (Masiakos et al, 1999), and human OVCAR-3, OVCAR-5, OVCAR-8, SKOV-3, and IGROV-1 ovarian cancer cells were analyzed by immunoblotting (IB) with anti-Lin28, anti-Lin28B, or anti-β-actin. FIG. 4B shows qPCR analysis of the levels of Let-7c and Let-7e miRNAs in HOSE 4, HOSE 6, OVCAR-3, OVCAR-5, OVCAR-8, SKOV-3, and IGROV-1 cell lines. Total miRNAs were extracted from the indicated cell lines for quantitative PCR of Let7c and Let7e miRNAs, which showed that Let-7c was expressed at low levels in most human ovarian cancer cell lines compared with normal human ovarian surface epithelium cells. FIG. 4C shows representative results from flow cytometry (FACs) of OVCAR-5 cells using CD44, CD24, and LIN28 antibodies. Subpopulation of 3+/Ecad− OVCAR-5 cells stained with an indirect antibody directed against LIN28 show increased expression (blue arrow), compared to alternate cell types identified within the population. FIG. 4D shows qPCR of Lin28 showed higher expression in 3+/Ecad− than 3+/Ecad+ cells in OVCAR-5 cells (n=3, ** p=<0.01). FIG. 4E shows immunohistohemistry analysis of OVCAR5 cells fixed with 4% paraformaldehyde and stained with mouse/rabbit anti peptide (human) LIN28 (1:500; Abcam) and CD44 (1:100; Abcam) antibodies and immunofluorescence performed with Alexa Fluor 488/568 second antibodies (1:500; Invitrogen). LIN28 (green) is selectively expressed in a small number of OVCAR-5 cells where it colocalized with CD44 (red) and Epcam, suggesting that these cells (yellow cells) may be cancer stem/progenitor cells.

FIG. 5A show expression of MIS type II receptor in human ovarian cancer cell lines OVCAR-5, IGROV-1 and SKOV-3, and in mouse ovarian cancer cell line MOVCAR-8 were analyzed by immunoprecipitation and cross immunoblotting (IB) of lysates with anti-MISRII (Left) Immunoblotting was also performed to detect MISRII expression in separated 3+, 3−, 3+/Ecad−, 3−Ecad+ of OVCAR-5 xenograft tumors (Right). COS cells transfected with a MISRII vector or a pcDNA empty vector served as positive or negative controls (Right). FIG. 5B shows exogeneous human recombinant MIS activates SMAD1/5/8 signaling. MOVCAR-8 (Left) or OVCAR-5 (Right) cells were treated with 20 ug/ml (Left) or 100 ug/ml (Right) MIS for 15 min, 2, 4 and 6 h, and protein was analyzed by Western blot using a phospho-Smad1/5/8 antibody. SMAD 1 protein level showed equal loading of protein.

FIG. 6A shows results of OVCAR-5 cells which were plated for 24 hours in T75 flasks, and then treated with MIS (100 ug/ml for MOVCAR-8; 30 ug/ml for MOVCAR-8) for 3 days in DMEM media. Cells were stained with a combination of CD44, CD24, Epcam, and Ecadherin antibodies and propidium iodide for analysis of cell cycle by flow cytometry. FIG. 6B shows results of MOVCAR-8 cells which were plated for 24 hours in T75 flasks, and then treated with MIS (100 ug/ml for MOVCAR-8; 30 ug/ml for MOVCAR-8) for 3 days in DMEM media. Cells were stained with a combination of CD44, CD24, Epcam, and Ecadherin antibodies and propidium iodide for analysis of cell cycle by flow cytometry.

FIG. 7 shows a table of the pluripotency and X-inactivation in ovarian cancer stem/progenitor cells. Total mRNAs were extracted from separated 3+/Ecad− and 3−Ecad+ OVCAR-5 cells, unseparated OVCAR-5 cells, xenograft tumor cells of 3+, 3−, 3+/Ecad− and 3−Ecad+ OVCAR-5 cells after xenografting, separated 3+ and 3− cells of primary ascites, separated 3+/Ecad− and 3−Ecad+ cells of OVCAR-5 treated with MIS (100 ug/ml) or Doxorubicin (60 nM), and human iPS cells. RT-PCR or qPCR reactions were performed to detect expression of LIN28, OCT-4, SOX2, c-MYC, Nanog, KLF4, ESRBB, WNT5a, DAX1, and XIST. The RT-PCR or qPCR was repeated 3 times per sample to ensure reproducibility. (+, detectable; −, not detectable; NT, not tested). Lin 28 is expressed in the neat and differentially expressed in the 3+Ecad− population.

FIG. 8A shows total mRNAs were extracted from 3+/Ecad− and 3+/Ecad+ cells separated from the OVCAR-5 cell line and xenografts, and levels of mRNAs of the indicated pluripotency factors were measured by RT-PCR. LIN28 is increased in the 3+Ecadcells (n=2 separate experiments with two sets of primers for each pluripotency factor). FIG. 8B shows a representative flow cytometry analyses of OVCAR-5 cells (n=3) indicated that the 3+/Ecad− Subpopulation showed a statistically significant increase (P<0.01) in expression of LIN28 (red peak) compared with total unseparated neat cells (green peak) or with the .Ecad+ population (blue peak).

DETAILED DESCRIPTION

Figure 1A:
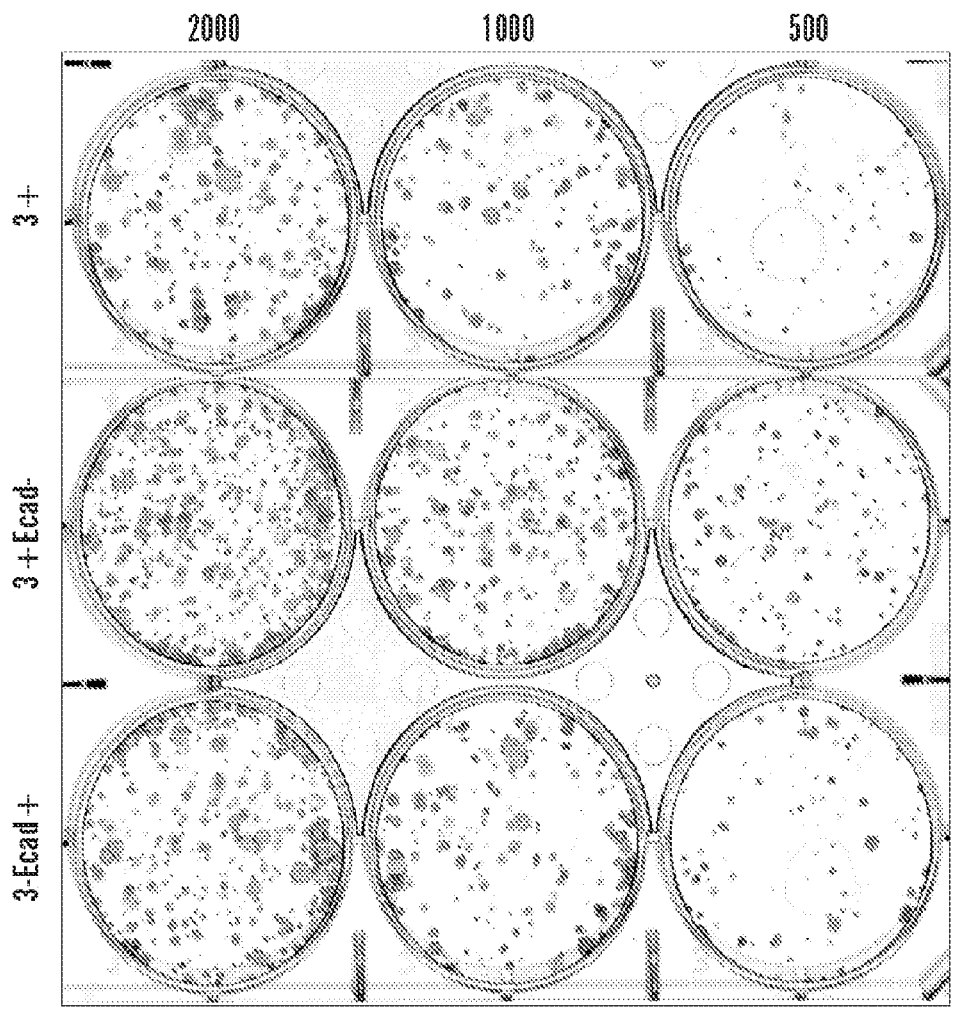
FIGS. 1A-1H show enrichment of human ovarian cancer stem cells enhance colony growth in vitro and shortens tumor-free interval in vivo.

As disclosed herein the present invention relates to isolating a population of ovarian cancer cells which are ovarian cancer stem cells or tumor-initiating cells in a biological sample. One aspect relates to a method to identify ovarian cancer stem cells which fall into two distinct populations; a 3+E− Cadherin positive population (e.g., 3+/Ecad+) and a 3+E− Cadherin negative population, and isolation of the 3+E-Cadherin negative population (e.g., CD44+, CD24+, EpCam+, ECad−) which have increased resistance to chemotherapeutic agents, and their proliferation and/or growth can be inhibited by Mullerian Inhibiting Substance (MIS) or a small molecule MIS mimetic, SP600125. Herein, the inventors have surprisingly discovered that 3+/Ecad− cells comprise less that or approximately 1% of total ovarian cells (a heterogeneous population comprising among other cells, 3+/Ecad− and 3+/Ecad+ cells), and that these 3+/Ecad− cells are stimulated, e.g. have increased proliferation rate by chemotherapeutic agents.

Accordingly, in some embodiments, the present invention relates to isolating and/or identifying a population of ovarian cancer stem cells in a subject which are CD44+, CD24+, EpCam+ and ECad− (3+/Ecad−) whereby a subject identified to have an ovarian cancer comprising such CD44+, CD24+, EpCam+ ECad− (3+/Ecad−) ovarian cancer stem cells is identified to be suitable for treatment with a therapy comprising one or more or a combination of Mullerian Inhibiting Substance (MIS) or a small molecule MIS mimetic, SP600125, or derivatives thereof, or inhibitor of Lin28, each alone or in any combination thereof. A subject with absence of 3+/Ecad− cells is amenable to treatment with chemotherapeutics.

The inventors have herein discovered that an ovarian cancer stem cell population which is CD44+, CD24+, EpCam+ and ECad− (3+/Ecad−) contributes to, or is responsible for chemotherapy drug resistance in human ovarian cancer, and that combinations of chemotherapeutic agents with MIS or SP600125 may be effective adjuvant therapies in controlling ovarian total tumor growth. In particular, the inventors have discovered that 3+/Ecad− cells are stimulated and enriched by chemotherapeutic agents, and thus it is desirable to identify if a subject has the presence of 3+/Ecad− cells prior to beginning a chemotherapeutic treatment, in order to avoid promoting tumor growth and enhancing this population of 3+/Ecad chemotherapeutic resistant ovarian stem cell subpopulation.

Accordingly, another aspect of the invention relates to a method to treat a subject with ovarian cancer, where the subject is identified to have ovarian cancer comprising CD44+, CD24+, EpCam+, ECad− (3+/Ecad−) ovarian cancer stem cells, and the subject is administered a pharmaceutical composition comprising MIS or a derivative or homologue thereof, such as SP600125, or an inhibitor of Lin28. In some embodiments, the subject can be administered additional cancer therapies, for example chemotherapies and other agent, where the subject has absence of 3+/Ecad− cells, or after administration of the subject with MIS or mimetic thereof to eliminate the 3+/Ecad− ovarian stem cell population.

Accordingly, the inventors have discovered methods to identify, isolate and enrich for a CD44+, CD24+, EpCam+, ECad− (3+/Ecad−) ovarian stem cell population. Another aspect of the present invention relates to an assay to identify a population of 3+/Ecad− cells in a biological sample from the subject, where the presence of 3+/Ecad− cells indicates the subject is amenable to administration of one or more, or a combination of any of MIS, a MIS mimetic or SP600125 or derivative thereof, or an inhibitor of Lin28 prior, and the absence of 3+/Ecad− cells indicates the subject is amenable to administration of one or more chemotherapy agents for the treatment of ovarian cancer. Another aspect of the present invention relates to selectively inducing G1 cell cycle arrest or inhibiting the proliferation of 3+/Ecad− cells in vitro or in a subject with ovarian cancer (e.g., in vivo) by contacting these cells with MIS, or a functional mimetic, e.g., SP600125, or an inhibitor of Lin28, alone or in any combination. In some embodiments, MIS or a MIS functional mimetic, e.g., SP600125 or an inhibitor of Lin28 is targeted specifically to 3+/Ecad− cells.

DEFINITIONS

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "3+/Ecad−" as used herein refers to an ovarian cancer stem cell which is positive for expression of CD44, CD24, EpCam and negative for expression of Ecaderin. Such cells are also referred to CD44+/CD24+/EpCam+/ECad− cells.

The term "3+/Ecad+" as used herein refers to an ovarian cancer cell which is positive for expression of CD44, CD24, EpCam and Ecaderin. Such cells are also referred to CD44+/CD24+/EpCam+/ECad+ cells.

The term "3+" as used herein refers to an ovarian cancer stem cell which is positive for expression of CD44, CD24, EpCam. A population of 3+ cells comprise both 3+/Ecad− cells and 3+/Ecad+ cells.

The term "Mullerian Inhibiting Substance" and "MIS" are used interchangeably herein and is also known as anti-Müllerian hormone or AMH, refer to compounds and materials which are structurally similar to MIS. Examples of such intended substances are for example, salts, derivatives and aglycone forms of MIS. Additionally, the present invention is intended to include mutant forms of MIS which have substantially the same biological activity as MIS. Examples of such mutant MIS molecules carrying a deletion, insertion, or alteration in amino acid sequence. MIS can be obtained from any mammalian source or from non-mammalian sources through the use of recombinant DNA technology, or from chemical synthesis of the MIS protein. For reference purposes only, the human MIS nucleic acid corresponds to Accession No: NM_000479 or RefSeq ID No: KO3474 (GeneID: 268), herein referred to as SEQ ID NO: 1 which are incorporated herein by reference. The amino acid sequence for MIS corresponds to SEQ ID NO: 2, and corresponds to Accession No: NP_000470.

The term "Mullerian Inhibiting Substance type II receptor" or "MISRII" are used interchangeably herein refer to the type II receptor for MIS. The term MISRII is intended to encompass all MIS receptors substantially homologous to MISRII and functional derivatives of MISRII. MISRII is also known by the alias as AMHR2, and for reference purposes, the nucleic acid sequence of human MISRII corresponds to NM_020547 and GenBank No: AF172932, and corresponds to SEQ ID NO: 3 and is incorporated herein by reference. The amino acid sequence for MISRII corresponds to SEQ ID NO: 4, and corresponds to Accession No: NP_065434.

The term "functional derivative" and "mimetic" are used interchangeably, and refers to compounds which possess a biological activity (either functional or structural) that is substantially similar to a biological activity of the entity or molecule for which it's a functional derivative. The term functional derivative is intended to include the fragments, variants, analogues or chemical derivatives of a molecule.

The term "derivative" as used herein refers to peptides which have been chemically modified, for example but not limited to by techniques such as ubiquitination, labeling, pegylation (derivatization with polyethylene glycol) or addition of other molecules.

As used herein, "variant" with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide). A "variant" of a MIS for example, is meant to refer to a molecule substantially similar in structure and function, i.e. where the function is the ability to bind with MISRII, to either bind to the entire MISRII molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical.

For example, a variant of an MIS can contain a mutation or modification that differs from a reference amino acid in NM_000479 (SEQ ID NO: 2). In some embodiments, a variant can be a different isoform of MIS or can comprise different isomer amino acids. Variants can be naturally-occurring, synthetic, recombinant, or chemically modified polynucleotides or polypeptides isolated or generated using methods well known in the art. Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the BBB). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).)

In some embodiments, individual substitutions, deletions or additions that alter, add or delete a single amino acid or a small percentage of amino acids can also be considered "conservative substitutions" is the change does not reduce the activity of the peptide (i.e. the ability of, for example MIS to bind and activate MISRII). Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents. As used herein, the term "nonconservative" refers to substituting an amino acid residue for a different amino acid residue that has different chemical properties. The nonconservative substitutions include, but are not limited to aspartic acid (D) being replaced with glycine (G); asparagine (N) being replaced with Lysine (K); or alanine (A) being replaced with arginine (R).

The terms "Insertions" or "deletions" are typically in the range of about 1 to 5 amino acids. The variation allowed can be experimentally determined by producing the peptide synthetically while systematically making insertions, deletions, or substitutions of nucleotides in the sequence using recombinant DNA techniques.

The term "functional derivative" and "mimetic" are used interchangeably, and refers to a compound which possess a biological activity (either functional or structural) that is substantially similar to a biological activity of the entity or molecule its is a functional derivative of. The term functional derivative is intended to include the fragments, variants, analogues or chemical derivatives of a molecule.

A "fragment" of a molecule, is meant to refer to any contiguous polypeptide subset of the molecule. Fragments of, for example MIS which have the same activity as that of MIS encoded by NM_000479, referred to herein as SEQ ID NO: 1 (i.e. a fragment of an MIS peptide which can bind and activate MISRII as the MIS polypeptide corresponding to SEQ ID NO: 2) and which are soluble (i.e. not membrane bound) are also encompassed for use in the present invention.

An "analog" of a molecule such as MIS, for example an analogue of the protein encoded by NM_000479 (SEQ ID NO: 1) is meant to refer to a molecule similar in function to either the entire molecule or to a fragment thereof of SEQ ID NO: 2. As used herein, a molecule is said to be a "chemical derivative" of another molecule when it contains additional chemical moieties not normally a part of the molecule. Such moieties can improve the molecule's solubility, absorption, biological half life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., Mack Publ., Easton, Pa. (1990).

As used herein, "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. The term "substantially homologous" refers to sequences that are at least 90%, at least 95% identical, at least 97% identical or at least 99% identical. Homologous sequences can be the same functional gene in different species.

As used herein, the term "substantial similarity" in the context of polypeptide sequences, indicates that the polypeptide comprises a sequence with at least 60% sequence identity to a reference sequence, or 70%, or 80%, or 85% sequence identity to the reference sequence, or most preferably 90% identity over a comparison window of about 10-20 amino acid residues. In the context of amino acid sequences, "substantial similarity" further includes conservative substitutions of amino acids. Thus, a polypeptide is substantially similar to a second polypeptide, for example, where the two peptides differ by one or more conservative substitutions. The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

Determination of homologs of the genes or peptides of the present invention can be easily ascertained by the skilled artisan. The terms "homology" or "identity" or "similarity" are used interchangeably herein and refers to sequence similarity between two peptides or between two nucleic acid molecules. Homology and identity can each be determined by comparing a position in each sequence which can be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present application.

In one embodiment, the term "MIS peptide homolog" refers to an amino acid sequence that has 40% homology to the full length amino acid sequence of the MIS as disclosed herein, for example the MIS peptide such as SEQ ID NO: 2 or a polypeptide encoded by NM_000479 (SEQ ID NO: 1) as disclosed herein, more preferably at least about 50%, still more preferably, at least about 60% homology, still more preferably, at least about 70% homology, even more preferably, at least about 75% homology, yet more preferably, at least about 80% homology, even more preferably at least about 85% homology, still more preferably, at least about 90% homology, and more preferably, at least about 95% homology. As discussed above, the homology is at least about 50% to 100% and all intervals in between (i.e., 55%, 60%, 70%, 75%, 80%, 85%, 90%, 95%, 98%, etc.).

The term BCRP1, is also known in the art as the ABCG2 transporter is a marker for stem cell-like Hoechst 33342-excluding SP of ovarian cancer stem cells. Also disclosed herein, BCRP1 can confer ovarian cancer cell drug resistance-associated efflux of many lipophilic chemotherapeutic agents, such as for example mitoxantrone, daunorubicin, doxorubicin, indolcarbazole, and others (22). BCRP1 is known in the art under alias of ATP binding cassette transporter G2, placenta specific MDR, mxr1, abcg2, ATP binding cassette sub family g white member 2, cdw338, mitoxantrone resistance, breast cancer resistance, est157481, BCRP, mgc102821, BCRP1, BMDP, ABC transporter, MRX, MRX, ABC15, ABCP, ATP binding cassette sub family g member 2, and for references purposes, the human BCRP1 nucleic acid sequence corresponds to RefSeq ID: NM_004827 and Accession Number AF103796, which correspond to SEQ ID NO: 5 and is incorporated herein by reference. The amino acid sequence for BCRP1 is Accession No: NP_004818.2 and corresponds to SEQ ID NO: 6.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word-length (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=4, and a comparison of both strands.

The term "analog" as used herein, is indented to include allelic, species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are, for example but not limited to; acedisubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine. Fragments and analogs can be screened for prophylactic or therapeutic efficacy in transgenic animal models as described below.

The term "substitution" when referring to a peptide, refers to a change in an amino acid for a different entity, for example another amino acid or amino-acid moiety. Substitutions can be conservative or non-conservative substitutions.

As used herein, the term "subject" refers to any living organism which can be administered to the pharmaceutical compositions of the present invention and in which cancer or a proliferative disorder can occur. The term includes, but is not limited to, humans, non-human animals, for example non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult and newborn subjects, as well as fetuses, whether male or female, are intended to be covered. The term "subject" also includes living organisms susceptible to conditions or disease states as generally disclosed, but not limited to, throughout this specification. Examples of subjects include humans, dogs, cats, cows, goats, and mice, including transgenic species. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term "tissue" is intended to include intact cells, blood, blood preparations such as plasma and serum, bones, joints, muscles, smooth muscles, and organs.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, inderdisposion, affection.

As used herein, the term ovarian cancer as used herein refers to, for example cervical cancer and ovarian cancer. In some embodiments, the ovarian cancer is vulvar epidermal carcinoma, cervical carcinoma, endometrial edenocarinaoma or ovarian adenocarcinoma.

The term 'effective amount" as used herein refers to the amount of an agent and/or a pharmaceutical composition required to reduce at least one of the symptom of the disease or disorder. For example, an effective amount is the amount of required to reduce a symptom of ovarian cancer by at least 10%. An effective amount is also the amount sufficient to prevent the development of a disease symptom, or to reduce a symptom or reduce the rate if a symptom progression.

The term 'malignancy' and 'cancer' are used interchangeably herein, refers to diseases that are characterized by uncontrolled, abnormal growth of cells. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer.

As used herein, the term "treating" includes preventing the progression and/or reducing or reversing at least one adverse effect or symptom of a condition, disease or disorder associated with inappropriate proliferation, for example cancer.

As used herein, the terms "administering" and "introducing" are used interchangeably herein and refer to the placement of the pharmaceutical compositions as disclosed herein into a subject by a method or route which results in at least partial localization of the pharmaceutical compositions at a desired site. The compounds of the present invention can be administered by any appropriate route which results in an effective treatment in the subject.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. The phrases "systemic administration," "administered systemically", "peripheral administration" and "administered peripherally" as used herein mean the administration of the pharmaceutical compositions of the present invention comprising pyrazoloanthrones and optionally other agents or material other than directly into the central nervous system, such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, or be biologically inert.

The term "agent" refers to any entity which is normally not present or not present at the levels being administered in the cell. Agent may be selected from a group comprising, for example chemicals; small molecules; nucleic acid sequences; nucleic acid analogues; proteins; peptides; peptidomimetics, aptamers; antibodies; or fragments thereof. A nucleic acid sequence may be RNA or DNA, and may be single or double stranded, and can be selected from a group comprising; nucleic acid encoding a protein of interest, oligonucleotides, antisense oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), short-temporal RNAi (stRNA), dsRNA antisense oligonucleotides etc. A chemical entity or biological product is preferably, but not necessarily a low molecular weight compound, but may also be a larger compound, or any organic or inorganic molecule, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds. Agents can be, without limitation an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. The agent may be applied to the media, where it contacts the ovarian cell and induces its effects. Alternatively, the agent may be intracellular within the cell as a result of introduction of the nucleic acid sequence into the cell and its transcription resulting in the production of the nucleic acid and/or protein agent within an ovarian cancer cell.

As used herein, "proliferating" and "proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The term "enriching" is used synonymously with "isolating" cells, means that the yield (fraction) of cells of one type is increased over the fraction of other types of cells as compared to the starting or initial cell population. Preferably, enriching refers to increasing the percentage by about 10%, by about 20%, by about 30%, by about 40%, by about 50% or greater than 50% of one type of cell in a population of cells as compared to the starting population of cells.

A "marker" as used herein is used to describe the characteristics and/or phenotype of a cell. Markers can be used for selection of cells comprising characteristics of interests. Markers will vary with specific cells. Markers are characteristics, whether morphological, functional or biochemical (enzymatic) characteristics of the cell of a particular to a cell type, or molecules expressed by the cell type. Preferably, such markers are proteins, and more preferably, possess an epitope for antibodies or other binding molecules available in the art. However, a marker may consist of any molecule found on the surface or within a cell including, but not limited to, proteins (peptides and polypeptides), lipids, polysaccharides, nucleic acids and steroids. Examples of morphological marker characteristics or traits include, but are not limited to, shape, size, and nuclear to cytoplasmic ratio. Examples of functional marker characteristics or traits include, but are not limited to, the ability to adhere to particular substrates, ability to incorporate or exclude particular dyes, for example but not limited to exclusions of lipophilic dyes as disclosed herein, ability to migrate under particular conditions, and the ability to differentiate along particular lineages. Markers may be detected by any method available to one of ordinary skill in the art. Markers can also be a protein expressed from a reporter gene, for example a reporter gene expressed by the cell as a result of introduction of the nucleic acid sequence encoding the reporter gene into the cell and its transcription resulting in the production of the reporter protein that can be used as a marker. Such reporter genes that can be used as markers are, for example but not limited to fluorescent proteins enzymes, chromomeric proteins, resistance genes and the like.

The term 'lineages" as used herein refers to a term to describe cells with a common ancestry, for example cells that are derived from the same ovarian cancer stem cell.

As used herein, the term "clonal cell line" refers to a cell lineage that can be maintained in culture and has the potential to propagate indefinitely. A clonal cell line can be a stem cell line or be derived from a stem cell, and where the clonal cell line is used in the context of clonal cell line comprising stem cells, the term refers to stem cells which have been cultured under in vitro conditions that allow proliferation without differentiation for months to years. Such clonal stem cell lines can have the potential to differentiate along several lineages of the cells from the original stem cell.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a preparation of one or more partially and/or terminally differentiated cell types, refer to a population of cells that contain fewer than about 20%, more preferably fewer than about 15%, 10%, 8%, 7%, most preferably fewer than about 5%, 4%, 3%, 2%, 1%, or less than 1%, of cells that are not cardiovascular stem cells or cardiovascular stem cell progeny of the invention.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied. The terms "peptide(s)", "protein(s)" and "polypeptide(s)" are used interchangeably herein.

The articles "a" and "an" are used herein to refer to one or to more than one (i.e., to at least one) of the grammatical object of the article. By way of example, "an element" means one element or more than one element.

Isolating and/or Enriching for Populations of Ovarian Cancer Stem Cells

As disclosed herein, the inventors have discovered a method to identify, isolate and enrich for CD44+, CD24+, EpCam+, ECad– (3+/Ecad–) ovarian cancer stem cells. One aspect of the present invention provides methods for identification, isolation and enrichment of CD44+, CD24+, EpCam+, ECad– (3+/Ecad–) ovarian cancer stem cells. Encompassed in the methods of the present invention are methods for identification, isolation and enrichment of ovarian cancer stem cells using agents that are reactive to (e.g., bind to the protein or mRNA encoding the proteins of) CD44, CD24, EpCam and ECad, for example agents reactive to the nucleic acids encoding CD44, CD24, EpCam or ECad, for example mRNA of CD44, CD24, EpCam or ECad and in another embodiment, agents are reactive to the expression products of the nucleic acid encoding CD44, CD24, EpCam or ECad, for example agent reactive to CD44, CD24, EpCam or ECad protein or fragments thereof are useful in the methods as disclosed herein. In another embodiment encompasses methods for the identification, isolation and enrichment of populations of ovarian cancer stem cells, the methods comprising using conventional methods of using reporter genes operatively linked to the promoters of CD44, CD24, EpCam or ECad or homologues or variants thereof. In such embodiments, when cells express CD44, CD24, EpCam or ECad protein the cells will also express the reporter gene operatively linked to the promoter of CD44, CD24, EpCam or ECad, and the expression of the reporter gene can be used to isolate, identity and enrich for populations of ovarian cancer stem cells.

As disclosed herein, the ovarian cancer stem cells have the ability to efflux lipophilic molecules, for example lipophilic dyes for example but not limited to Hoechst 33342. In another embodiment, methods for the identification, isolation and enrichment of populations of ovarian cancer stem cells comprises contacting a population of cells with a lipophilic dye, for example Hoechst 33342 and selecting for cells that do not take up the dye, or take up only a small amount of dye as compared to other cells. In such an embodiment, cells that do not comprise as much dye as compared to other, such as somatic non-stem cells are ovarian cancer stem cells.

As used herein, the present invention provides methods to enrich a population of CD44+, CD24+, EpCam+, ECad– (3+/Ecad–) ovarian cancer stem cells. In some embodiments, this encompasses enriching a population of CD44+, CD24+, EpCam+, ECad– (e.g., 3+/Ecad–) ovarian cancer stem cells from a population of cells comprising CD44+, CD24+, EpCam+, ECad+(e.g., 3+/ECad+) cells. For example, 3+/Ecad– cells can be enriched from a mixed population of cancer cells, such as but not limited to a 3+ population of cells, comprising both 3+/Ecad+ cells and 3+/Ecad– cells. In some embodiments, one can positively select for 3+/Ecad+ cells and discard these and select the remaining 3+/Ecad– cell enriched population. Alternatively, one can negatively select for +/Ecad– cells by methods commonly known in the art. As used herein, the term "enriching" or "enrich for" are used interchangeably, and refers to increasing the population of cells of interest, for example ovarian cancer stem cells in a population of cells, for example increasing the percentage of ovarian cancer stem cells by about 10% or about 20% or about 30%, or about 40% or about 50% or about 60% or greater than 60% within the total population cells as compared to the starting population of cells. In some embodiments, as the subpopulation of 3+/Ecad– comprise less than 1% of cancer cells, the methods as disclosed herein provide for enriching for the subpopulation of 3+/Ecad– cells, where the enriched population of cells comprise at least about 10% or at least about 20% or at least about 30% or more than 30% of 3+/Ecad– cells.

Method to determine the expression of surface marker proteins as disclosed herein, such as for example but not limited to, CD44, CD24, EpCam, ECad are well known by persons skilled in the art and are encompassed for use in the methods of the present invention. Such methods of measuring gene expression are well known in the art, and are commonly performed on using DNA or RNA collected from a biological sample of the cells, and can be performed by a variety of techniques known in the art, including but not limited to, PCR, RT-PCR, quantitative RT-PCR (qRT-PCR), hybridization with probes, northern blot analysis, in situ hybridization, microarray analysis, RNA protection assay, SAGE or MPSS. In some embodiments, the probes used detect the nucleic acid expression of the marker genes can be nucleic acids (such as DNA or RNA) or nucleic acid analogues, for example peptide-nucleic acid (PNA), pseudo-complementary PNA (pcPNA), locked nucleic acid (LNA) or analogues or variants thereof.

In other embodiments, the expression of the markers can be detected at the level of protein expression. The detection of the presence of nucleotide gene expression of the markers, or detection of protein expression can be similarity analyzed using well known techniques in the art, for example but not limited to immunoblotting analysis, western blot analysis, immunohistochemical analysis, ELISA, and mass spectrometry. Determining the activity of the markers, and hence the presence of the markers can be also be done, typically by in vitro assays known by a person skilled in the art, for example Northern blot, RNA protection assay, microarray assay etc of downstream signaling pathways of CD44, CD24, EpCam, ECad. In particular embodiments, qRT-PCR can be conducted as ordinary qRT-PCR or as multiplex qRT-PCR assay where the assay enables the detection of multiple markers simultaneously, for example CD44, CD24, EpCam, ECad, together or separately from the same reaction sample.

In some embodiments, conventional methods to isolate a particular stem cell of interest involve positive and negative selection using markers of interest. For example, agents can be used to recognize stem cell markers, for instance labeled antibodies that recognize and bind to CD44, CD24, EpCam, ECad proteins on ovarian cancer stem cells can be used to separate and isolate the ovarian cancer stem cells from non-stem cell ovarian cancer cells using fluorescent activated cell sorting (FACS), panning methods, magnetic particle selection, particle sorter selection and other method known to persons skilled in the art, including density separation (Xu et al. (2002) Circ. Res. 91:501; U.S. patent application 2003/0022367); separation based on physical properties (Doevendans et al. (2000) J. Mol. Cell. Cardiol. 32:839-851). In some embodiments, FACS can be used to negatively select for 3+/Ecad− cells, where cells expressing Ecad (Ecad+ cells) can be selected and discarded, retaining the Ecad− cells. Such Ecad− cells can then be further FACs sorted and selecting those cells which positively express CD44, CD24 and EpCam. In alternative embodiments, one can use FACS to positively select all cells expressing CD44, CD24 and EpCam, then perform a further FACS sorting on the selected CD24+/CD44+/EpCam+ cells to negatively select for 3+/Ecad− cells, where the cells positively expressing Ecad are discarded, and selecting the remaining 3+/Ecad− cells.

Negative selection can also be performed and selecting and removing cells with undesired markers or characteristics, for example, one can negatively select cells and discard cells which express ECad (e.g., ECad+ cells), as well as negatively select and discard cells which do not express CD44 (e.g., CD44− cells), and/or do not express CD24 (e.g., CD24− cells) and/or do not express EpCam (e.g., EpCam− cells) etc. Alternatively, genetic selection methods can be used, where an ovarian cancer cell can be genetically modified to express a reporter protein operatively linked to a tissue-specific promoter and/or a specific gene promoter, therefore the expression of the reporter can be used for positive selection methods to isolate and enrich the desired cell, for example ovarian cancer stem cell. For example, a fluorescent reporter protein can be expressed in the desired stem cell by genetic modification to operatively link the marker protein to the promoter expressed in a desired stem cell (Klug et al. (1996) J. Clin. Invest. 98:216-224; U.S. Pat. No. 6,737,054). Other means of positive selection include drug selection, for instance such as described by Klug et al, supra, involving enrichment of desired cells by density gradient centrifugation.

One variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996). Methods of real-time quantitative PCR using TaqMan probes are well known in the art. Detailed protocols for real-time quantitative PCR are provided, for example, for RNA in: Gibson et al., 1996, A novel method for real time quantitative RT-PCR. Genome Res., 10:995-1001; and for DNA in: Heid et al., 1996, Real time quantitative PCR. Genome Res., 10:986-994. TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data. 5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct). To minimize errors and the effect of sample-to-sample variation, RT-PCR is usually performed using an internal standard. The ideal internal standard is expressed at a relatively constant level among different tissues, and is unaffected by the experimental treatment. RNAs frequently used to normalize patterns of gene expression are mRNAs for the housekeeping genes glyceraldehyde-3-phosphate-dehydrogenase (GAPDH) and β-actin.

In some embodiments, the systems for real-time PCR uses, for example, Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif.). To quantitate the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from 10-106 copies of the gene of interest are generally sufficient. In addition, a standard curve is generated for the control sequence. This permits standardization of initial content of the nucleic acid of interest in a tissue sample to the amount of control for comparison purposes.

Other methods for detecting the expression of genes are well known in the art and disclosed in patent application WO2000/04194, incorporated herein by reference. In an exemplary method, the method comprises amplifying a segment of DNA or RNA (generally after converting the RNA to cDNA) spanning one or more known isoforms of Ecad− gene sequences. This amplified segment is then subjected to a detection method, such as signal detection, for example fluorescence, enzymatic etc. and/or polyacrylamide gel electrophoresis. The analysis of the PCR products by quantitative mean of the test biological sample to a control sample indicates the presence or absence of the marker gene in the cardiovascular stem cell sample. This analysis may also be performed by established methods such as quantitative RT-PCR (qRT-PCR).

The methods of RNA isolation, RNA reverse transcription (RT) to cDNA (copy DNA) and cDNA or nucleic acid amplification and analysis are routine for one skilled in the art and examples of protocols can be found, for example, in the Molecular Cloning: A Laboratory Manual (3-Volume Set) Ed. Joseph Sambrook, David W. Russel, and Joe Sambrook, Cold Spring Harbor Laboratory; 3rd edition (Jan. 15, 2001), ISBN: 0879695773. Particularly useful protocol source for methods used in PCR amplification is PCR (Basics: From Background to Bench) by M. J. McPherson, S. G. Møller, R. Beynon, C. Howe, Springer Verlag; 1st edition (Oct. 15, 2000), ISBN: 0387916008. Other methods for detecting expression of the marker genes by analyzing RNA expression comprise methods, for example but not limited to, Northern blot, RNA protection assay, hybridization methodology and microarray assay etc. Such methods are well known in the art and are encompassed for use in this invention.

Primers specific for PCR application can be designed to recognize nucleic acid sequence encoding Ecad, CD44, CD24 and Epcam can be used and are well known in the art, and are disclosed herein in the Examples.

Any suitable immunoassay format known in the art and as described herein can be used to detect the presence of and/or quantify the amount of any one or a combination of CD44, CD24, EpCam or Ecad marker expression by an ovarian cancer stem cell. In some embodiments, the invention provides methods of screening for the expression of CD44, CD24, EpCam or Ecad markers by immunohistochemical or immunocytochemical methods, typically termed immunohistochemistry ("IHC") and immunocytochemistry ("ICC") techniques. IHC is the application of immunochemistry on samples of tissue, whereas ICC is the application of immunochemistry to cells or tissue imprints after they have undergone specific cytological preparations such as, for example, liquid-based preparations Immunochemistry is a family of techniques based on the use of a specific antibody, wherein antibodies are used to specifically recognize and bind to target molecules on the inside or on the surface of cells, for example CD44, CD24, EpCam or Ecad markers. In some embodiments, the antibody contains a reporter or marker that will catalyze a biochemical reaction, and thereby bring about a change color, upon encountering the targeted molecules. In some instances, signal amplification may be integrated into the particular protocol, wherein a secondary antibody, that includes the marker stain, follows the application of a primary specific antibody. In such embodiments, the marker is an enzyme, and a color change occurs in the presence and after catalysis of a substrate for that enzyme.

Immunohistochemical assays are known to those of skill in the art (e.g., see Jalkanen, et al., J. Cell. Biol. 101:976-985 (1985); Jalkanen, et al., J. Cell. Biol. 105:3087-3096 (1987). Antibodies, polyclonal or monoclonal, can be purchased from a variety of commercial suppliers, or may be manufactured using well-known methods, e. g., as described in Harlow et al., Antibodies: A Laboratory Manual, 2nd Ed; Cold. Spring Harbor Laboratory Press, Cold Spring Harbor, N.Y. (1988). In general, examples of antibodies useful in the present invention include anti-CD44, anti-CD24, anti-Ep-Cam, anti-E-cadherin. Such antibodies are commercially available and can be purchased, for example, from Sigma, US Biologicals, Novus Biologicals, MBL, Millipore, Santa Cruz biotechnology and other commercially available sources, as disclosed herein in Table 1 and in the Examples. In some embodiments, any antibodies that recognize CD44, or CD24, or EpCam or E-Cadherin can be used by any persons skilled in the art, and from any commercial source. Alternatively, antibodies (monoclonal and polyclonal) can easily produced by methods known to person skilled in the art. In alternative embodiments, the antibody can be an antibody fragment, an analogue or variant of an antibody. Anti-CD44 antibodies are commercially available, for example but not limited to from Sigma, US Biologicals, Novus Biologicals, Santa Cruz Biotechnology, Molecular Biology Laboratories, Becton and Dickenson and Millipore.

In some embodiments, where CD44, or CD24, or EpCam or E-Cadherin are detected by immunohistochemistry, the ovarian cancer cells can be fixed by a suitable fixing agent such as alcohol, acetone, and paraformaldehyde prior to, during or after being reacted with (or probed) with an antibody. Conventional methods for immunohistochemistry are described in Harlow and Lane (Eds) (1988) In "Antibodies A Laboratory Manual", Cold Spring Harbor Press, Cold Spring Harbor, N.Y.; Ausbel et al (Eds) (1987), in Current Protocols In Molecular Biology, John Wiley and Sons (New York, N.Y.). Biological samples appropriate for such detection assays include, but are not limited to, cells, tissue biopsy, whole blood, plasma, serum, sputum, cerebrospinal fluid, breast aspirates, pleural fluid, urine and the like. For direct labeling techniques, a labeled antibody is utilized. For indirect labeling techniques, the sample is further reacted with a labeled substance. Alternatively, immunocytochemistry may be utilized. In general, cells are obtained from a patient and fixed by a suitable fixing agent such as alcohol, acetone, and paraformaldehyde, prior to, during or after being reacted with (or probed) with an antibody. Methods of immunocytological staining of biological samples, including human samples, are known to those of skill in the art and described, for example, in Brauer et al., 2001 (FASEB J, 15, 2689-2701), Smith Swintosky et al., 1997. Immunological methods of the present invention are advantageous because they require only small quantities of biological material, such as a small quantity of cardiovascular stem cells. Such methods may be done at the cellular level and thereby necessitate a minimum of one cell.

In some embodiments, cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.) The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radioimmunoassay, etc.

In a different embodiment, antibodies and antibody derivatives or fragments thereof that are used to identify markers on CD44+, CD24+, EpCam+, ECad− (e.g., 3+/ECad−) ovarian cancer stem cells, for example antibodies that recognize CD44 or CD24 or EpCam or ECad protein can be used where the antibodies can bind to at least one epitope or more epitopes on each of the markers (CD44, CD24, EpCam or ECad) and their presence (e.g., for CD44+, CD24+, EpCam+) or absence of binding (e.g., for ECad−) can be detected using analytical techniques, such as by protein dot blots, sodium dodecyl sulfate polyacrylamide gel electrophoresis (SDS-PAGE), or any other gel system that separates proteins, with subsequent visualization of the marker (such as Western blots), gel filtration, affinity column purification; morphologically, such as fluorescent-activated cell sorting (FACS), staining with dyes that have a specific reaction with a marker molecule (such as ruthenium red and extracellular matrix molecules), specific morphological characteristics; and biochemically, such as assaying for an enzymatic product or intermediate, or the overall composition of a cell, such as the ratio of protein to lipid, or lipid to sugar, or even the ratio of two specific lipids to each other, or polysaccharides. If such a marker is a morphological and/or functional trait or characteristic, suitable methods include visual inspection using, for example, the unaided eye, a stereomicroscope, a dissecting microscope, a confocal microscope, or an electron microscope are encompassed for use in the invention. The invention also contemplates methods of analyzing the progressive or terminal differentiation of a cell employing a single marker, as well as any combination of molecular and/or non-molecular markers.

Various methods can be utilized for quantifying the presence of CD44 or CD24 or EpCam proteins and/or the absence of ECad protein and/or nucleic acid expression. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12): 477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112-225; Kawamoto et al. (1999) Genome Res 9(12):1305-12; and Chen et al. (1998) Genomics 51(3):313-24, for examples.

Also encompassed for use in this invention, is the isolation and enrichment of a population of CD44+, CD24+, EpCam+, ECad− (e.g., 3+/ECad−) ovarian cancer stem cells as disclosed herein by the use of introduced reporter genes that aids with the identification of the CD44+, CD24+, EpCam+, ECad− (e.g., 3+/ECad−) ovarian cancer stem cells. As an exemplary example only, ovarian cancer stem cells can be genetically engineered to express a construct comprising a reporter gene which can be used for selection and identification purposes. For example, an ovarian cell is genetically modified to comprise a reporter gene, for example but not limited to a fluorescent protein, enzyme or resistance gene, which is operatively linked to the promoter or fragment thereof of one or more of the genes CD44, CD24 and EpCam. In such an embodiment, when the cell expresses the gene to which the reporter of interest is operatively linked, (e.g., when the cell expresses at least one or more of CD44, CD24 and EpCam), it will express the reporter gene, for example the enzyme, fluorescent protein or resistance gene. Cells that express the reporter gene can be readily detected and in some embodiments positively selected for cells comprising the reporter gene or the gene product of the reporter gene. Other reporter genes that can be used include fluorescent proteins, luciferase, alkaline phosphatase, lacZ, or CAT.

In alternative embodiments, a different reporter gene can be expressed when the ECad is not expressed, which can be used to identify and enrich for CD44+, CD24+, EpCam+, ECad− (e.g., 3+/ECad−) ovarian cancer stem cells. In some embodiments, a reporter gene is expressed when all three of CD44+, CD24+, EpCam+ is expressed which can be used to isolate, identity and enrich a population of 3+ ovarian cancer stem cells, and a different reporter gene such as a different fluorescent reporter gene can be expressed when the ECad is not expressed, which can be used to identify and enrich for 3+/ECad− ovarian stem cells, thus enabling enrichment of populations of CD44+, CD24+, EpCam+, ECad− (e.g., 3+/ECad−) ovarian cancer stem cells within different or the same starting population of cells.

In some embodiments, the cells expressing these reporters could be easily purified by FACS, antibody affinity capture, magnetic separation, or a combination thereof. The purified or substantially pure reporter-expressing cells can be used for genomic analysis by techniques such as microarray hybridization, SAGE, MPSS, or proteomic analysis to identify more markers that characterize the ovarian cancer stem cells. These methods can be used to identify genes expressed by ovarian cancer stem cells and genes important in the self-renewal property of ovarian cancer stem cells. In other embodiments, the reporter gene can be a fluorescent protein, for examples but not limited to; green fluorescent protein (GFP); green fluorescent-like protein (GFP-like); yellow fluorescent protein (YFP); blue fluorescent protein (BFP); enhanced green fluorescent protein (EGFP); enhanced blue fluorescent protein (EBFP); cyan fluorescent protein (CFP); enhanced cyan fluorescent protein (ECFP); red fluorescent protein (dsRED); and modifications and fragments thereof.

In some embodiments, methods to remove unwanted cells are encompassed, by removing unwanted cells by negative selection. For example, unwanted antibody-labeled cells are removed by methods known in the art, such as labeling a cell population with an antibody or a cocktail of antibodies, to a cell surface protein and separation by FACS or magnetic colloids. In an alternative embodiment, the reporter gene may be used to negatively select non-desired cells, for example a reporter gene is expressed by cells expressing ECad (e.g., to discard ECad+ cells), or not expressing CD44, CD24 or EpCam cells (e.g., to discard CD44−, and/or CD24−, and/or EpCam− cells). In some embodiments, the reporter gene can encode a cytotoxic protein in cells that are not desired, thus automatically enriching for a population of desired CD44+, CD24+, EpCam+, ECad− (e.g., 3+/ECad−) ovarian cancer stem cells. In such an embodiment, the reporter gene can be operatively linked to a regulatory sequence of a gene normally expressed in the cells with undesirable phenotype.

Methods of Treatment

The present invention relates generally to a method of preventing and/or treating ovarian cancer in a subject, where the subject has ovarian cancer which comprises CD44+, CD24+, EpCam+, ECad− (e.g., 3+/ECad−) ovarian cancer stem cells as identified by the methods as disclosed herein. In some embodiments, the methods of the present invention comprise administration of an effective amount of MIS or a derivative or fragment thereof to a subject with ovarian cancer, where cancer comprises ovarian cancer stem cells. For example, an effective amount of MIS or a homologue or variant or analogue thereof is administered to a subject with ovarian cancer, wherein the subject is identified to have ovarian cancer comprising ovarian cancer stem cells using the methods as disclosed herein. In some embodiments, administration of MIS to a subject is a MIS protein, for example as disclosed in U.S. Pat. Nos. 5,661,125 and 6,673,352 which are specifically incorporated herein in their entirety by reference. Accordingly, by using the methods of the present invention, one can treat and/or prevent the progression or occurrence of ovarian cancer in a subject wherein the ovarian cancer comprises ovarian cancer stem cells. In some embodiments, the cancer is recurrent ovarian cancer.

In some embodiments, a subject identified to have an ovarian cancer comprising 3+/Ecad− cells can be administered a MIS mimetic, such as but not limited to, a pyrazoloathrone, such as but not limited to SP600125, as disclosed in U.S. application Ser. No. 13/328,387, which is incorporated herein in its entirety by reference. In some embodiments, the pyrazoloathrone is SP600125, as disclosed in U.S. Pat. No. 7,119,114 which is specifically incorporated herein in its entirety by reference. In other embodiments, the pyrazoloathrone is a derivative of pyrazoloathrone, for example substituted antra(1,9-cd)pyrazol-6(2H)-one, and anthrapyrazolone functional derivatives as disclosed in European Patent EP0103381 and EP0700390, which are incorporated herein in their entirety by reference.

In some embodiments, the pyrazoloanthrone is antra(1,9-cd)pyrazol-6(2H)-one (herein also referred to as SP600125 or Compound I). In alternative embodiments, the pyrazoloanthrone is a functional derivative of a pyrazoloanthrone, and may generally be classified as "pyrazoloanthrone derivatives" having the following structure (I), also referred to herein as Compound (II):

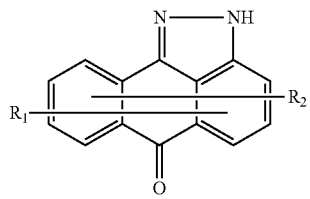

wherein $R_1$ and $R_2$ are as defined in U.S. Pat. No. 7,119,114, including pharmaceutically acceptable salts thereof. Pyrazoloanthrone, for example antra(1,9-cd)pyrazol-6(2H)-one (herein also referred to as SP600125 or Compound II) and pyrazoloanthrone derivatives (having the structure (I) are disclosed in U.S. Pat. No. 7,119,114 which is incorporated in its entirety herein by reference.

In some embodiments, a subject identified to have an ovarian cancer comprising 3+/Ecad− cells can be administered an inhibitor of Lin28 Inhibitors of Lin28 are well known in the art, and include both inhibitors of Lin28 protein as well as inhibitors of expression of Lin28 mRNA. Lin28 inhibitors encompassed of use in the methods of treatment of ovarian cancer as disclosed herein are disclosed in US Patent Application US2010/0221266, which is incorporated herein in its entirety by reference.

In some embodiments, agents useful in the methods and compositions as disclosed herein for inhibition of Lin-28 and/or Lin-28B expression (protein or gene expression) or activity include for example, but are not limited to, a small molecule, nucleic acid, nucleic acid analogue, aptamer, ribosome, peptide, protein, antibody, or variants and fragments thereof. In some embodiments, an agent is an antibody, for example, a recombinant antibody, humanized antibody, chimeric antibody, modified antibody, monoclonal antibody, polyclonal antibody, miniantibody, dimeric miniantibody, minibody, diabody or tribody or variants, analogues or modified versions thereof. In other embodiments, agents useful for inhibition of Lin-28 and/or Lin-28B expression are nucleic acid molecules, such as DNA, RNA, nucleic acid analogue, peptide nucleic acid (PNA), pseudo-complementary PNA (pcPNA), locked nucleic acid (LNA), antagomir or analogue thereof. In particular embodiments, an agent can be a RNA molecule, for example a small inhibitory RNA (RNAi) such as siRNA, microRNA, shRNA, miRNA molecules and analogues and homologues and variants thereof. In some embodiments, an RNAi molecules useful in the methods as disclosed herein are siRNA molecules to Lin-28 which correspond to the nucleic acid sequences in pLKO.1-shRNA plasmids targeting Lin-28 from the Broad-TRC collection (Sigma-Aldrich), where TRC numbers for hairpins useful are sh1 (TRCN0000102575) (5'-CCGG-CCCAGTAAGAATG-CAACTTAA-CTCGAG-TTAAGTTGCATTCT-TACTGGG-TTTTTG-3; SEQ ID NO:7), sh2 (TRCN0000102578) (5'-CCGG-CAAAGGAGACAGGT-GCTACAA-CTCGAG-TTGTAGCACCTGTCTCCTTTG-TTTTTG-3; SEQ ID NO:8), and sh3 (TRCN0000102579) (5'-CCGG-CATCTGTAAGTGGTTCAACGT-CTCGAG-ACGTTGAACCACTTACAGATG-TTTTTG-3; SEQ ID NO:9). Other siRNA molecules to Lin-28 which are commonly known by persons of ordinary skill in the art are encompassed for use in the methods, kits and compositions as disclosed herein, and are available from Broad Institute at world-wide web at: "broadinstitute.org/rnai/public/gene/details?geneId=TRCG0000025667"

In alternative embodiment, an agent can be a nucleic acid inhibitor agent or antagomir which binds to the let-7 miRNA target site in the 3'UTR of the Lin-28 gene. In alternative embodiments, an agent can be a miRNA such as Lin4 or let-7 or variants thereof.

In some embodiments, where the subject is identified as having ovarian cancer comprising CD44+, CD24+, EpCam+, ECad− (e.g., 3+/ECad−) ovarian cancer stem cells, the subject is administered a pharmaceutical composition comprising a BCRP1 inhibitor, for example a verapamil. In some embodiments, where the subject is identified as having ovarian cancer comprising CD44+, CD24+, EpCam+, ECad− (e.g., 3+/ECad−) ovarian cancer stem cells, the subject is administered a pharmaceutical composition comprising a BCRP1 inhibitor and/or MIS or a derivative or fragment or variant thereof.

Inhibitors of BCRP1 are commonly known by one of ordinary skill in the art, for example but not limited to verapamil, Reserpine, CI1033, GF120918, FTC, ko138, P-gp and analogues and derivatives thereof, as disclosed in Allen et al, Mol Cancer Therapeutics, 2002; 1:427-434, which is incorporated herein in its entirety by reference. The chemical structures of GF120918, FTC (Furmitremorgin) and ko138 are as follows:

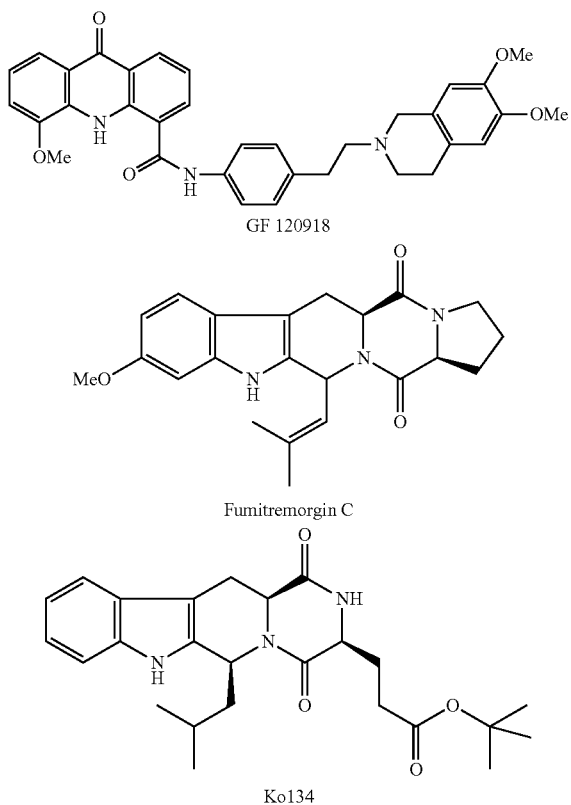

In some embodiments, the MIS is a MIS protein, for example recombinant human MIS (rhMIS). In such embodiments, MIS or rhMIS can be prepared and administered, in any form, by any method known by persons of ordinary skill in the art, for example as disclosed in International Patent Application WO92/18152 and European Patent EP584287 and also disclosed in patent Applications WO94/00133 and EP221761, which are incorporated herein in their entity by reference.

In another embodiment, the methods as disclosed herein also contemplates the administration of MIS, or a MIS mimetic, or an inhibitor of Lin28, or any combination thereof, to a subject identified with ovarian cancer comprising 3+/Ecad− cancer stem cells in conjunction with other therapies such as conventional chemotherapy, radiotherapy, hormone therapy, immunotherapy, thermotherapy and surgery directed against solid tumors and for control of establishment of metastases. The administration of the compounds described herein is typically conducted prior to and/or at the same time and/or after such additional therapies, although it is also encompassed within the present invention to administer a pharmaceutical composition comprising, for example MIS or a variant or derivative thereof, and/or an inhibitor of BCRP1 or Lin28 prior to administration of a chemotherapeutic agent, therefore avoiding stimulating proliferation of 3+/Ecad− cells, as disclosed herein.

In addition, in some embodiments the pharmaceutical compositions as disclosed herein for the treatment of a subject with ovarian cancer comprising 3+/Ecad− ovarian cancer stem cells can be administrated prophylactically and/or before the development of a tumor, if the subject has been identified as to have a risk of developing ovarian cancer comprising 3+/Ecad− cells, for example to subjects that are positive for biomarkers of ovarian cancer cells or tumors. Insofar as the present methods apply to inhibition of proliferation and growth of 3+/Ecad− ovarian cancer stem cells, the methods can also apply to inhibition of ovarian cancer tissue growth, to inhibition of ovarian cancer metastases formation, and to regression of established ovarian cancer tumors.

The effective amount of an agent to inhibit the proliferation of 3+/Ecad− cells can vary depending upon criteria such as the age, weight, physical condition, past medical history, and sensitivity of the recipient. The effective amount will also vary depending on whether administration is oral, intravenous, intramuscular, subcutaneous, local, or by direct application to the tumor. In the case of direct tumor application, it is preferable that a final serum concentration of at least 0.1 nM, preferably about 0.1-1.0 nM, of MIS be achieved. Effective individual dosage through the additionally named means of administration can be readily determined by methods well known to those of ordinary skill in the art. For example, using the size ratio calculation as detailed above, one of ordinary skill in the art can determine optimal dosage levels for any means of administration. In treating a patient, it is preferable to achieve a serum level of at least 10 ng/ml of MIS.

Compositions containing MIS or its functional derivatives may be administered orally, intravenously, intramuscularly, subcutaneously, or locally. Additional pharmaceutical methods nay be employed to control the duration of action. Controlled release preparations may be achieved by the use of polymers to complex or adsorb MIS or its functional derivatives. The controlled delivery may be exercised by selecting appropriate macromolecules (for example polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release. In some embodiments, the composition comprising MIS, or MIS mimetics, e.g., SP600125 can be in an emulsion.

Another possible method to control the duration of action by controlled release preparations is to incorporate MIS, SP600125, inhibitors of Lin28, alone or in any combination, into particles, e.g., nanoparticles, liposomes, or microemulsions or particles of a polymeric material such as polyesters, polyamino acids, hydrogels, poly(lactic acid) or ethylene vinyl acetate copolymers. Alternatively, instead of incorporating MIS into these polymeric particles, it is possible to entrap MIS in microcapsules prepared, for example, by coacervation techniques or by interfacial polymerization, for example, hydroxymethylcellulose or gelatin microcapsules and poly(methylmethacrylate) microcapsules, respectively, or in colloidal drug delivery systems, for example, liposomes, albumin microspheres, microemulsions, nanoparticles, and nanocapsules or in macroemulsions. Such teachings are disclosed in Remington's Pharmaceutical Sciences, supra (1980).

Pharmaceutical compositions which include the proteolytically cleaved MIS protein fragments, inhibitors of Lin28, and/or SP600125, alone or in any combination as disclosed herein can also include chemotherapeutic agents which are known to inhibit tumor growth in a human or animal. In some embodiments, the chemotherapeutic agent is time (e.g., delayed) release formulation, such that the chemotherapeutic agent is released at a pre-determined time after the release of the MIS, SP600125 or Lin28 inhibitor. In some embodiments, a chemotherapeutic agent encompassed to be used can be directed to any specific neoplastic disease. Such agents are described in Goodman and Gilman's The Pharmacological Basis of Therapeutics, 8th Ed., Pergamon Press, New York, N.Y., 1985. It is preferred, however, that the chemotherapeutic agent inhibits the growth of the tumors of this invention.

In some embodiments a subject identified to have ovarian cancer comprising CD44+, CD24+, EpCam+, ECad− (e.g., 3+/ECad−) ovarian cancer stem cells can be administered other therapies, for example but not limited to chemotherapeutic agents. As disclosed herein, a subject identified with an ovarian cancer comprising 3+/Ecad− cells can be treated in a two-phase treatment regimen, for example, the subject is first treated with MIS, and/or a MIS mimetic (e.g., SP600125), and/or an Lin28 inhibitor or any combination thereof for a pre-defined period of time in order to inhibit the proliferation and to selectively eliminate 3+/Ecad− cells in the ovarian cancer, followed by a second treatment phase comprising administration of a chemotherapeutic agent. In some embodiments, a subject can be screened for the presence of 3+/Ecad− cells after the first treatment phase (administration of MIS, mimetics, etc.) and prior to the second treatment phase comprising administration of the chemotherapeutic agent, and only administered the chemotherapeutic agent when the absence of 3+/Ecad− cells is determined in the subjects ovarian cancer. In some embodiments, the chemotherapeutic agent is a BCRP1 protein inhibitor, for example but not limited to verapamil.

In alternative embodiments, a subject is administered other chemotherapeutic agents in the second treatment phase or when the absence of 3+/Ecad− cells are determined in a subject. In such an embodiment, a subject with ovarian cancer which lacks 3+/Ecad− cells can be treated with chemotherapeutic agents, for example paclitaxel, cisplatin, doxorubicin, rapamycin, and the like. However, as disclosed herein, as chemotherapeutic agents stimulate the proliferation and growth of 3+/Ecad− cells, the timing of the administration of a chemotherapeutic should be carefully regulated. In some embodiments, chemotherapeutic agents are administered after administration of MIS, a MIS mimetic (e.g., SP600125) or inhibitor of Lin28. In some embodiments, a subject is tested or assessed for the presence or absence of 3+/Ecad− cells after a first treatment or administration of MIS, a MIS mimetic (e.g., SP600125) or inhibitor of Lin28, wherein if the subject is determined to have ovarian cancer which does not comprise 3+/Ecad− cells, the subject can then be subsequently administered a chemotherapeutic agent, e.g., but not limited to paclitaxel, cisplatin, doxorubicin, rapamycin.

Other chemotherapeutic agents which can be administered to a subject with ovarian cancer which does not comprise 3+/Ecad− cells include, without limitation nitrogen mustards such as cyclophosphamide, ifosfamide, and melphalan; ethylenimines and methylmelamines such as hexamethylmelamine and thiotepa; pyrimidine analogs such as fluorouracil and fluorodeoxyuridine; vinca alkaloids such as vinblastine; epipodophyllotoxins such as etoposide and teniposide; antibiotics such as actinomycin D, doxorubicin, bleomycin, and mithramycin; biological response modifiers such as interferon; platinum coordination complexes such as cisplatin and carboplatin; estrogens such as diethylstilbestrol and ethinyl estradiol; antiandrogens such as flutamine; and gonadotropin releasing hormone analogs such as leuprolide. Other compounds such as decarbazine, nitrosoureas, methotrexate, diticene, and procarbazine are also effective. Of course, other chemotherapeutic agents which are known to those of ordinary skill in the art can readily be substituted as this list should not be considered exhaustive or limiting.

It is to be understood that the use of the term "equivalent effective amount" does not necessarily mean an equivalent weight or volume quantity, but represents the quantity of MIS, MIS mimetic (e.g., SP600125) or Lin28 inhibitor that offers an equal inhibition to tumor growth, or G1 arrest of the cell cycle of 3+/Ecad− cells. This may have to be evaluated on a patient by patient case, but can be determined, for example, by comparing quantities that achieve equal size reduction ratios as defined above. Typically, chemotherapeutic agents to be combined with MIS for treatment of the tumors of this invention can be effective between about 0.001 and 10.0 mg/kg body weight of the patient. Administration of the chemotherapeutic agent can be accomplished in the same manner or a different manner as administration of the MIS, MIS mimetic or Lin28 inhibitor.

In some embodiments, the methods as disclose herein for treating ovarian cancer in a subject which comprises CD44+, CD24+, EpCam+, ECad− (e.g., 3+/ECad−) ovarian cancer stem cells comprising contacting a tissue in which tumor is occurring, or is at risk for occurring, with the compositions of the present invention comprising a therapeutically effective amount of MIS or derivatives or analogues thereof.

In some embodiments, the subject treated by the methods of the present invention in its many embodiments is a human subject, although it is to be understood that the principles of the invention indicate that the invention is effective with respect to all mammals. In this context, a mammal is understood to include any mammalian species in which treatment of diseases associated with cancer or a proliferative-related disorder is desirable, particularly agricultural and domestic mammalian species, as well as transgenic animals.

Administration of Pharmaceutical Compositions

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

After formulation with an appropriate pharmaceutically acceptable carrier in a desired dosage, the pharmaceutical compositions of this invention can be administered to a subject. The pharmaceutical compositions of this invention can be administered to a subject using any suitable means. In general, suitable means of administration include, but are not limited to, topical, oral, parenteral (e.g., intravenous, subcutaneous or intramuscular), rectal, intracisternal, intravaginal, intraperitoneal, ocular, or nasal routes.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

In some embodiments, the methods as disclosed herein provide for the parenteral and oral administration of the compounds of the present invention, in combination with other pharmaceutical compositions to subjects in need of such treatment. Parenteral administration includes, but is not limited to, intravenous (IV), intramuscular (IM), subcutaneous (SC), intraperitoneal (IP), intranasal, and inhalant routes. In the method of the present invention, the resolvins and/or protectins or analogs thereof are preferably administered orally. IV, IM, SC, and IP administration may be by bolus or infusion, and may also be by slow release implantable device, including, but not limited to pumps, slow release formulations, and mechanical devices. The formulation, route and method of administration, and dosage will depend on the disorder to be treated and the medical history of the subject. In general, a dose that is administered by subcutaneous injection will be greater than the therapeutically-equivalent dose given intravenously or intramuscularly.

In general, a suitable daily dose of a compound of the invention will be that amount of the compound which is the lowest dose effective to produce a therapeutic effect, where the desired therapeutic effect is cell cycle arrest of 3+/Ecad− cells or killing of 3+/Ecad− cells. Such an effective dose will generally depend upon the factors described above. If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" of one or more of the compounds of the present invention, or derivatives thereof. A "therapeutically effective amount" refers to an amount effective, at dosages and for periods of time necessary, to achieve the desired therapeutic result, e.g., a diminishment or prevention of effects associated with ovarian cancer, wherein the cancer comprises 3+/Ecad− ovarian cancer stem cells. For example, a therapeutically effective amount of MIS, MIS mimetics or Lin28 inhibitors of the present invention or derivatives thereof may vary according to factors such as the disease state, age, sex, and weight of the subject, and the ability of the therapeutic compound to elicit a desired response in the subject. A therapeutically effective amount is also one in which any toxic or detrimental effects of the therapeutic agent are outweighed by the therapeutically beneficial effects.

In some embodiments, a subject can be given a prophylactically effective amount. Such a prophylactic amount is desired if a subject to be treated has had 3+/Ecad− cells, and been treated to effectively substantially eliminate such population of 3+/Ecad− cells. Such a subject can be administered a prophylactically effective amount to prevent reoccurrence of 3+/Ecad− cells. Alternatively, a prophylactic amount can be given to a subject likely to have 3+/Ecad− cells. A "prophylactically effective amount" refers to an amount effective, at dosages and for periods of time necessary, to achieve the desired prophylactic result. Typically, since a prophylactic dose is used in subjects prior to, or at an earlier stage of disease, the prophylactically effective amount may be less than the therapeutically effective amount. A prophylactically or therapeutically effective amount is also one in which any toxic or detrimental effects of the compound are outweighed by the beneficial effects.

Dosage regimens may be adjusted to provide the optimum desired response (e.g. a therapeutic or prophylactic response). For example, a single bolus may be administered, several divided doses may be administered over time or the dose may be proportionally reduced or increased as indicated by the exigency of the therapeutic situation. It is especially advantageous to formulate parenteral compositions in dosage unit form for ease of administration and uniformity of dosage. Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the patient.

The term "dosage unit" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound and the particular therapeutic or prophylactic effect to be achieved, and (b) the limitations inherent in the art of compounding such an active compound for the treatment of sensitivity in subjects.

The therapeutically effective amount can be estimated initially either in cell culture assays or in animal models in vivo, usually mice (e.g., as disclosed herein in the Examples using a human ovarian cancer cell line xenographed in a mouse ovarian cancer model), rabbits, dogs, or pigs. The animal model is also used to achieve a desirable concentration range and route of administration. Such information can then be used to determine useful doses and routes for administration in other subjects. Generally, the therapeutically effective amount is sufficient to reduce or inhibit cell proliferation in a subject suffering from a proliferative disorder, for example cancer. In some embodiments, the therapeutically effective amount is sufficient to eliminate the proliferative cells, for example eliminate the cancer cells and/or tumor in a subject suffering cancer and/or a proliferative disease.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the subject.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Pharmaceutical Compositions

In another embodiment of the invention, pharmaceutical compositions containing one or more compounds of this invention are disclosed. For purpose of administration, in some embodiments MIS or derivatives, fragments or variants, or MIS mimetics (e.g, SP600125), or analogues, or Lin28 inhibitors thereof can be formulated as a pharmaceutical composition. Pharmaceutical compositions of the present invention comprise a compound of this invention and a pharmaceutically acceptable carrier, wherein the compound is present in the composition in an amount which is effective to treat the condition of interest.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds of this invention in an appropriate manner, and in accordance with accepted practices, such as those disclosed in *Remington's Pharmaceutical Sciences*, Gennaro, Ed., Mack Publishing Co., Easton, Pa. 1990.

While it is possible to administer MIS, MIS mimetics (e.g., SP600125), Lin28 inhibitors and derivatives and fragments alone, it is preferable to administer MIS as pharmaceutical compositions.

Formulations of the invention can be prepared by a number or means known to persons skilled in the art. In some embodiments the formulations can be prepared by combining (i) MIS and derivatives fragments, variants and analogues thereof, in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a co-solvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

The compositions of the present invention can be in any form. These forms include, but are not limited to, solutions, suspensions, dispersions, ointments (including oral ointments), creams, pastes, gels, powders (including tooth powders), toothpastes, lozenges, salve, chewing gum, mouth sprays, pastilles, sachets, mouthwashes, aerosols, tablets, capsules, transdermal patches, that comprise one or more of the compounds of the present invention, and/or their derivatives thereof for oral or subcutaneous administration.

In certain embodiments, the compounds of the present invention, for MIS mimetics (e.g., SP600125), Lin28 inhibitors or derivatives or variants thereof are administered to a subject as a pharmaceutical composition with a pharmaceutically acceptable carrier.

In certain embodiments, these pharmaceutical compositions optionally further comprise one or more additional therapeutic agents. In certain embodiments, the additional therapeutic agent or agents are anti-cancer agents. In some embodiments, the anti-cancer agents or chemotherapeutic agents are delayed in a time release such that the MIS, MIS mimetic and/or Lin28 inhibitor initiate G1 cell cycle arrest of 3+/Ecad− cells prior to the release of the chemotherapeutic agent. In some embodiments, the therapeutic agents are chemotherapeutic agents, for example but not limited to, cisplatin, paxicital etc. In some embodiments, the therapeutic agents are radiotherapeutic agents. Examples of chemotherapeutic agents in the pharmaceutical compositions of this invention are, for example nitrogen mustards such as cyclophosphamide, ifosfamide, and melphalan; ethylenimines and methylmelamines such as hexamethylmelamine and thiotepa; pyrimidine analogs such as fluorouracil and fluorodeoxyuridine; vinca alkaloids such as vinblastine; epipodophyllotoxins such as etoposide and teniposide; antibiotics such as actinomycin D, doxorubicin, bleomycin, and mithramycin; biological response modifiers such as interferon, platinum coordination complexes such as cisplatin and carboplatin; estrogens such as diethylstilbestrol and ethinyl estradiol; antiandrogens such as flutamine; and gonadotropin releasing hormone analogs such as leuprolide. Other compounds such as decarbazine, nitrosoureas, methotrexate, diticene, and procarbazine are also effective and encompassed for use in the methods of the present invention. Of course, other chemotherapeutic agents which are known to those of ordinary skill in the art can readily be substituted as this list should not be considered exhaustive or limiting.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. The term "pharmaceutically acceptable carriers" is intended to include all solvents, diluents, or other liquid vehicle, dispersion or suspension aids, surface active agents, isotonic agents, thickening or emulsifying agents, preservatives, solid binders, lubricants and the like, as suited to the particular dosage form desired. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention.

These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs are salts or prodrugs that are, within the scope of sound medical judgment, suitable for use in contact with the tissues of subject without undue toxicity, irritation, allergic response, and the like, commensurate with a reasonable benefit/risk ratio, and effective for their intended use. These compounds include the zwitterionic forms, where possible, of compounds of the invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylanunonium, tetraethyl ammonium, methyl amine, dimethyl amine, trimethylamine, triethylamine, ethylamine, and the like (see, e.g., Berge S. M., et al. (1977) J. Pharm. Sci. 66, 1, which is incorporated herein by reference).

The term "prodrug" refers to compounds that are rapidly transformed in vivo to yield the compounds of the invention, for example MIS as disclosed herein, by hydrolysis in blood. In some embodiments, a pharmaceutical composition as disclosed herein comprises at least one of MIS, a MIS mimetic (e.g., SP600125) or Lin28 inhibitor and a prodrug of a chemotherapeutic agent, such that the chemotherapeutic agent is only active upon activation of the prodrug to a biologically active chemotherapeutic agent. In some embodiments, a second agent is required to activate the chemotherapeutic agent prodrug into an active chemotherapeutic agent. A thorough discussion is provided in T. Higachi and V. Stella, "Pro-drugs as Novel Delivery Systems," Vol. 14 of the A.C.S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. The prodrug may be designed to alter the metabolic stability or the transport characteristics of a compound, to mask side effects or toxicity, to improve the flavor of a compound or to alter other characteristics or properties of a compound. By virtue of knowledge of pharmacodynamic processes and drug metabolism in vivo, once a pharmaceutically active compound is identified, those of skill in the pharmaceutical art generally can design prodrugs of the compound (see, e.g., Nogrady (1985) Medicinal Chemistry A Biochemical Approach, Oxford University Press, N.Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

In other embodiments of the present invention, MIS, MIS mimetics (e.g., SP600125), and/or Lin28 inhibitors and derivatives thereof are conjugated or covalently attached to another targeting agent to increase the specificity of MIS and derivatives thereof to target the cell, for example to target specifically to CD44+, CD24+, EpCam+, ECad− (e.g., 3+/ECad−) ovarian cancer stem cell. Targeting agents can include, for example without limitation, antibodies, cytokines and receptor ligands. In some embodiments, the targeting agent is overexpressed on the cells to be targeted, for example the cancer cells as compared to normal cells. In alternative embodiments, the MIS and derivatives thereof can be conjugated or covalently attached to compounds that elicit an immune response, such as for example but without limitation, cytokines.

In some embodiments, MIS and derivatives thereof of the present invention can be conjugated to, by covalent linkage or any other means, to another agent, for example chemotherapy agents for example BCRP1 inhibitors. In some embodiments, MIS and derivatives thereof of the present invention can be conjugated to a targeting moiety, for example an ovarian cancer cell targeting moiety to target the MIS to a CD44+, CD24+, EpCam+, ECad− (e.g., 3+/ECad−) ovarian cancer stem cell. Such targeting moieties and methods are well known by persons of ordinary skill in the art and are encompassed for use in the methods of the present invention. In some embodiments, a targeting moiety is a moiety that interacts with CD44, or CD24, or EpCam present on the exterior of the CD44+, CD24+, EpCam+, ECad− (e.g., 3+/ECad−) ovarian cancer stem cell. In some embodiments, the conjugation may be a permanent or reversible conjugation.

In some embodiments, MIS and derivatives thereof of the present invention can be a homodimer of MIS, or can be a pro-drug or a pro-hormone.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients. In one aspect, a solution of resolvin and/or protectin or precursor or analog thereof can be administered as eye drops for ocular neovascularization or ear drops to treat otitis.

Liquid dosage forms for oral administration of the compounds of the invention include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some instances, pharmaceutical compositions comprising the resolvins and protectins of the invention for the administration of angiogenesis may be in a formulation suitable for rectal or vaginal administration, for example as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore release the active compound. Suitable carriers and formulations for such administration are known in the art.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the compounds (resolvins and/or protectins and/or precursors or analogues thereof) of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Remington's Pharmaceutical sciences Ed. Germany, Merk Publishing, Easton, Pa., 1995 (the contents of which are hereby incorporated by reference), discloses various carriers used in formulating pharmaceutical compositions and known techniques for the preparation thereof. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; malt; gelatin; talc; excipients such as cocoa butter and: suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; water; isotonic saline; Ringer's solution, ethyl alcohol, and phosphate buffer solutions, as well as other non-toxic compatible lubricants such as sodium lauryl sulfate and magnesium sulfate, as well as coloring agents, releasing agents, coating agents, sweetening, flavoring and perfuming agents, preservatives and antioxidants can also be present in the composition, according to the judgment of the formulator.

Uses of the Ovarian Cancer Stem Cells

In some embodiments, the CD44+, CD24+, EpCam+, ECad− (e.g., 3+/ECad−) ovarian cancer stem cells as disclosed herein can be isolated and enriched using the methods as disclosed herein, for example purified by FACS, antibody affinity capture, magnetic separation, or a combination thereof using the surface markers as disclosed herein, such as, but not limited to, Lin28+ expression, and MISRII expression and/or lipophilic dye exclusion. A purified or substantially pure population of CD44+, CD24+, EpCam+, ECad− (e.g., 3+/ECad−) ovarian cancer stem cells can be used for genomic analysis by techniques such as microarray hybridization, SAGE, MPSS, or proteomic analysis to identify more markers that characterize the ovarian cancer stem cell populations and/or somatic ovarian stem cell populations.

One aspect of the present invention relates to an assay to identify agents that reduce the self-renewal capacity of a CD44+, CD24+, EpCam+, ECad− (e.g., 3+/ECad−) ovarian cancer stem cell population as compared to somatic ovarian stem cells such as coelomic ovarian stem cell populations and/or subcoelomic/stromal ovarian stem cell populations and periphilar medullary ovarian stem cell populations. In some embodiments, the assay involves contacting a CD44+, CD24+, EpCam+, ECad− (e.g., 3+/ECad−) ovarian cancer stem cell population with an agent, and measuring the proliferation of the 3+/ECad− cells, whereby an agent that decreases the proliferation of the 3+/ECad− cells as compared to a reference agent or absence of an agent identifies an agent that inhibits the self-renewal capacity of the CD44+, CD24+, EpCam+, ECad− (e.g., 3+/ECad−) ovarian cancer stem cell. Such an agent can be used for development of therapies for the treatment of ovarian cancer. In some embodiments, the assay can encompass comparing the results of the rate of proliferation of a somatic ovarian stem population, for example a coelomic ovarian stem cell population in the presence of the same agent, where an agent useful for selection as a therapy for the treatment of ovarian cancer in a subject is an agent that inhibits the self-renewal capacity of a population of CD44+, CD24+, EpCam+, ECad− (e.g., 3+/ECad−) ovarian cancer stems to a greater extent, for example greater than 10%, or greater than about 20%, or greater than 30% as compared to the ability of the agent to inhibit the self-renewal capacity of a population of somatic ovarian stem cells, for example a coelomic ovarian stem cell population. Examples of somatic ovarian stem cells are disclosed in US application 2010/0273160, which is incorporated herein in its entirety by reference.

Also encompassed in the present invention is use of the CD44+, CD24+, EpCam+, ECad− (e.g., 3+/ECad−) ovarian cancer stem cells as disclosed herein in assays to identify agents which kill and/or decrease the rate of proliferation of the CD44+, CD24+, EpCam+, ECad− (e.g., 3+/ECad−) ovarian cancer stem cells preferentially over other types of cells (e.g., normal non-cancerous ovarian cells, such as somatic ovarian cells, or non-cancerous ovarian cancer stem cell population which are normally residing in the ovary). In some embodiments, such an assay can comprise both a population of CD44+, CD24+, EpCam+, ECad− (e.g., 3+/ECad−) ovarian cancer stem cells and a population of somatic ovarian stem cells, for example coelomic ovarian stem cell and/or subcoelomic/stromal ovarian stem cells and/or periphilar medullary ovarian stem cells, but preferably coelomic ovarian stem cells and adding to the media of the population of 3+/ECad− ovarian cancer stem cells and to the population of somatic ovarian stem cells one or more of the same agents. Once can measure and compare the rate of proliferation of the population of the 3+/ECad− ovarian cancer stem cells and the population of somatic ovarian stem cells using the methods as disclosed herein, for example the MTT assay or CFU assay, and an agent identified to decrease the rate of proliferation and/or attenuate proliferation by about 10%, or about 20% or about 30% or greater than 30% and/or kill about 10% or about 20% or about 30% or greater than 30% of the population of ovarian cancer stem cells as compared to a population of somatic ovarian stem cells identifies an agent that is useful for a therapy for the treatment of ovarian cancer. Effectively, the assay as disclosed herein can be used to identify agents that selectively inhibit the 3+/ECad− ovarian cancer stem cells as compared to 3+/Ecad+ cells, or coelomic ovarian stem cell population. Agents useful in such an embodiment can be any agent as disclosed herein under the term "agent" in the definitions section, and can be for example nucleic acid agents, such as RNAi agents (RNA interference agents), nucleic acid analogues, small molecules, proteins, peptiomimetics, antibodies, peptides, aptamers, ribozymes, and variants, analogues and fragments thereof.

In further embodiments, the CD44+, CD24+, EpCam+, ECad− (e.g., 3+/ECad−) ovarian cancer stem cells identified using the methods as disclosed herein can be used in assay to for the study and understanding of signalling pathways of ovarian cancer stem cells. The use of CD44+, CD24+, EpCam+, ECad− (e.g., 3+/ECad−) ovarian cancer stem cell as disclosed herein is useful to aid the development of therapeutic applications for ovarian cancers. The use of such CD44+, CD24+, EpCam+, ECad− (e.g., 3+/ECad−) ovarian cancer stem cells identified using the methods as disclosed herein enable the study of ovarian cancers. For example, the CD44+, CD24+, EpCam+, ECad− (e.g., 3+/ECad−) ovarian cancer stem cells can be used for generating animal models of ovarian cancer as described in the Examples herein, which can be used for an assay to test for therapeutic agents that inhibit the proliferation of ovarian cancer stem cells. Such a model us also useful in aiding the understanding of ovarian cancer stem cells in the development of ovarian cancer.

The CD44+, CD24+, EpCam+, ECad− (e.g., 3+/ECad−) ovarian cancer stem cells can be used to identify additional markers that characterize them as ovarian cancer stem cells as compared to 3+/ECad+ cells, or non-stem ovarian cancer cells and/or somatic ovarian stem cells, such as coelomic ovarian stem cell populations and/or subcoelomic/stromal ovarian stem cell populations and periphilar medullary ovarian stem cell populations. Such markers can be cell-surface markers or surface markers or other markers, for example mRNA or protein markers intracellular within the cell. Such markers can be used as additional agents in the diagnosis of ovarian cancer stem cells in subjects with ovarian cancers.

In further embodiments, the 3+/ECad− ovarian cancer stem cells as disclosed herein can be used to prepare antibodies that are specific markers of 3+/ECad− ovarian cancer stem cells. Polyclonal antibodies can be prepared by injecting a vertebrate animal with cells of this invention in an immunogenic form. Production of monoclonal antibodies is described in such standard references as U.S. Pat. Nos. 4,491,632, 4,472,500 and 4,444,887, and Methods in Enzymology 73B:3 (1981). Specific antibody molecules can also be produced by contacting a library of immunocompetent cells or viral particles with the target antigen, and growing out positively selected clones. See Marks et al., New Eng. J. Med. 335:730, 1996, and McGuiness et al., Nature Biotechnol. 14:1449, 1996. A further alternative is reassembly of random DNA fragments into antibody encoding regions, as described in EP patent application 1,094,108 A.

The antibodies in turn can be used as diagnostic applications to identify a subject with ovarian cancer comprising 3+/ECad− ovarian cancer stem cells, or alternatively, antibodies can be used as therapeutic agents to prevent the proliferation and/or kill the 3+/ECad− ovarian cancer stem cells.

In another embodiment, the 3+/ECad− ovarian cancer stem cells as disclosed herein can be used to prepare a cDNA library of relatively uncontaminated with cDNAs that are preferentially expressed in 3+/ECad− ovarian cancer stem cells as compared to somatic ovarian stem cells and/or non-stem ovarian cancer cells. For example, 3+/ECad− ovarian cancer stem cells are collected and then mRNA is prepared from the pellet by standard techniques (Sambrook et al., supra). After reverse transcribing the cDNA, the preparation can be subtracted with cDNA from, for example non-stem cell ovarian cancer cells or non-cancer ovarian cells in a subtraction cDNA library procedure. Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+mRNA. One of skill in the art can readily use these methods to determine differences in the molecular size or amount of mRNA transcripts between two samples.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., Science (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. No. 5,776,683; and U.S. Pat. No. 5,807,680. Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Hybridization to arrays may be performed, where the arrays can be produced according to any suitable methods known in the art. For example, methods of producing large arrays of oligonucleotides are described in U.S. Pat. No. 5,134,854, and U.S. Pat. No. 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505. Methods for collection of data from hybridization of samples with an array are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., Genome Res. (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes. Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992. General methods in molecular and cellular biochemistry can also be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Computer Systems

In some embodiments, the methods and assay can be carried out in an automated and/or high-throughput system. One aspect of the present invention relates to a computerized system for processing the assays as disclosed herein and identifying the presence of 3+/Ecad− cells in a biological sample. In some embodiments, a computer system can include: (a) at least one memory containing at least one computer program adapted to control the operation of the computer system to implement a method that includes: (i) receiving data of the level of expression or intensity of signal of measured CD44, CD24, EpCam and Ecad (ii) generating a report of intensity of expression or intensity of signal of measured CD44, CD24, EpCam and Ecad in a cell population and optionally a reference level for CD44, CD24, EpCam and Ecad signal intensity; and (b) at least one processor for executing the computer program.

Another aspect of the present invention relates to a computer readable medium comprising instructions, such as computer programs and software, for controlling a computer system to process the data from signal intensity of measured CD44, CD24, EpCam and Ecad expression and generate a report of the presence or absence, or amount of 3+/Ecad− cells in the biological sample.

The computer system can include one or more general or special purpose processors and associated memory, including volatile and non-volatile memory devices. The computer system memory can store software or computer programs for controlling the operation of the computer system to make a special purpose computer system according to the invention or to implement a system to perform the methods and analysis according to the invention.

In some embodiments, a computer system can include, for example, an Intel or AMD x86 based single or multi-core central processing unit (CPU), an ARM processor or similar computer processor for processing the data. The CPU or microprocessor can be any conventional general purpose single- or multi-chip microprocessor such as an Intel and AMD processor, a SPARC processor, or an ARM processor. In addition, the microprocessor may be any conventional or special purpose microprocessor such as a digital signal processor or a graphics processor. The microprocessor typically has conventional address lines, conventional data lines, and one or more conventional control lines. As described below, the software according to the invention can be executed on dedicated system or on a general purpose computer having a DOS, CPM, Windows, Unix, Linux or other operating system. The system can include non-volatile memory, such as disk memory and solid state memory for storing computer programs, software and data and volatile memory, such as high speed ram for executing programs and software.

Computer-readable physical storage media useful in various embodiments of the invention can include any physical computer-readable storage medium, e.g., solid state memory (such as flash memory), magnetic and optical computer-readable storage media and devices, and memory that uses other persistent storage technologies. In some embodiments, a computer readable media can be any tangible media that allows computer programs and data to be accessed by a computer. Computer readable media can include volatile and nonvolatile, removable and non-removable tangible media implemented in any method or technology capable of storing information such as computer readable instructions, program modules, programs, data, data structures, and database information. In some embodiments of the invention, computer readable media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks), Blue-ray, USB drives, micro-SD drives, or other optical storage media, magnetic cassettes, magnetic tape, magnetic disk storage or other magnetic storage media, other types of volatile and non-volatile memory, and any other tangible medium which can be used to store information and which can read by a computer including and any suitable combination of the foregoing.

The present invention can be implemented on a stand-alone computer or as part of a networked computer system. In a stand-alone computer, all the software and data can reside on local memory devices, for example an optical disk or flash memory device can be used to store the computer software for implementing the invention as well as the data. In alternative embodiments, the software or the data or both can be accessed through a network connection to remote devices. In one embodiment, the invention can use a client-server environment over a network, e.g., a public network such as the internet or a private network to connect to data and resources stored in remote and/or centrally located locations. In this embodiment, a server such as a web server can provide access, either open access, pay as you go or subscription based access to the information provided according to the invention. In a client server environment, a client computer executing a client software or program, such as a web browser, connects to the server over the network. The client software provides a user interface for a user of the invention to input data and information and receive access to data and information. The client software can be viewed on a local computer display or other output device and can allow the user to input information, such as by using a computer keyboard, mouse or other input device. The server executes one or more computer programs that receives data input through the client software, processes data according to the invention and outputs data to the user, as well as provide access to local and remote computer resources. For example, the user interface can include a graphical user interface comprising an access element, such as a text box, that permits entry of data from the assay, e.g., the data from a positive reference cancer cell, as well as a display element that can provide a graphical read out of the results of a comparison with a cancer cell with a known metastatic potential or invasive capacity, or data sets transmitted to or made available by a processor following execution of the instructions encoded on a computer-readable medium.

Embodiments of the invention also provide for systems (and computer readable medium providing instructions for causing computer systems) to perform a method for determining quality assurance of a pluripotent stem cell population according to the methods as disclosed herein.

In some embodiments of the invention, the computer system software can include one or more functional modules, which can be defined by computer executable instructions recorded on computer readable media and which cause a computer to perforin, when executed, a method according to one or more embodiments of the invention. The modules can be segregated by function for the sake of clarity, however, it should be understood that the modules need not correspond to discreet blocks of code and the described functions can be carried out by the execution of various software code portions stored on various media and executed at various times. Furthermore, it should be appreciated that the modules can perform other functions, thus the modules are not limited to having any particular function or set of functions. In some embodiments, functional modules are, for example, but are not limited to, an array module, a determination module, a storage module, a reference comparison module, a normalization module, and a display module to display the results (e.g., the invasive potential of the test cancer cell population). The functional modules can be executed using one or multiple computers, and by using one or multiple computer networks.

The information embodied on one or more computer-readable media can include data, computer software or programs, and program instructions, that, as a result of being executed by a computer, transform the computer to special purpose machine and can cause the computer to perform one or more of the functions described herein. Such instructions can be originally written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied can reside on one or more of the components of a computer system or a network of computer systems according to the invention.

In some embodiments, a computer-readable media can be transportable such that the instructions stored thereon can be loaded onto any computer resource to implement the aspects of the present invention discussed herein. In addition, it should be appreciated that the instructions stored on computer readable media are not limited to instructions embodied as part of an application program running on a host computer. Rather, the instructions may be embodied as any type of computer code (e.g., object code, software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

In some embodiments, a system as disclosed herein, can receive data of intensity of expression of CD44, CD24, EpCam and ECad from any method of determining the level of expression. Where the amount of cells is measured by protein expression, the system as disclosed herein can be configured to receive data from an automated protein analysis systems, for example, using immunoassay, for example western blot analysis or ELISA, or a high through-put protein detection method, for example but are not limited to automated immunohistochemistry apparatus, for example, robotically automated immunodetection apparatus which in an automated system can perform immunohistochemistry procedure and detect intensity of immunostaining, such as intensity of an antibody staining of the substrates and produce output data. Examples of such automated immunohistochemistry apparatus are commercially available, and can be readily adapted to automatically detect the level of protein expression in the assay as disclosed herein, and include, for example but not limited to such Autostainers 360, 480, 720 and Labvision PT module machines from LabVision Corporation, which are disclosed in U.S. Pat. Nos. 7,435,383; 6,998,270; 6,746,851, 6,735,531; 6,349, 264; and 5,839; 091 which are incorporated herein in their entirety by reference. Other commercially available automated immunohistochemistry instruments are also encompassed for use in the present invention, for example, but not are limited BOND™ Automated Immunohistochemistry & In Situ Hybridization System, Automate slide loader from GTI vision. Automated analysis of immunohistochemistry can be performed by commercially available systems such as, for example, IHC Scorer and Path EX, which can be combined with the Applied spectral Images (ASI) CytoLab view, also available from GTI vision or Applied Spectral Imaging (ASI) which can all be integrated into data sharing systems such as, for example, Laboratory Information System (LIS), which incorporates Picture Archive Communication System (PACS), also available from Applied Spectral Imaging (ASI) (see world-wide-web: spectral-imaging.com). Other a determination module can be an automated immunohistochemistry systems such as NexES® automated immunohistochemistry (IHC) slide staining system or BenchMark® LT automated IHC instrument from Ventana Discovery SA, which can be combined with VIAS™ image analysis system also available Ventana Discovery. BioGenex Super Sensitive MultiLink® Detection Systems, in either manual or automated protocols can also be used as the detection module, preferably using the BioGenex Automated Staining Systems. Such systems can be combined with a BioGenex automated staining systems, the i6000™ (and its predecessor, the OptiMax® Plus), which is geared for the Clinical Diagnostics lab, and the GenoMx 6000™, for Drug Discovery labs. Both systems BioGenex systems perform "All-in-One, All-at-Once" functions for cell and tissue testing, such as Immunohistochemistry (IHC) and In Situ Hybridization (ISH).

In some embodiments, a system as disclosed herein, can receive data of intensity of expression of CD44, CD44, EpCam, ECad from an automated ELISA system (e.g. DSX® or DK® form Dynax, Chantilly, Va. or the ENEA-SYSTEM III®, Triturus®, The Mago® Plus); Densitometers (e.g. X-Rite-508-Spectro Densitometer®, The HYRYS™ 2 densitometer); automated Fluorescence in situ hybridization systems (see for example, U.S. Pat. No. 6,136, 540); 2D gel imaging systems coupled with 2-D imaging software; microplate readers; Fluorescence activated cell sorters (FACS) (e.g. Flow Cytometer FACSVantage SE, Becton Dickinson); radio isotope analyzers (e.g. scintillation counters), or adapted systems thereof for detecting cells on the separated substrates as disclosed herein.

In some embodiments, a system as disclosed herein, can receive data can receive data of intensity of expression of CD44, CD44, EpCam, ECad from any method of determining gene expression. In some embodiments, the system as disclosed herein can be configured to receive data from an automated gene expression analysis system, e.g., an automated protein expression analysis including but not limited Mass Spectrometry systems including MALDI-TOF, or Matrix Assisted Laser Desorption Ionization—Time of Flight systems; SELDI-TOF-MS ProteinChip array profiling systems, e.g. Machines with Ciphergen Protein Biology System II™ software; systems for analyzing gene expression data (see for example U.S. 2003/0194711); systems for array based expression analysis, for example HT array systems and cartridge array systems available from Affymetrix (Santa Clara, Calif. 95051) AutoLoader, Complete GeneChip® Instrument System, Fluidics Station 450, Hybridization Oven 645, QC Toolbox Software Kit, Scanner 3000 7G, Scanner 3000 7G plus Targeted Genotyping System, Scanner 3000 7G Whole-Genome Association System, GeneTitan™ Instrument, GeneChip® Array Station, HT Array.

In some embodiments of the present invention, an automated gene expression analysis system can record the data electronically or digitally, annotated and retrieved from databases including, but not limited to GenBank (NCBI) protein and DNA databases such as genome, ESTs, SNPS, Traces, Celara, Ventor Reads, Watson reads, HGTS, etc.; Swiss Institute of Bioinformatics databases, such as ENZYME, PROSITE, SWISS-2DPAGE, Swiss-Prot and TrEMBL databases; the Melanie software package or the ExPASy WWW server, etc., the SWISS-MODEL, Swiss-Shop and other network-based computational tools; the Comprehensive Microbial Resource database (The institute of Genomic Research). The resulting information can be stored in a relational data base that may be employed to determine homologies between the reference data or genes or proteins within and among genomes.

In some embodiments, the data of intensity of expression of CD44, CD44, EpCam, ECad can be received from a memory, a storage device, or a database. The memory, storage device or database can be directly connected to the computer system retrieving the data, or connected to the computer through a wired or wireless connection technology and retrieved from a remote device or system over the wired or wireless connection. Further, the memory, storage device or database, can be located remotely from the computer system from which it is retrieved.

Examples of suitable connection technologies for use with the present invention include, for example parallel interfaces (e.g., PATA), serial interfaces (e.g., SATA, USB, Firewire,), local area networks (LAN), wide area networks (WAN), Internet, Intranet, and Extranet, and wireless (e.g., Blue Tooth, Zigbee, WiFi, WiMAX, 3G, 4G) communication technologies Storage devices are also commonly referred to in the art as "computer-readable physical storage media" which is useful in various embodiments, and can include any physical computer-readable storage medium, e.g., magnetic and optical computer-readable storage media, among others. Carrier waves and other signal-based storage or transmission media are not included within the scope of storage devices or physical computer-readable storage media encompassed by the term and useful according to the invention. The storage device is adapted or configured for having recorded thereon cytokine level information. Such information can be provided in digital form that can be transmitted and read electronically, e.g., via the Internet, on diskette, via USB (universal serial bus) or via any other suitable mode of communication.

As used herein, "stored" refers to a process for recording information, e.g., data, programs and instructions, on the storage device that can be read back at a later time. Those skilled in the art can readily adopt any of the presently known methods for recording information on known media to contribute to the data of the amount of cells on a receiving substrate and/or amount of cells on a seed-substrate a reference scorecard data, e.g., data of an amount of cells on a receiving substrate from a biological sample obtained from the same subject (e.g., obtained from the subject at an earlier timepoint) and/or amount of cells from one or more reference cancer cell lines as disclosed in the methods herein.

A variety of software programs and formats can be used to store information on the storage device. Any number of data processor structuring formats (e.g., text file or database) can be employed to obtain or create a medium having recorded scorecard thereon.

In some embodiment, the system has a processor for running one or more programs, e.g., where the programs can include an operating system (e.g., UNIX, Windows), a relational database management system, an application program, and a World Wide Web server program. The application program can be a World Wide Web application that includes the executable code necessary for generation of database language statements (e.g., Structured Query Language (SQL) statements). The executables can include embedded SQL statements. In addition, the World Wide Web application can include a configuration file which contains pointers and addresses to the various software entities that provide the World Wide Web server functions as well as the various external and internal databases which can be accessed to service user requests. The Configuration file can also direct requests for server resources to the appropriate hardware devices, as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

In one embodiment, the system as disclosed herein can be used to compare the data of intensity of expression of CD44, CD44, EpCam, ECad with reference data.

In some embodiments of this aspect and all other aspects of the present invention, the system can compare the data in a "comparison module" which can use a variety of available software programs and formats for the comparison operative to compare sequence information determined in the determination module to reference data. In one embodiment, the comparison module is configured to use pattern recognition techniques to compare sequence information from one or more entries to one or more reference data patterns. The comparison module may be configured using existing commercially-available or freely-available software for comparing patterns, and may be optimized for particular data comparisons that are conducted. The comparison module can also provide computer readable information related to the level or amount of intensity of expression of CD44, CD44, EpCam, ECad and the like as disclosed herein.

By providing data of the intensity of expression of CD44, CD44, EpCam, ECad in computer-readable form, one can use the data to compare with data within the storage device. For example, search programs can be used to identify relevant reference data (i.e. data of appropriate reference cancer cell lines) that match the same type of cancer as the cancer of the test cancer cell population. The comparison made in computer-readable form provides computer readable content which can be processed by a variety of means. The content can be retrieved from the comparison module, the retrieved content.

In some embodiments, the comparison module provides computer readable comparison result that can be processed in computer readable form by predefined criteria, or criteria defined by a user, to provide a report which comprises content based in part on the comparison result that may be stored and output as requested by a user using a display module. In some embodiments, a display module enables display of a content based in part on the comparison result for the user, wherein the content is a report indicative of the results of the comparison of the intensity of expression of CD44, CD44, EpCam, ECad with respective reference values for CD44, CD44, EpCam, ECad or a negative reference cell line (e.g., 3+/Ecad+ cells) or a positive reference cell line (e.g., 3+/Ecad–) cells.

In some embodiments, the display module enables display of a report or content based in part on the comparison result for the end user, wherein the content is a report indicative of the results of the comparison of the intensity of expression of CD44, CD44, EpCam, ECad with a reference value, and/or as a comparison with known 3+/Ecad+ cells and/or with known 3+/Ecad– cells.

In some embodiments of this aspect and all other aspects of the present invention, the comparison module, or any other module of the invention, can include an operating system (e.g., UNIX, Windows) on which runs a relational database management system, a World Wide Web application, and a World Wide Web server. World Wide Web application can includes the executable code necessary for generation of database language statements [e.g., Standard Query Language (SQL) statements]. The executables can include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using an HTML interface provided by Web browsers and Web servers. In other embodiments of the invention, other interfaces, such as HTTP, FTP, SSH and VPN based interfaces can be used to connect to the Internet databases.

In some embodiments of this aspect and all other aspects of the present invention, a computer-readable media can be transportable such that the instructions stored thereon, such as computer programs and software, can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a processor to implement aspects of the present invention. The computer executable instructions can be written in a suitable computer language or combination of several languages. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The computer instructions can be implemented in software, firmware or hardware and include any type of programmed step undertaken by modules of the information processing system. The computer system can be connected to a local area network (LAN) or a wide area network (WAN). One example of the local area network can be a corporate computing network, including access to the Internet, to which computers and computing devices comprising the data processing system are connected. In one embodiment, the LAN uses the industry standard Transmission Control Protocol/Internet Protocol (TCP/IP) network protocols for communication. Transmission Control Protocol Transmission Control Protocol (TCP) can be used as a transport layer protocol to provide a reliable, connection-oriented, transport layer link among computer systems. The network layer provides services to the transport layer. Using a two-way handshaking scheme, TCP provides the mechanism for establishing, maintaining, and terminating logical connections among computer systems. TCP transport layer uses IP as its network layer protocol. Additionally, TCP provides protocol ports to distinguish multiple programs executing on a single device by including the destination and source port number with each message. TCP performs functions such as transmission of byte streams, data flow definitions, data acknowledgments, lost or corrupt data re-transmissions, and multiplexing multiple connections through a single network connection. Finally, TCP is responsible for encapsulating information into a datagram structure. In alternative embodiments, the LAN can conform to other network standards, including, but not limited to, the International Standards Organization's Open Systems Interconnection, IBM's SNA, Novell's Netware, and Banyan VINES.

In some embodiments, the computer system as described herein can include any type of electronically connected group of computers including, for instance, the following networks: Internet, Intranet, Local Area Networks (LAN) or Wide Area Networks (WAN). In addition, the connectivity to the network may be, for example, remote modem, Ethernet (IEEE 802.3), Token Ring (IEEE 802.5), Fiber Distributed Datalink Interface (FDDI) or Asynchronous Transfer Mode (ATM). The computing devices can be desktop devices, servers, portable computers, hand-held computing devices, smart phones, set-top devices, or any other desired type or configuration. As used herein, a network includes one or more of the following, including a public internet, a private internet, a secure internet, a private network, a public network, a value-added network, an intranet, an extranet and combinations of the foregoing.

In one embodiment of the invention, the computer system can comprise a pattern comparison software can be used to determine whether the patterns of data of the intensity of expression of CD44, CD44, EpCam, ECadare indicative of that cancer population comprising 3+/Ecad– ovarian cancer cells. In this embodiment, the pattern comparison software can compare at least some of the data (e.g., data of intensity of expression of CD44, CD44, EpCam, ECad) with reference data (e.g., data of the intensity of expression of CD44, CD44, EpCam, ECad for 3+/Ecad– cells) to determine how closely they match. The matching can be evaluated and reported in portions or degrees indicating the extent to which all or some of the pattern matches.

In some embodiments of this aspect and all other aspects of the present invention, a comparison module provides computer readable data that can be processed in computer readable form by predefined criteria, or criteria defined by a user, to provide a retrieved content that may be stored and output as requested by a user using a display module.

Output Module

In accordance with some embodiments of the invention, the computerized system can include or be operatively connected to an output module. In some embodiments, the output module is a display module, such as computer monitor, touch screen or video display system. The display module allows user instructions to be presented to the user of the system, to view inputs to the system and for the system to display the results to the user as part of a user interface. Optionally, the computerized system can include or be operative connected to a printing device for producing printed copies of information output by the system.

In some embodiments, the results can be displayed on a display module or printed in a report, e.g., a to indicate the presence (or absence) of 3+/Ecad− cells and/or the percentage of cells which are 3+/Ecad− or any other report envisioned by the end user.

In some embodiments, the report is a hard copy printed from a printer. In alternative embodiments, the computerized system can use light or sound to report the result, e.g., to indicate the presence of 3+/Ecad− cells in the cancer cell population. For example, in all aspects of the invention, the report produced by the methods, assays, systems and kits as disclosed herein can comprise a report which is color coded to signal or indicate the presence of 3+/Ecad− cells, or compared another "gold" standard of presence of 3+/Ecad-0 cells in a reference control ovarian cell line of the investigators choice.

For example, a red color or other predefined signal can indicate that the test cancer cell population has presence of 3+/Ecad− cells. In another embodiment, a green color or other predefined signal can indicate that the test cancer cell population does not have presence of 3+/Ecad− cells. In some embodiments, a "heat map" or gradient color scheme can be used in the report to signal the % of 3+/Ecad− cells in the test cell population where for example, the gradient is a red to yellow to green gradient, where a red signal will signal high presence or % of 3+/Ecad− cells, and a yellow signal will indicate a low levels or low % of 3+/Ecad− cells and a green signal will indicate absence of 3+/Ecad− cells. Typically, a gradient, whether using arbitrary numerical scale or a color gradient is based upon one or more reference cancer cell lines. Other color schemes and gradient schemes in the report are also encompassed.

In some embodiments, the report can display the % of 3+/Ecad− cells, and/or absolute amount of 3+/Ecad− cells on the receiving substrate, or a numerical number grade or % value as compared with a reference 3+/Ecad− positive cancer cell line or a negative reference cancer cell line.

In some embodiments, the report can display the normalized values of the test cancer cell population, which are normalized to a reference positive 3+/Ecad− cancer cell line (e.g., a selected "gold" standard cell line of the investigators choice). Accordingly, a report can display the % difference, and/or the change in absolute number of amount of 3+/Ecad− cells as compared to the absolute amount of 3+/Ecad− cells.

In some embodiments, the report can be color-coded, for instance, if the % or absolute number of 3+/Ecad− cells in the test cancer cell sample is above a certain pre-defined threshold level, the color of the % value or absolute number of cells can be a bright color (e.g., red), or otherwise marked (e.g. by a *) or highlighted for easy identification that this value indicates that the cancer cell population comprises a population of 3+/Ecad− ovarian cancer cells. The predefined threshold level is determined by the investigator, and is typically determined by a comparison of the values for the % and absolute number of cells of reference 3+/Ecad− positive cancer cell line.

In some embodiments, the report can also display the reference values of reference cancer cell line. In some embodiments, reference values for at least one positive 3+/Ecad− reference cancer line is shown. In some embodiments, reference values for at least one negative 3+/Ecad+ reference cancer line is shown. Such reference values can be used to compare with the values from the test cancer cell population.

In some embodiments, the report can also present text, either verbally or written, giving a recommendation of the presence of 3+/Ecad− cells in the cancer cell population. In other embodiments, the report provides just values or numerical scores for the presence of 3+/Ecad− cells which can be readily compared by a physician with reference values as disclosed herein.

In some embodiments of this aspect and all other aspects of the present invention, the report data from the comparison module can be displayed on a computer monitor as one or more pages of the printed report. In one embodiment of the invention, a page of the retrieved content can be displayed through printable media. The display module can be any device or system adapted for display of computer readable information to a user. The display module can include speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc In some embodiments of the present invention, a World Wide Web browser can be used to provide a user interface to allow the user to interact with the system to input information, construct requests and to display retrieved content. In addition, the various functional modules of the system can be adapted to use a web browser to provide a user interface. Using a Web browser, a user can construct requests for retrieving data from data sources, such as data bases and interact with the comparison module to perform comparisons and pattern matching. The user can point to and click on user interface elements such as buttons, pull down menus, scroll bars, etc. conventionally employed in graphical user interfaces to interact with the system and cause the system to perform the methods of the invention. The requests formulated with the user's Web browser can be transmitted over a network to a Web application that can process or format the request to produce a query of one or more database that can be employed to provide the pertinent information related to the tumor type, the retrieved content, process this information and output the results, e.g. at least one of any of the following: % invasion, % invasion under specific conditions (e.g., culture time, presence of drugs, tumor of different geometry, e.g., with or without hypoxic cells). In some embodiments, these values or their combination can exhibit strong correlation with invasive capacity of cells in the patients. In some embodiments, output information of the % invasion, % invasion under specific conditions (e.g., culture time, presence of drugs, tumor of different geometry, e.g., with or without hypoxic cells) can vary with different tumor types, and can be determined by one of ordinary skill in the art by comparing the numbers across a range of highly metastatic cancer cell lines as disclosed herein.

Some embodiments of the present invention may be defined in any of the following numbered paragraphs:

1. A method to identify a ovarian cancer stem cell in a population of cells, comprising measuring the expression of CD24, CD44, EpCam and E-Cadherin in a cell, wherein if a cell is positive for the expression of CD24, CD44, EpCam and negative for the expression of E-Cadherin, the cell is identified as an ovarian cancer stem cell.
2. A method to isolate a population of ovarian cancer stem cells in a population of cells, comprising:
    measuring the expression of CD24, CD44, EpCam in a cell, and selecting the cells which are positive for expression of CD24, CD44, EpCam, and
    measuring the expression product of E-Cadherin in the selected cells and selecting for the cells which are negative for the expression of E-Cadherin,
    wherein the selected cells which are positive for the expression of CD24, CD44, EpCam and negative for the expression of E-Cadherin are an isolated a population of ovarian cancer stem cells.
3. The method of paragraph 1 or 2, wherein the ovarian cancer stem cells are responsive to inhibition of proliferation by MIS or a mimetic thereof
4. The method of claim 1, wherein the ovarian cancer stem cells are resistant to chemotherapeutic agents.
5. The method of paragraph 4, wherein the chemotherapeutic agent is selected from the group consisting of: Dexorubicin, taxol, cisplatin, paclitaxel and derivatives thereof
6. The method of any of paragraphs 1 to 5, wherein the population of cells is in a biological sample, wherein the biological sample comprises any of the group consisting of: ovarian cells, ascites, ovarian cell line, ovarian cancer biopsy sample.
7. An assay for detecting the presence of ovarian cancer stem cells in a biological sample, the assay comprising:
    (a) transforming the expression of CD24, CD44, EpCam and E-Cadherin in ovarian cells in a biological sample into detectable targets;
    (b) measuring the level of the detectable targets;
    wherein the presence of detectable targets for CD24, CD44, EpCam and the absence of detectable targets for E-Cadherin in indicates the presence of ovarian cancer stem cells in a biological sample.
8. An assay comprising:
    (a) contacting a biological sample from a subject with at least one detectable antibody specific to CD44, CD24, EpCam and Ecadherin;
    (b) washing the sample to remove unbound antibodies,
    (c) measuring the intensity of the signal from the bound, detectable antibody to CD44, CD24, EpCam and E-cadherin,
    (d) comparing the measured intensity of the signal of CD44, CD24, EpCam and Ecadherin to a reference value, and if there is a measured intensity of CD44, CD24, EpCam and Ecadherin is increased relative to a reference value, and
    (e) identifying the subject has having increased probability of having chemotherapeutic resistant ovarian cancer.
9. An assay comprising:
    (a) contacting a biological sample from a subject with at least one detectable antibody specific to CD44, CD24, and EpCam
    (b) washing the sample to remove unbound antibodies,
    (c) selecting for cells where the intensity of the signal from the bound, detectable antibody to CD44, CD24, EpCam is above a reference level,
    (d) contacting the cells from step (c) with a detectable antibody specific to Ecadherin,
    (e) washing the sample to remove unbound antibodies,
    (f) selecting for cells where the intensity of the signal from the bound, detectable antibody to Ecadherin is below a reference level,
    (g) identifying the subject has having increased probability of having chemotherapeutic resistant ovarian cancer where the cells selected have the intensity of Ecadherin below a reference level.
10. The assays of any of paragraphs 6 to 9 wherein the biological sample comprises any cells from any one selected from the group consisting of: ovarian cells, ovarian cancer biopsy cells, primary ascites, ovarian cell line.
11. A method of treating a subject with ovarian cancer comprising administering a pharmaceutically effective amount of MIS or a MIS mimetic to the subject having ovarian cancer, wherein the ovarian cancer is determined to comprise a population of the CD44+/CD24+/EpCam+/Ecad– cells, and wherein the subject is not administered an effective amount of a chemotherapeutic agent if said subject is determined to have CD44+/CD24+/EpCam+/ECad– cells.
12. The method of paragraph 11, wherein the MIS is recombinant human MIS (rhMIS) or a pro-hormone or homodimer thereof
13. The method of any of paragraphs 11 to 12, wherein a MIS mimetic is SP600125 or a derivative thereof
14. The method of any of paragraphs 11 to 13, wherein the subject is a mammalian subject.
15. The method of any of paragraphs 11 to 14, wherein the subject is a human subject.
16. A method of determining if a subject is responsive to MIS or a MIS mimetic comprising assaying a biological sample from the subject for the presence of CD44+/CD24+/Epcam+/Ecad– cells, wherein MIS or a MIS mimetic is administered to a subject if CD44+/CD24+/EpCam+/Ecad– cells are present, and administering to the subject a chemotherapeutic agent if CD44+/CD24+/EpCam+/ECad– cells are absent.
17. A method to determine if a subject with ovarian cancer can be treated with a chemotherapeutic, the method comprising assaying a biological sample from the subject for the presence of CD44+/CD24+/Epcam+/Ecad– cells, wherein administering to the subject a chemotherapeutic agent if CD44+/CD24+/EpCam+/ECad– cells are absent.
18. A method of determining if a subject with ovarian cancer has an increased probability of being resistant to chemotherapeutics, comprising assaying a biological sample from the subject for the presence of CD44+/CD24+/Epcam+/Ecad– cells, the presence of CD44+/CD24+/EpCam+/ECad– cells indicates the subject has increased probability of being resistant to chemotherapeutics.
19. The method of any of any of paragraphs 16 to 18, wherein the population of cells is in a biological sample, wherein the biological sample comprises any of the group consisting of: ovarian cells, ascites, ovarian cell line, ovarian cancer biopsy sample.
20. An isolated population of ovarian cancer stem cells, wherein the ovarian cancer stem cells are positive for the expression of CD24, CD44, EpCam and negative for the expression of E-Cadherin.

21. The population of paragraph 20, wherein the ovarian cancer stem cells are further positive for the expression of Lin28.
22. The population of any of paragraphs 20 to 21, wherein the ovarian cancer stem cells are mammalian ovarian cancer stem cells.
23. The population of any of paragraphs 20 to 22, wherein the mammalian ovarian cancer stem cells are human ovarian cancer stem cells.
24. The population of any of any of paragraphs 20 to 23, wherein the ovarian cancer stem cells are identified or isolated according to any of the claims 1 to 5.
25. The population of any of any of paragraphs 20 to 24, wherein the ovarian cancer stem cells are used in the assay according to claims 7 to 10.
26. Use of the isolated population of CD44+/CD24+/EpCam+/ECad− ovarian cancer stem cells in an assay to identify an agent which inhibits the proliferation of said CD44+/CD24+/EpCam+/ECad− ovarian cancer stem cells population of cells, comprising;
    (a) contacting the isolated population of CD44+/CD24+/EpCam+/ECad− ovarian cancer stem cells with at least one agent; and
    (b) measuring the proliferation of the population of CD44+/CD24+/EpCam+/ECad− ovarian cancer stem cells in the presence and absence of the agent, wherein an decrease in the proliferation in the population of cells in the presence of the agent as compared to the absence, identifies an agent which inhibits the proliferation of ovarian cancer stem cells.
27. The use of paragraph 26, wherein the proliferation is measured by colony formation assay.
28. A method for screening potential ovarian cancer therapeutics which comprises:
    (a) growing CD44+/CD24+/EpCam+/ECad− ovarian cancer stem cells in the presence of a compound suspected as being a chemotherapeutic,
    (b) growing said CD44+/CD24+/EpCam+/ECad− ovarian cancer stem cell in the absence of said compound,
    (c) determining the rate of growth of said CD44+/CD24+/EpCam+/ECad− cells in the presence of said compound and the rate of said CD44+/CD24+/EpCam+/ECad− ovarian cancer cells in the absence of said compound, and
    (d) comparing the growth rate of said CD44+/CD24+/EpCam+/ECad− cells,
wherein a slower rate of growth of said CD44+/CD24+/EpCam+/ECad− cell in the presence of said compound is indicative of a ovarian cancer therapeutic.

Having generally described this invention, the same will become more readily understood by reference to the following specific examples which are included herein for purposes of illustration only and are not intended to be limiting unless otherwise specified.

EXAMPLES

The examples presented herein relate to the methods of prevention and/or treatment of ovarian cancer, for example in subjects that have ovarian cancer comprising CD44+, CD24+, EpCam+, ECad− (e.g., 3+/ECad−) ovarian cancer stem cells. Methods as disclosed herein provide treatment of ovarian cancer by targeting CD44+, CD24+, EpCam+, ECad− (e.g., 3+/ECad−) ovarian cancer stem cells with MIS or derivatives or variants thereof. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Materials and Methods

Cell Lines, Reagents, and MIS.

The mouse ovarian cancer cell line MOVCAR-8 (D. Connolly et al, 2003) cells, and human ovarian cancer cell lines, OVCAR-5 (55, 56), and SKOV-3 (57, 58) cells were maintained in the Pediatric Surgical Research Laboratories as previously described (4, 21, Wei 2010). Cells were treated with doxorubicin (DOX) (NovaPlus, Irving Tex.), cisplatin, taxol or Müllerian Inhibiting Substance (MIS). MIS was produced in serum free media in suspension culture in an 80 liter bioreactor in a collaboration with IPSEN BioMeasure (Milford, Mass.) and immunoaffinity purified using a mouse monocloncal antibody scaledin our laboratory (Ragin et al, 1992), and its bioactivity assessed in embryonic Müllerian duct regression assays as previously described (60, 61). The treatment doses were selected based on previous studies in the laboratory (21, Wei 2010).

Harvesting of Primary Human Ovarian Cancer Ascites.

Primary ascites removed therapeutically from patients with ovarian cancer at the Massachusetts General Hospital (IRB #2007-P-001918) were centrifuged at 1800 rpm for 20 min. Cells were then resuspended in DMEM/F-12 medium, filtered using a sterile cell strainer (70 µm Nylon Mesh; Fisher Scientific), centrifuged at 1500 rpm for 5 min, resuspended with ammonium chloride solution to lyse red blood cells, diluted with DMEM/F-12 medium, and recentrifuged. Cells were then twice washed in the same media, stained with antibodies for 20 min at 4° C., washed again, and resuspended in PBS for immediate flow analysis or Fluorescent Activated Cell Sorting (FACS).

To examine time to appearance of tumors, NOD/SCID 6 week old female mice were injected with 100 and 1000 3+/Ecad− OVCAR-5 cells in the right flank and compared to 3−/Ecad+ cells injected at the same numbers into the left flank of the same mouse.

Flow Cytometry or Fluorescent Activated Cell Sorting (FACS).

Flow cytometry was performed in the MGH Department of Pathology and Center for Regenerative Medicine Flow Cytometry Laboratory using the Flow Analyzer LSRII (BD Science) or Flow Sorter (BD Science) as previously described (4; wei 2010). Ovarian cancer cell lines or ascites were stained with anti-human CD24-PE (e-Bioscience), anti-mouse/human CD44-APC/Cy7, Epcam-APC (BioLegend), and anti-human E-cadherin-FITC (CD324; BioLegend) for 30 min at 4° C. After selection for viability using 7-AAD (Sigma), 3+, 3−, 3+/Ecad− and 3−Ecad+ cells were separated by FACS.

In vivo growth after limiting Dilution;
histology of 3+/Ecad− and 3−/Ecad− tumors.
Cell Proliferation Assays.

OVCAR-5 cells were seeded in T-75 flasks at different densities ($1.6 \times 10^6$, $1.2 \times 10^6$, $0.8 \times 10^6$ cells) with DMEM in 10% FCS, incubated for 24 h, and then treated with either PBS (control) or 60 nM doxorubicin for 24, 48, and 72 h. Cells seeded at $0.8 \times 10^6$ were also treated with cisplatin (0.2, 0.5, 1 µM) for 72 h. Harvested total viable cells were counted by trypan blue staining in a hemocytometer and stained with antihuman CD24-PE, anti-mouse/human CD44-APC/Cy7, anti-human Epcam-APC, and anti-human Ecadherin-FITC. Flow cytometry was performed to analyze for the absolute number of 3+/Ecad− and 3+/Ecad+ cells, which were calculated from the total viable cell numbers by analyzing the percentage of each population adjusted for seeding density (1×, 1.5×, and 2×, respectively).

Cell Cycle Analysis.

OVCAR-5 was grown to 50-60% confluency in DMEM with 10% FCS, untreated or treated with 100 µg/mL (714 nM) MIS or 60 nM doxorubicin for 48 h, harvested, and incubated with 10 µg/mL Hoechst 33342 at 37° C. for 30 min or 40 µg/mL propidium iodide (Sigma) at 25° C. for 30 min. Cells were stained with anti-human CD24-PE, anti-mouse/human CD44-APC/Cy7, anti-human Epcam-APC, and anti-human Ecadherin-FITC for 20 min at 4° C. and fixed in paraformaldehyde (1%), and the cell cycle was analyzed using the SORP LSRII.

Colony Formation Assays.

Colony formation was performed as previously described (4; wei 2010). 3+/Ecad− or 3−/Ecad+ cells separated from the ovarian cancer cell lines were treated with MIS or doxorubicin, cisplatin, or taxol, then plated on 6-well plates containing 2 ml/well complete DMEM medium at 500, 1000, or 2000 cells/well, and incubated for 14 days at 37° C., with a media change at day 7. Cells separated from primary ascites were plated on 12-well plates coated by metrigel or by agarose for colony formation assays at 25,000, 50,000, or 100,000 cells/well. Cells were seeded on 1:2 metrigel or in 0.4% agarose over a 0.8% layer, and incubated for 3-4 weeks at 37° C. At day 14 (cell lines) or day 21 (ascites), plates were washed with 1×PBS, and cells fixed with methanol. Resulting colonies were stained with Giemsa and the stained area captured and analyzed using Image J (Rasband, NIH, USA, http://rsb.info.nih.gov/ij/). Large colonies greater than 4 mm at 10× magnification were also counted and compared.

Immunohistochemistry.

Immunohistochemical analysis was performed with anti-MISRII (Cell Signaling) (Masiakos et al, 1999, Pieretti-Vanmarcke 2006), anti-phospho SMAD 1/5/8 (Cell Signaling), anti-SMAD 1 (Cell Signaling) (Wei, 2006), anti-Lin28 (Abcam), anti-Lin28B (Abcam) (Viswanathan, Daley), or anti-β-actin (Sigma) Immunocomplexes were detected with enhanced chemiluminescence (ECL; PerkinElmer Life Sciences) as described previously.

Immunoblotting.

Lysates were harvested in lysis buffer (Cell Signaling; catalog no. 9803) for 15 min from 80% subconfluent cells or from ascite cells after lysing red cells. Proteins were fractionated on SDS-polyacrylamide gels and transferred to a membrane. The membrane with proteins was blocked in TBST [Tris-buffered saline and Tween 20; 25 mM Tris (pH 7.4), 136 mM NaCl, 5 mM KCl, 0.1% Tween] containing 10% milk for 1 h and incubated with the primary antibodies overnight at 4° C. Immunoblot analysis was performed with anti-LIN28 (1:1,000 dilution) (Abcam; catalog no. ab46020), anti-MISRII (1:1,000 dilution) (Cell Signaling; catalog no. 45185), anti-phospho-SMAD1/5/8 (1:1,000 dilution) (Cell Signaling; catalog no. 9511S), anti-SMAD1 (1:1,000 dilution) (Cell Signaling; catalog no. 9743S), or anti-β-actin (1:1,000 dilution) (Sigma). Blots were washed (three times) with TBST the following day for 30 min and incubated with the appropriate peroxidase-conjugated second antibodies for 1 h, and bound antibodies were detected with enhanced chemiluminescence (PerkinElmer Life Sciences).

RT-PCR Analysis.

Total mRNAs were extracted using RNeasy Plus Mini kit (Qiagen; catalog no. 74134) from separated 3+Ecad−, 3−Ecad+ OVCAR-5 cells, or human ovarian cancer ascites and neat OVCAR-5. Each mRNA was reverse-transcribed to cDNAs using an mRNA Reverse Transcription Kit (Invitrogen). PCR reactions were performed using a Platinum PCR SuperMix kit (Invitrogen). cDNAs were amplified using the following primers: LIN28 #1 F (TCGGACTTCTCCGGGGCCAG) (SEQ ID NO: 10) and R (GCGCAGCCACCTGCAAACTG)(SEQ ID NO: 11); LIN28 #2 F (GCAGTTTGCAGG-TGGCTGCG)(SEQ ID NO: 12) and R (GCTGGGGTGGCAGCTTGCAT)(SEQ ID NO: 13); LIN28B F (AGCCCCTTGGATATTCCAGTC; SEQ ID NO: 14) and R (AATGTGAATTCCACTGGTTCTCCT)(SEQ ID NO: 15); NANOG #1 F (ACCTTGGCTGCCGTCTCTGGC)(SEQ ID NO: 16) and R (AGCAAAGCCTCCCAATCCCAAACA)(SEQ ID NO: 17); NANOG #2 F (TCTCCAACA TCCTGAACCTCAGCT)(SEQ ID NO: 18) and R (GAGGCCTTCTGCGTCACACCA)(SEQ ID NO: 19); SOX2 #1 F (CGG CGGCAATAGCATGGCGA)(SEQ ID NO: 20) and R (CGGCATCGCGGTTTTTGCGT)(SEQ ID NO: 21); SOX2 #2 F (CGGCGGCAATAGCATGGCGA) (SEQ ID NO: 22) and R (TCGGCGCCGGGGAGATACAT) (SEQ ID NO: 23); OCT4 #1 F (TGAGTCAGTGAACAGGGAATGGGT)(SEQ ID NO: 24) and R (ACCTACGTGTGGCCCCAAGGAAT)(SEQ ID NO: 25); OCT4 #2 F (GGCAGCTTGGAAGGCAGATGCA)(SEQ ID NO: 26) and R (TCGGACCACATCCTTCTCGAGC) (SEQ ID NO: 27); cMYC F (CCC GAGCAAGGACGCGACTC)(SEQ ID NO: 28) and R (CGCGGGAGGCTGCTGGTTTT)(SEQ ID NO: 29); KLF4 #1 F (GCAGCCACCTGGCGAGTCTG)(SEQ ID NO: 30) and R (CCGCCAGCGGTTATTCGGGG)(SEQ ID NO: 31); and KLF4 #2 F (TGCCCCGAATAACCGCTGGC)(SEQ ID NO: 32) and R (CGCCAGGTT GAAGGGAGCCG)(SEQ ID NO: (SEQ ID NO: 33). (Each primer has an n=2 except for LIN28B.)

Quantitative PCR.

Total microRNA (miRNAs) were extracted from the different cell lines HOSE-4, HOSE-6, OVCAR-5, OVCAR-3, OVCAR-8, IGROV-1, and SKOV-3 using the miRNeasy Mini kit (QIAGEN) and reverse-transcribed to cDNAs using the TaqMan MicroRNA Reverse Transcription Kit (Applied Biosystems). Levels of Let-7c miRNAs were measured by quantitative PCR using TaqMan Let-7 probes (Applied Biosystems; part no. 4373167) with U47 RNA as internal standard for normalization. Total mRNAs were also extracted from separated and unseparated OVCAR-5, MOVCAR-7, and MOVCAR-8 cell lines using an RNeasy Mini kit (QIAGEN) and reverse-transcribed to cDNAs using the SuperScript III Reverse Transcription Kit (Invitrogen). Levels of Lin28 and cyclin-dependent kinase (CDK) inhibitor mRNAs were measured by quantitative PCR with GAPDH as an internal standard using the following primers:

LIN28 F (CGGGCATCTGTAAGTGGTTC)(SEQ ID NO: 34) and R (CAGACCCTTGGCTGACTTCT)(SEQ ID NO: 35); p15 F (GGGGCAAGTGGAGACGGTGC)(SEQ ID NO: 36) and R (CCTGGGCGCTGCCCATCATC)(SEQ ID NO: 37); p16 F (ATATTTGCGTTCCGCTGGGTGC) (SEQ ID NO: 38) and R (TTGGGATTGGCCGCGAAGT-TCC)(SEQ ID NO: 39); p18 F (TGGATTTGGGAGAACTGCGCTGC)(SEQ ID NO: 40) and R (CAGGAAACCTGCTCTGGCAGCAT)(SEQ ID NO: 41);

p19F (ACCGGGAGCTGGTGCATCCT)(SEQ ID NO: 42) and R (TCTTGGACATTGGGGCTGGCAC)(SEQ ID NO: 43); p21 F (ATATTTGCGTTCCGCTGGGTGC)(SEQ ID NO: 44) and R (TTGGGATTGGCCGCGAAGTTCC)(SEQ ID NO: 45); p27 F (ACCCAACTACCAGCTGTGGGGT) (SEQ ID NO: 46) and R (GCGGAACAGGTCGGACAT-CACC)(SEQ ID NO: 47); CDK2 F (CGCCAGACG-TAAACAGCTCCGAATT)(SEQ ID NO: 48) and R (AGGCAGATGGTTTAAGAGTGCCT)(SEQ ID NO: 49); CDK4 F (CCCTGTGGTACCGAGCACCTG)(SEQ ID NO: 50) and R(AATAGGGCCCTGCGGGTCAC)(SEQ ID NO: 51); CDK6 F (TGGTCTGGCCCGAAGCGTCC)(SEQ ID NO: 52) and R (GCAGGGGATCTTACGCTCGGCTA) (SEQ ID NO: 53); and GAPDH F (GGAGCCAAAAGGGT-CATCATCTC)(SEQ ID NO: 54) and R (AGAAGACT-GTGGATGGCCCCTC)(SEQ ID NO: 55). Relative fold changes of Let-7c miRNAs and Lin28 and CDK inhibitor mRNAs were calculated as $\Delta Ct$ or $\Delta\Delta Ct$ (1) (n=3 for each primer).

Statistical Analysis.

Univariate two-tailed t tests compared two sets of data having parametric characteristics in colony formation assays, cell proliferation assays, cell cycle analysis, and for Lin28 detection by flow cytometry; qPCR experiments were performed in vitro in triplicate. Kaplan-Meier and log-rank (Mantel-Cox) and Geham-Bresluw-Wilcoxan analyses were used to compare differences in time to tumor appearance between 3+/Ecad− and 3+/Ecad+ cells. For qPCR analysis of CDK inhibitors, nonparametric ANOVA was performed by Tukey's test. All data are expressed as means±SD or ±SE and were analyzed using GraphPad Prism (Mac OS X, V.5.0a). The RT-PCR has been repeated 3 times per sample to ensure reproducibility. Tested against OVCAR-5; 3+/Ecad−, 3−/Ecad+, neat, ascites, tumor samples, iPS cells; ES cells

RNA/DNA FISH.

RNA or DNA FISH was carried out as described (J Lee 2008). OVCAR-5 cells or ascites were cytospun onto glass slides and fixed with 4% PFA. StarFISH X chromosomal paints (Cambio) were hybridized according to manufacturer's instructions. DNA probes, a gift from by J Lee, which targeted XIST exon 1 were labeled with fluorescein-12-dUTP using the Prime-It Fluor Labeling kit (Stratagene); XIST RNA probes were also transcribed to target exon 6 by using T7 RNA polymerase (Roche) with Alexa Fluor 488-5-UTP. DAPI nuclear staining was used as reference. Explain how spreads were done.

Immunohistochemistry, and Immunofluorescence.

Tissues or cultured cells [mouse or human???] were fixed in 4% paraformaldehyde and immunohistochemistry and immunofluorescence performed as previously described (J Teireira 2010; Wei 2003) using the following primary and secondary antibodies: anti-Lin28 (1:100; Abcam); anti-CD44 (1:100; Neomarkers); anti-24 (1:100; Neomarkers); anti-Epcam (1:250; Neomarkers); AlexaFluor secondary antibodies (1:500; Invitrogen); and Biotinylated donkey anti-mouse or anti-rabbit antibody Fab (1:1,000; Jackson ImmunoResearch Laboratories). Images were captured with a Nikon TS2000 microscope equipped with a Spot digital camera (Diagnostic Instruments).

TABLE 1

Antibody sources and dilutions

| Antibody | Company | Catalog no./source |
|---|---|---|
| Anti-human CD24-PE | eBioscience | 12-0247-42 |
| Anti-mouse/human CD44-APC/Cy7 | Biolegend | 103028 |
| Anti-human Epcam-APC | Biolegend | 324212 |
| Anti-human Ecadherin-FITC | Biolegend | 324103 |
| Anti-mouse/human Lin28; 1:500 | Primorigen Biosciences | gift |
| Anti-LIN28; 1:1,000 (Western), 1:100 immunofluorescence (IF) | Abcam | ab46020 |
| Anti-MISRII; 1:1,000 | Cell Signaling | 4518S |
| Anti-phospho-SMAD1/5/8; 1:1000 | Cell Signaling | 9511S |
| Anti-SMAD1 | Cell Signaling | 9743S |
| Anti-β-actin; 1:1,000 | Sigma | A1978 |
| Anti-CD44; 1:100 | Neomarkers | ab6124 |
| Anti-CD24; 1:100 | Neomarkers | MS1279 |
| Anti-Epcam; 1:250 | Millipore | MAB4444 |
| Alexa-Fluor secondary; 1:500 | Invitrogen | A21206 |
| Biotinylated donkey anti-rabbit; 1:1,000 | Jackson ImmunoResearch Laboratories | 711067003 |
| Anti-LIN28B; 1:1,000 (Western blot) | Abcam | ab71415 |

Time to Appearance of Xenotransplanted Tumors.

Limiting dilution assays were performed to evaluate time to appearance of xenotransplanted tumors as previously described (Wei 2010). Briefly, 3+/Ecad− and 3−Ecad+ cells separated from OVCAR-5 cell lines by FACS, were serially diluted (103, 102 cells), resuspended in 1:1 PBS/Matrigel (BD Biosciences, San Jose, Calif.) at 4° C. in 200 uL, and injected subcutaneously into 4- to 6-week-old female NOD/SCID mice (The Jackson Laboratory, Bar Harbor, Me.). 3+/Ecad− cells were injected into the right flank and 3−Ecad+ into the left flank in a protocol approved by the MGH Institutional Animal Care and Use Committee (IRB #2009 N000033/1). Mice were monitored weekly and then daily for tumor formation, and time of appearance was recorded. After mice were euthanized by CO2 inhalation, tumors were dissected, weighed, and volume (L×W×W) measured. Tumors were then fixed or frozen for further study. Fixed sections were stained with hemotoxylin and eosin and examined for identification of tumor type and for comparison of 3+/Ecad− and 3−/Ecad+ cells.

Statistical Analysis.

Univariate two-tailed t tests were used to compare 2 sets of data having parametric characteristics (4, 21, Wei 2010). Colony formation assays were performed in vitro in triplicate. P<0.05 represents statistical significance. For limiting dilution assays in vivo, Kaplan-Meier and log-rank (Mantel-Cox) and Geham-Bresluw-Wilcoxan analyses were used to compare differences in time to tumor appearance, between 3+/Ecad− and 3−Ecad+ cells. Analyses were performed using the statistical software GraphPad Prism (Prism 5 for Mac OSX, Version 5.0a, GraphPad Software, Inc, La Jolla, Calif.).

Example 1

Cancer stem cells for a number of different malignancies (1-4) are capable of unlimited self-renewal and, when stimulated, differentiation and proliferation, which contribute to tumorigenicity, recurrence, metastasis, and drug resistance. Tumor initiating cells, as defined by tumorigenicity, recurrence, invasion, metastasis, and drug resistance, are like somatic stem cells, capable of unlimited self-renewal and proliferation and differentiation when stimulated. The identification of flow cytometry-compatible markers for these stem/progenitor cells in human ovarian cancer makes feasible separation, analysis, and testing for insights into these events and for discovery of new therapeutic targets and the introduction of treatment protocols directed at stem cell targets.

A population of ovarian cancer cells marked by CD44, CD24, and Epcam (3+) were previously found to be enriched with cells with stem/progenitor characteristics. Treatment with doxorubicin, cisplatin, and paclitaxel increased the relative numbers of this enriched population compared to 3-cells; this same enriched population, conversely, was significantly inhibited by Mullerian Inhibiting Substance (MIS) and its mimetic, SP600125 (Wei et al, 2010).

Cells positive for three markers (3+)—CD44, CD24, and Epcam (5)—conserved across primary human ovarian cancers, ovarian cancer cell lines, and normal Fallopian tube fimbria showed stem cell characteristics and increased resistance to chemotherapeutic agents, yet sensitivity to Mullerian inhibiting substance (MIS) (5), a.k.a. anti-Mullerian hormone, a fetal testicular protein (6) that causes Mullerian duct regression. MIS was tested because human epithelial ovarian cancers, which recapitulate the embryonic Mullerian ducts (7), express MIS receptor type II (MISRII) in a large majority of cases (8), and human recombinant MIS inhibits their growth in vitro and in vivo (9, 10).

Because the MISRII-expressing surface epithelium of the ovary is normally characterized by expression of epithelial and mesenchymal markers (11, 12), which become predominantly mesenchymal in transgenic animals as tumor initiation occurs (13), the inventors refined the 3+ population in ovarian cancer cell lines by negative selection for Ecadherin (3+Ecad.), down-regulation of which occurs during epithelial-to-mesenchymal transformation in a variety of cancers (14, 15) and is also associated with poor outcome (16).

As disclosed herein, the inventors recently discovered that addition of E-cadherin negative selection (Ecad−) to the 3+ selection endows the 3+ cells with further enrichment for stem cell characteristics, as measured by increased colony formation in vitro and by shorter tumor-free intervals in vivo.

Loss of E-cadherin has been associated with epithelial to mesenchymal transition (Weinberg et al,) and is thought to contribute to cancer progression by increasing proliferation, invasion, and/or metastasis. Whereas the 3+/Ecad+ cells were found in 3-6%, the 3+/Ecad− population was identified in less than 1% of total cells (Wei et al, 2010). Moreover, the 3+/Ecad− cells express Lin28, a marker of pluripotency which is normally expressed at low levels in ovarian surface epithelium but is progressively upregulated in human ovarian cancer cell lines (Viswanathan, Daley, et al, 2009) and in more aggressive ovarian tumors of transgenic mice in which the tumor suppressor, MIS type II receptor (Misr2), is inactivated.

Herein, the inventors discovered that Lin28 is overexpressed in the 3+/Ecad− compared to 3-Ecad+ and OVCAR-5 cells. Furthermore, rather than altering the ratio of cells, doxorubicin significantly increases while MIS decreases significantly the absolute number of colonies formed from this 3+/Ecad− population. Moreover, MIS induces G1 arrest of the 3+/Ecad− cells compared to the chemotherapeutic agent doxorubicin, demonstrating that MIS blocks stem/progenitor cell self-renewal. This 3+/Ecad− population and the molecular mechanisms contributing to stem/progenitor phenotypes provides a novel therapeutic target for ovarian cancer. These results strongly demonstrate that the stem/progenitor population of each patient's ovarian cancer should be separated and tested prior to treatment for drug sensitivity to biologics such as MIS to identify agents that can selectively target this population of cells which we propose might be responsible for ovarian cancer recurrence.

This 3+/Ecad− population of ovarian cancer was demonstrated to be more highly enriched than the 3+/Ecad+ population alone for stem/progenitor characteristics and was also resistant to chemotherapeutic agents but sensitive to inhibition of proliferation by MIS or MIS mimetics.

Herein, the inventors demonstrate that LIN28, a microRNA (miRNA)-binding protein known to regulate expression of cell cycle-related genes and to contribute to cancer stem cell self-renewal and differentiation (17, 18), was the only pluripotency marker among those known to reprogram pluripotency in somatic cells that was increased in these 3+/Ecad− cancer stem cell-enriched population. In addition, LIN28 was demonstrated to also be increasingly expressed in transgenic mouse ovarian cancer models made more aggressive with progressive loss of Misr2 (13). Furthermore, receptor-mediated MIS functional activity correlated with both cell cycle arrest and specific up-regulation of the cyclin-dependent kinase (CDK) inhibitor p15. These findings make it mandatory to test both the stem and the non-stem population in each patient for sensitivity to chemotherapeutic agents and to biologics such as MIS when planning treatment strategies for ovarian cancer, and targeting of LIN28 as an additional or alternative strategy to improve suppression of this elusive 3+/Ecad− stem cell population.

Example 2

Triple Positive (3+) Stem/Progenitor Cell Population with Loss of Ecadherin (3+/Ecad) are More Tumorigenic and Increases Colony Formation In Vitro than Either 3+ Cells Alone or Triple Negative Cells that Retain Expression of Ecad (3−Ecad+)

The inventors have previously identified that a CD44+ CD24+Epcam+(herein referred to the "triple positive" or "3+ population") population is enriched for stem/progenitor populations as determined by colony growth at lower cell numbers (Wei et al, 2010) (5).

Figure 1B:
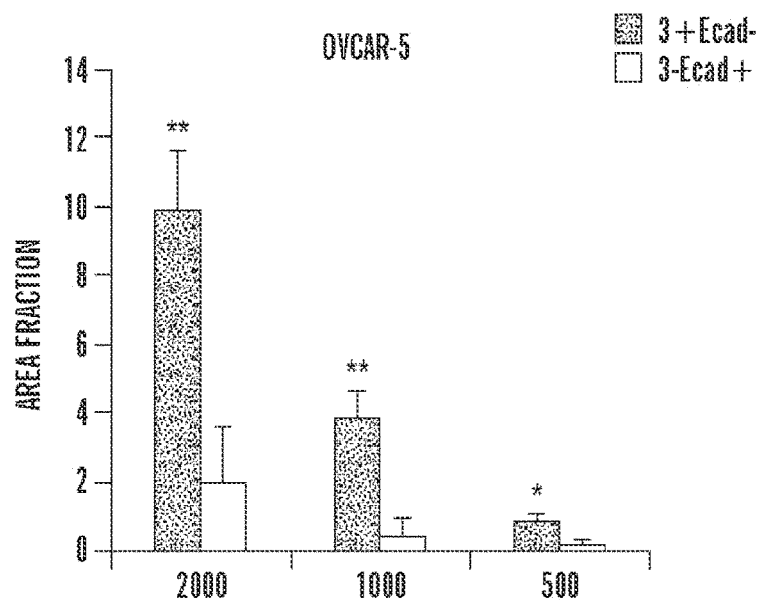
Figure 1C:
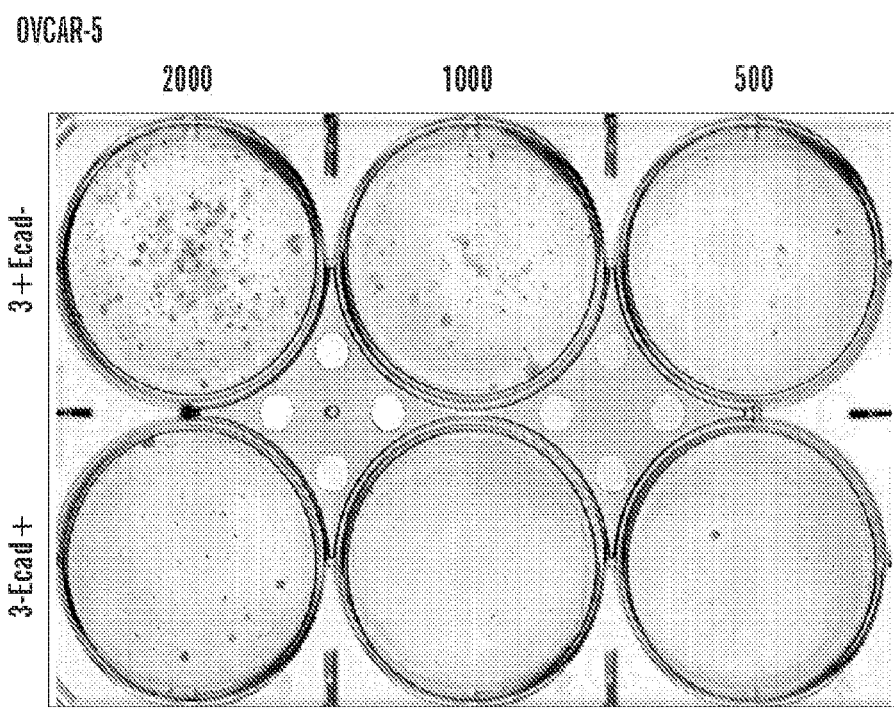

Herein, the inventors have discovered that the 3+ population comprises two population of cells which can be separated from OVCAR-5 cells (human ovarian carcinoma cell line 5) or SKOV-3 cells (Sloan-Kettering ovarian cancer cell line) cells; a subpopulation identified by negative selection for Ecadherin (3+/Ecad−), where such 3+/Ecad− cells formed more colonies after 14 days as compared to 3+/Ecad+ cells (see FIG. 1A, 1B). The 3+/Ecad− cells separated from OVCAR-5 also formed more large colonies as compared to those which were 3+/Ecad+ or triple negative (3−) with positive selection of Ecadherin (3−Ecad+) (data not shown).

Figure 1D:
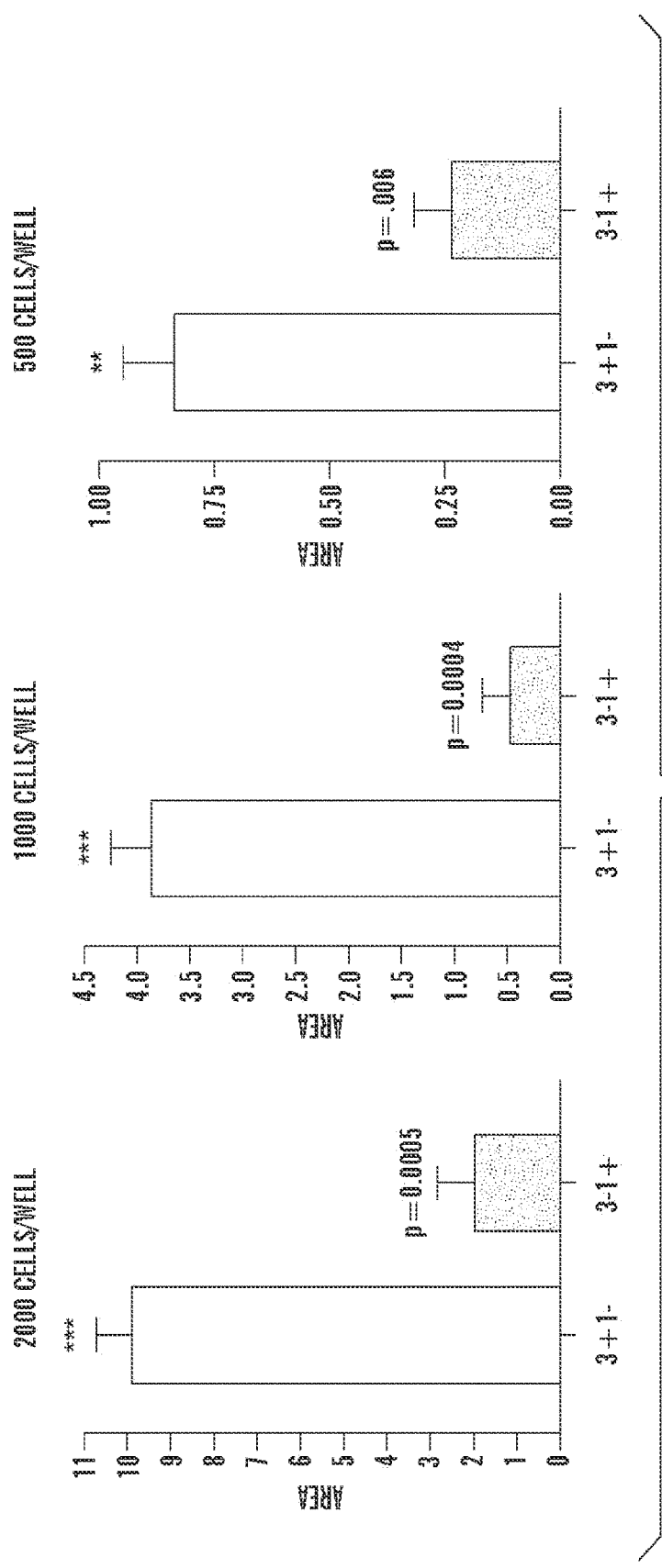
Figure 1E:
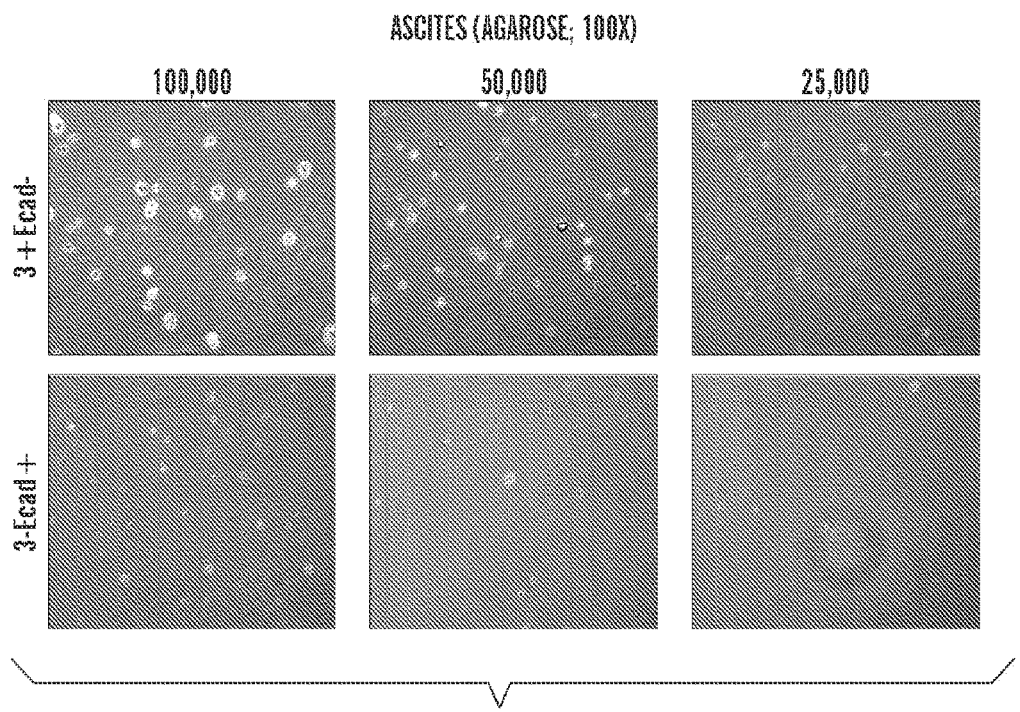
Figure 1F:
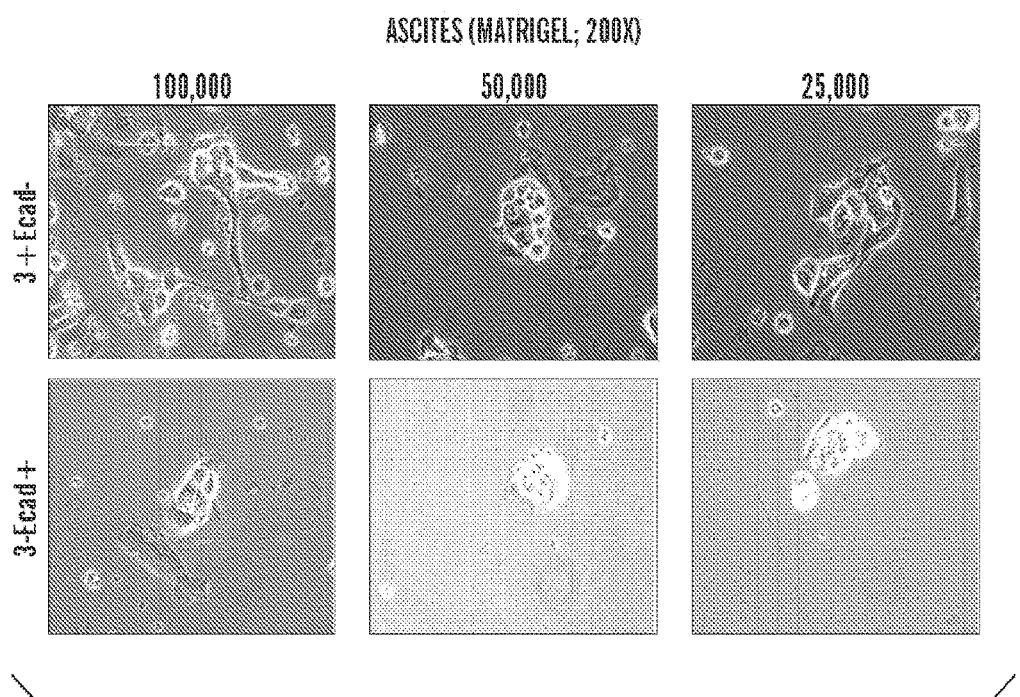

Colony formation assays were also performed to evaluate colony formation capability of the 3+/Ecad− population isolated from human ovarian cancer ascites obtained from subjects with ovarian cancer. The inventors also discovered that the 3+/Ecad− population separated from human ovarian cancer ascites grew more colonies (FIG. 1E) and larger colonies (FIG. 1D) as compared to 3+ or 3+/Ecad+ populations. These findings demonstrate that the 3+/Ecad− population has enhanced colony formation capabilities, and that the absence of Ecadherin contributes to enrichment of the ovarian stem cell population.

Example 3

Figures 1G, 1H:
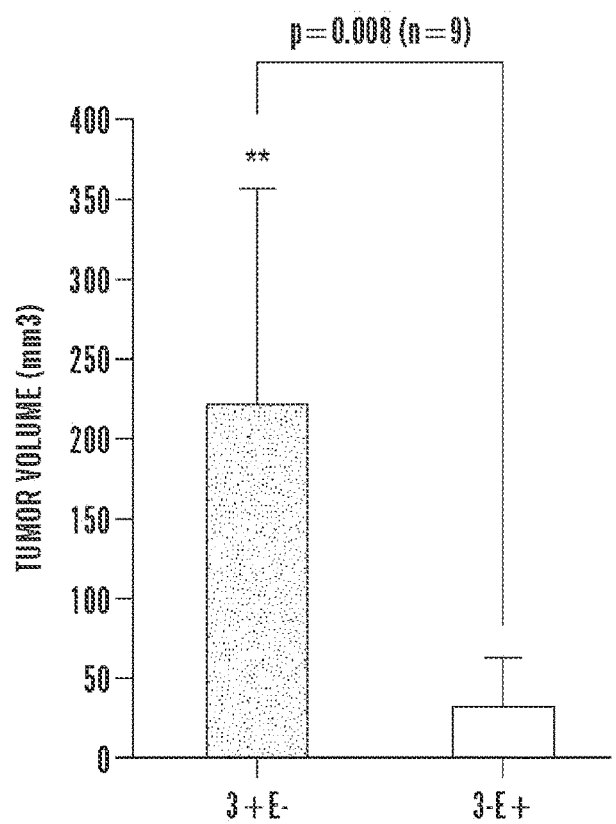
Figures 8A, 8B:
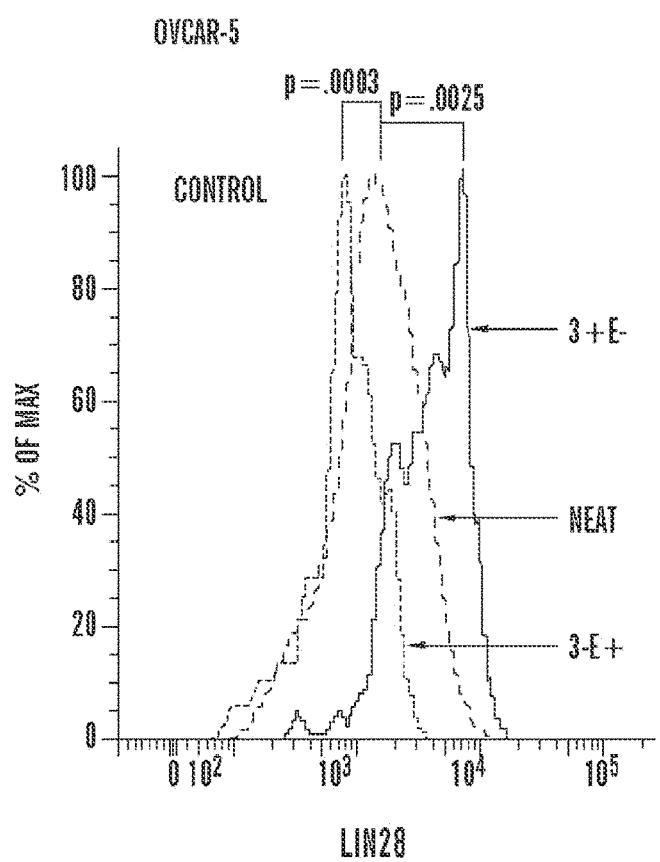
FIGS. 8A and 8B show overexpression of LIN28 in 3+/Ecad− stem cell-enriched population.
Figure 9:
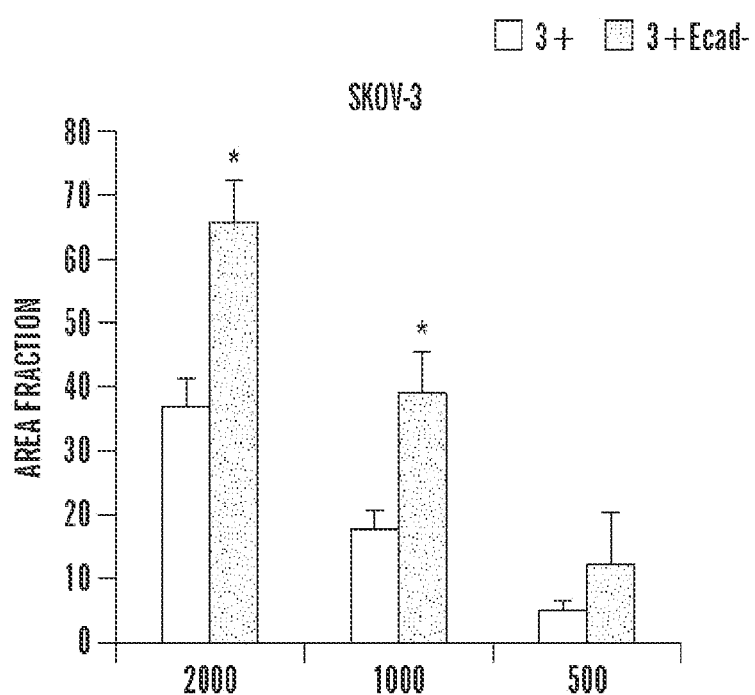
FIG. 9 shows Enrichment of human ovarian cancer stem/progenitor cells enhances colony growth in vitro. CD44/CD24/Epcam triple-positive (3+) and 3+Ecad− cells were isolated from human ovarian cancer cell line SKOV-3 by FACS and plated at the indicated numbers in six-well plates. After incubation for 15 d, colonies were stained, and area was measured and equated to colony formation by ImageJ. CD44/CD24/Epcam triple positive with loss of Ecadherin (3+Ecad−) (black bar) formed more colonies than tripe positive (3+) alone (open bar) (*P<0.05; n=3).
Figure 10:
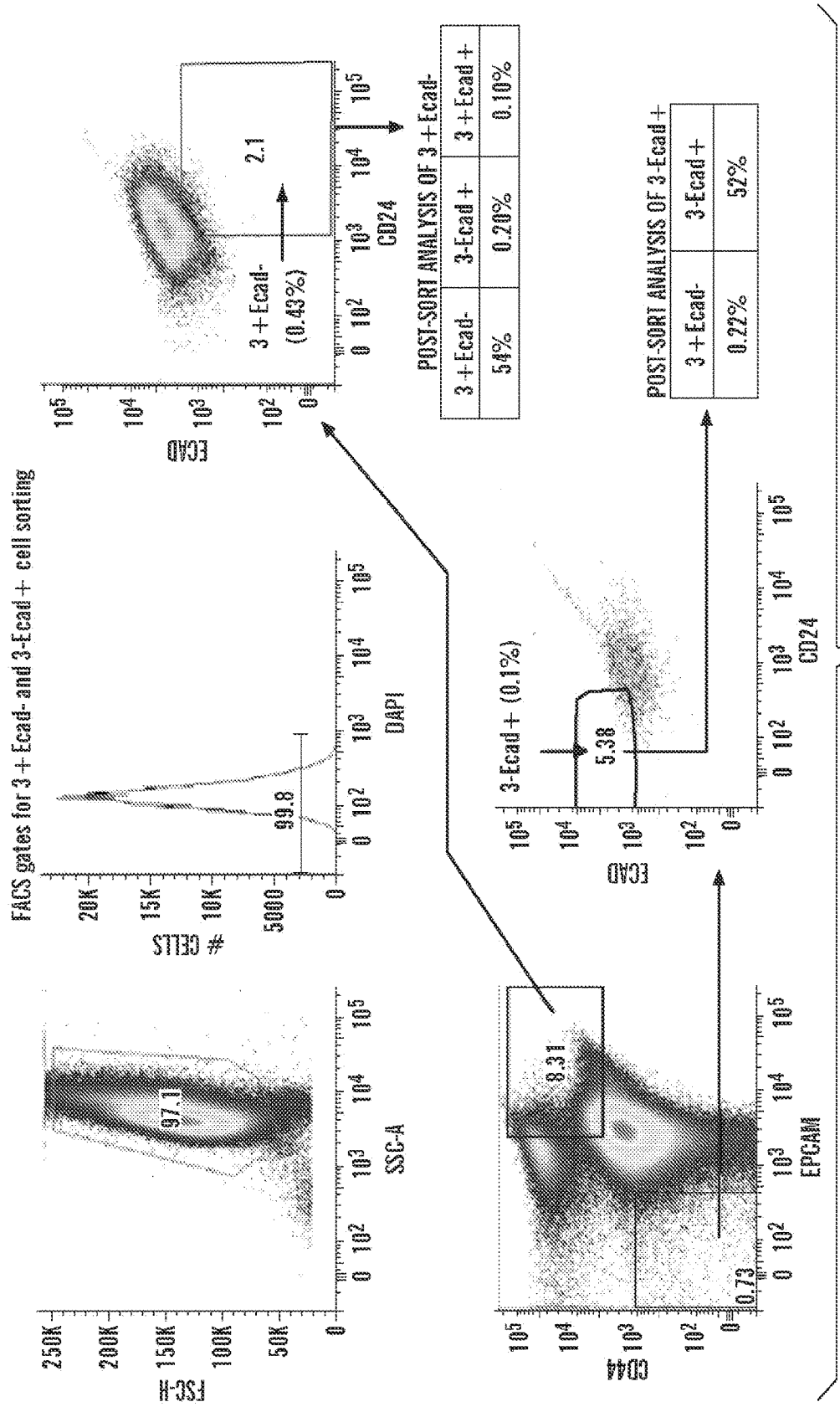
FIG. 10 shows FACS gate for the 3+Ecad− (upper right) and 3−Ecad+(lower right) subsets found in the human ovarian cancer cell line OVCAR-5 is shown. The cells were stained with anti-human CD24-PE, anti-mouse/human CD44-APC/Cy7, anti-human Epcam-APC, and anti-human Ecadherin-FITC (panisotype) for 20 min at 4° C. The data demonstrate the gates used in the isolation of our two subsets and indicate that the two populations were not double sorted but rather simultaneously sorted. The 3+Ecad− population is ~0.43% of the total population whereas the 3−Ecad+ is 0.1% of the total population. The tables below each gate refer to the postsort analysis, which indicates that the 3+Ecad− cells contain 0.20% 3−Ecad+ cells and the 3−Ecad+ cells contain 0.22% 3+Ecad− cells.
Figure 11:
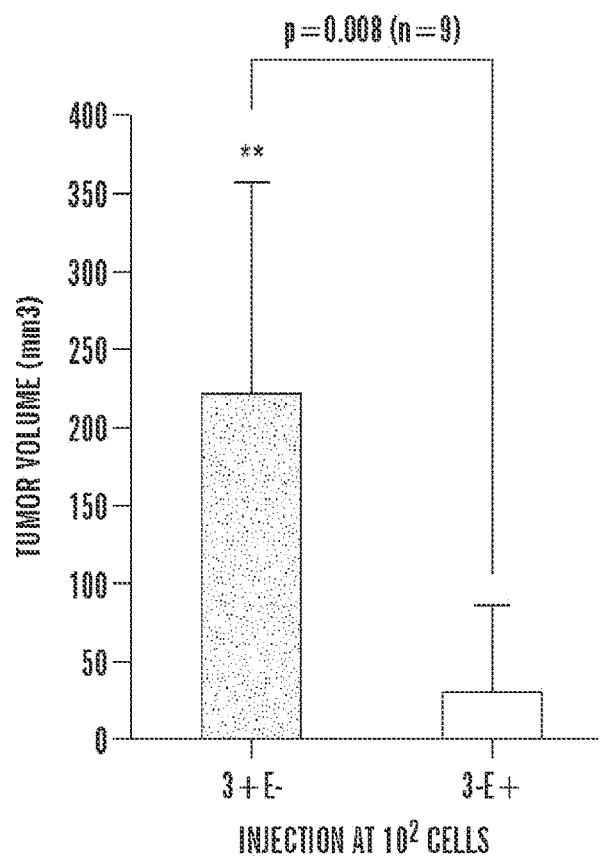
FIG. 11 shows 3+Ecad− and 3−Ecad+ cells separated from OVCAR-5 (102 cells) were resuspended in 1:1 PBS/Matrigel and injected s.c. into 5-wk-old female non-obese-diabetic/SCID mice (nine mice for each group). A t test showed that 3+Ecad− cells ($10^2$) also formed larger tumors at 8 wk than did 3−Ecad+ cells (**P<0.01; n=9 mice for each group). Tick bars indicate SD.
Figure 12:
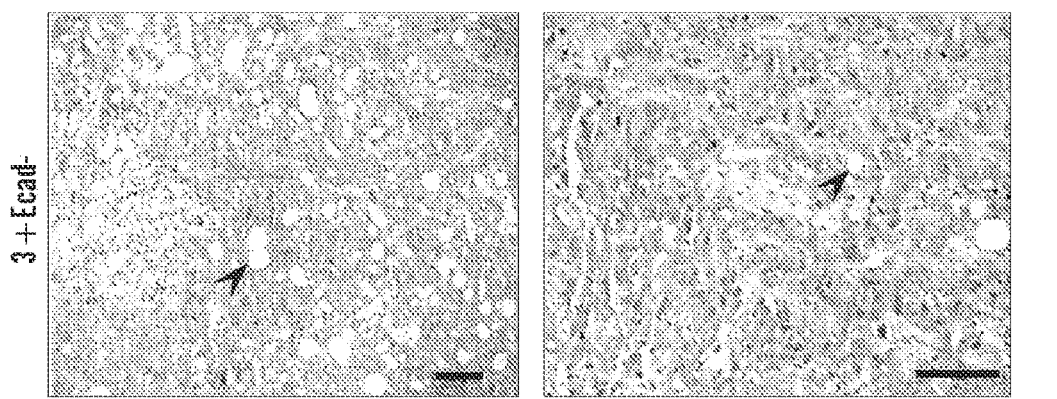
FIG. 12 shows histology of separated OVCAR-5 xenografts. Tumor tissues from 3+Ecad− and 3−Ecad+ OVCAR5 xenografts in non-obese diabetic/SCID fixed with 4% paraformaldehyde, and H&E staining was performed. The histology of the tumors from 3+Ecad− or 3−Ecad+ xenografts showed population grew a highly malignant serous cystadenocarcinoma with signet cells and multicystic components (arrowheads) (Scale bars, 100 µm.)

3+ Cells with Loss of Ecadherin Injected into NOD/SCID Mice Grew Tumors Faster than Did Triple Negative Cells (3) with Expression of Ecadherin Enrichment of 3+ OVCAR-5 cells with negative selection for Ecadherin (3+/Ecad−) also led to earlier tumor appearance (shorter latency) when $10^3$ or $10^2$ cells were injected into the right flank of non-obese diabetic (NOD)/SCID mice compared with 3+ cells, with positive expression of Ecadherin (3/Ecad+) as a control, injected into the left flank (FIG. 1G and FIG. 10). Time to tumor appearance of the 3+/Ecad− cells when subjected to Kaplan-Meier analysis was shorter ($p<0.001$ and $p<0.002$, n=9 animals for each dilution) compared to that of 3−Ecad+ cells (FIG. 1G) injected into the left flank in the same animal. The 3+/Ecad− cells also grew larger tumors after injection of $10^2$ cells as compared to the same number of 3+/Ecad+ cells (FIG. 1H and FIG. 11) when measured at 8 wk. The histology characterizing OVCAR-5 tumors, whether 3+/Ecad− or 3/Ecad+, was that of a highly malignant serous cystadenocarcinoma with signet cells and multicystic components (FIG. 8 and FIG. 12) (19). These findings demonstrate that the 3+/Ecad− population is highly enriched stem/progenitor population in human ovarian cancer cells.

Example 4

MIS Inhibits Whereas Doxorubicin Stimulates Colony and Monolayer Growth of the Stem Cell-Enriched 3+/Ecad− Population (3+/Ecad)

Figure 2A:
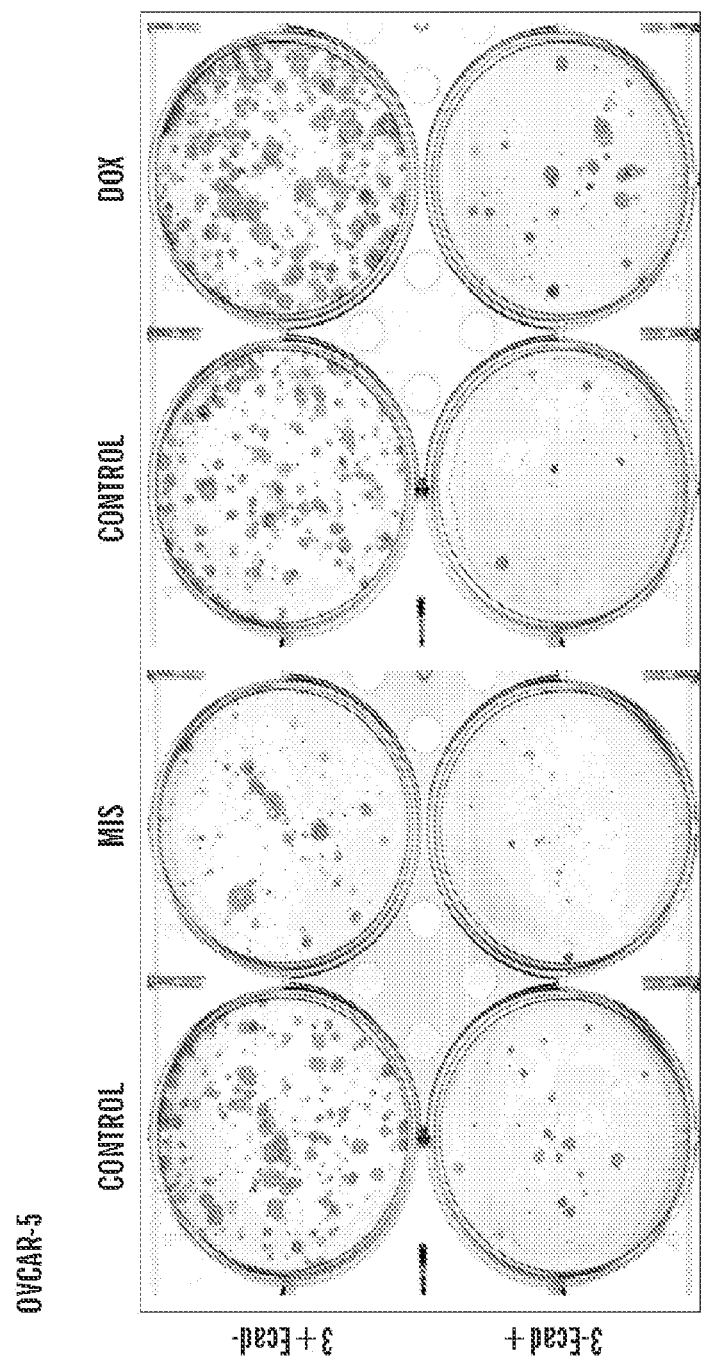
FIGS. 2A-2B show MIS reduced colony formation, proliferation rate and survival of human ovarian cancer stem/progenitor cells by inducing G1 cell cycle arrest and increasing cell cycle inhibitors as compared to Doxorubicin.
Figure 2B:
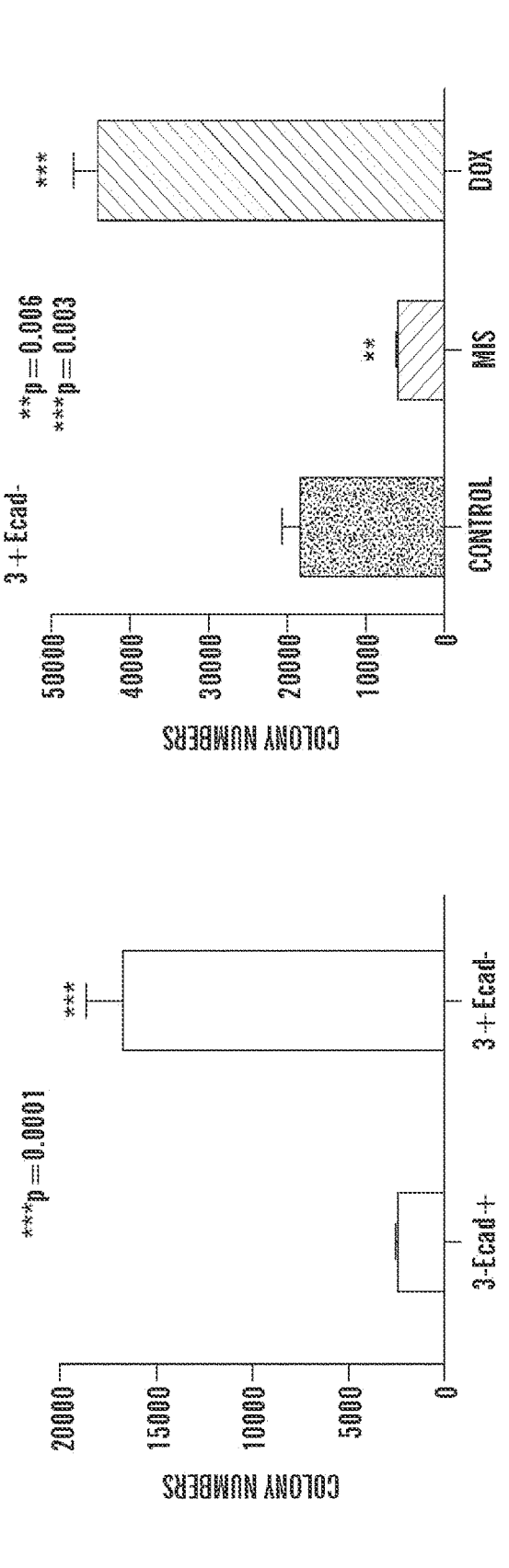
Figure 2C:
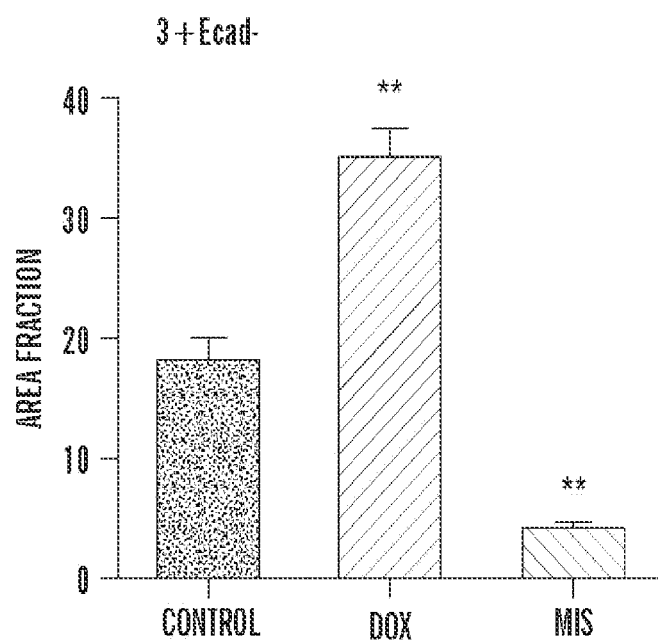
FIG. 2C shows quantification of MIS treatment inhibits colony formation ($p<0.006$) of the 3+/Ecad− cells as compared to doxorubicin ($p<0.003$) which significantly increased colony numbers. MIS treatment inhibited colony formation ($P<0.01$) of the 3+/Ecad− cells compared with doxorubicin (n=3 separate experiments).
Figure 2D:
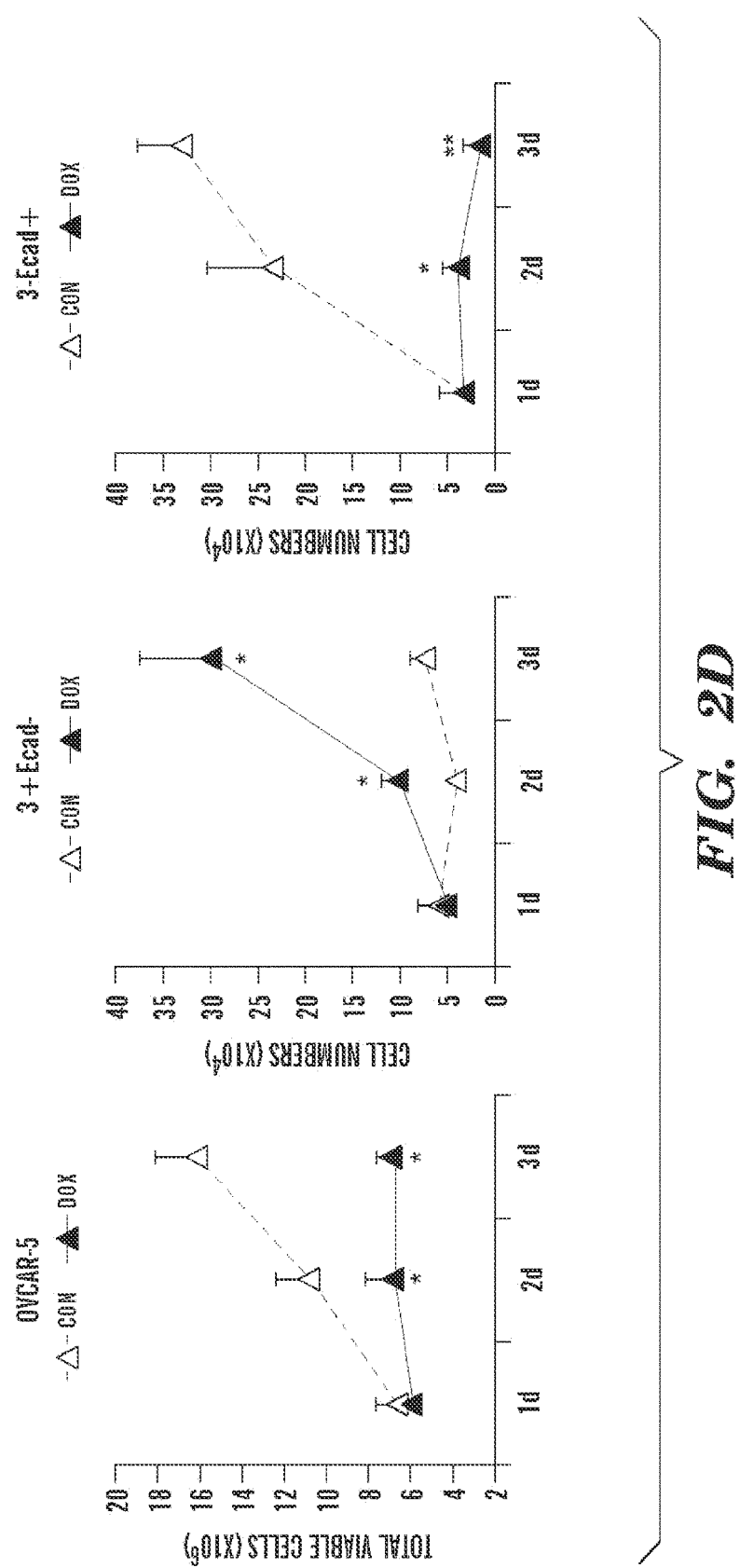
FIG. 2D shows OVCAR-5 cells were plated at 1.6, 1.2, or $0.8 \times 10^6$ cells in T75 flasks (n=3 for each cell number) and treated with doxorubicin (60 nM) for 1, 2, and 3 days. Doxorubicin treatment inhibits proliferation of total viable cells (3D, Left) and 3+/Ecad+ population (3D, Right), but stimulates that of the 3+/Ecad− population (D, Center).
Figure 13:
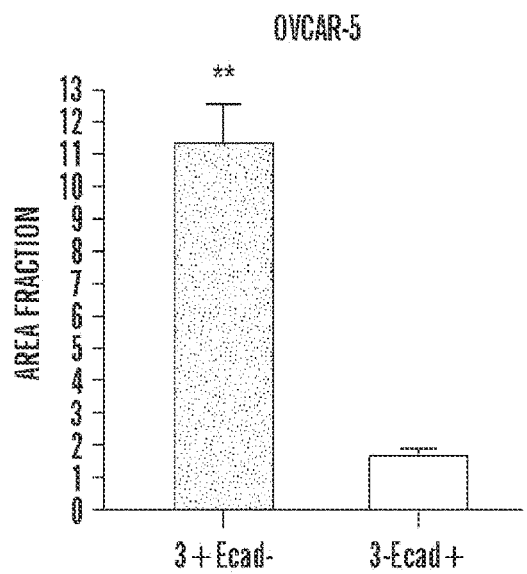
FIG. 13 shows 3+Ecad− stem/progenitor cell-enriched population is more tumorigenic. 3+Ecad− and 3−Ecad+ cells isolated from OVCAR-5 human ovarian cancer cell line by FACS were plated at 2,000 cells/well in six-well plates for 15 d. Colonies were stained, and area was measured and equated to colony formation. 3+Ecad− formed more colonies than did 3−Ecad+ cells (**P<0.001; n=3). Tick bars indicate SD.
Figure 14:
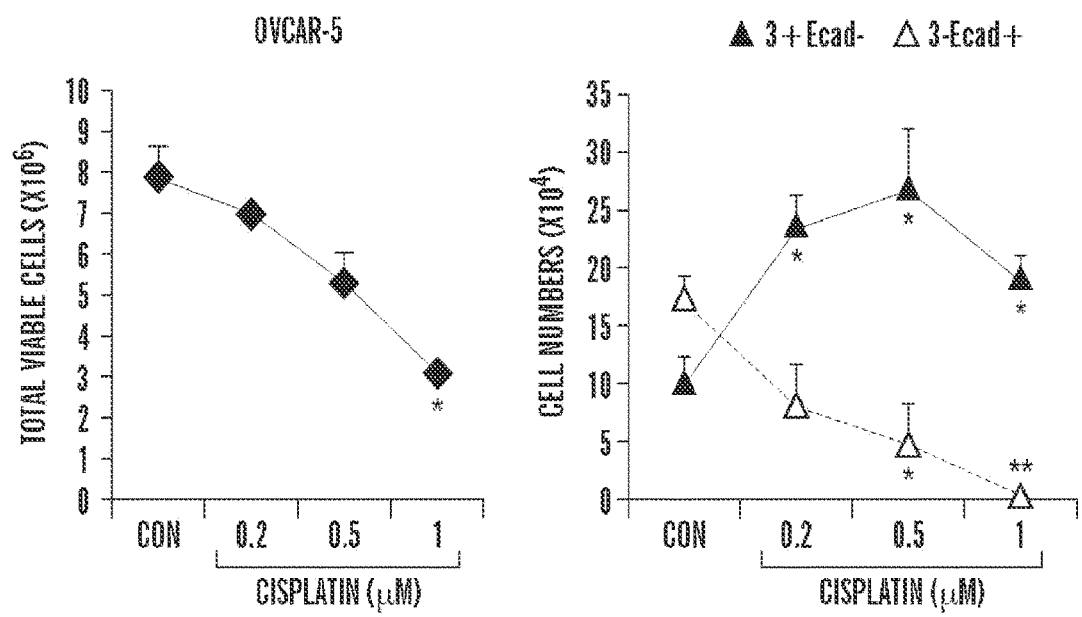
FIG. 14 shows Cisplatin stimulates 3+Ecad− OVCAR-5. OVCAR-5 cells were seeded at 0.8×106 cells and treated with cisplatin (0.2, 0.5, and 1 µM) for 3 d. Cells were harvested, and total viable cells (Left) were counted by trypan blue staining using a hemocytometer. Flow cytometry was performed to analyze for the absolute number of cells in the 3+Ecad− and 3−Ecad+ populations, which was calculated from the total viable cell numbers (n=3 separate experiments). Cisplatin treatment inhibits proliferation of total viable cells (Left) and the 3−Ecad+ population (Right), but stimulates that of the 3+Ecad− population (Right).

Although the inventors previously found by flow cytometry that the ratio of the 3+ cells to total cells increased after treatment with chemotherapeutic agents and decreased after receptor-mediated treatment with MIS (5), herein the inventors have discovered that further separation of 3+/Ecad− and 3+/Ecad+ OVCAR-5 cells showed changes in absolute numbers of colonies. 3+/Ecad− OVCAR-5 cells grew more colonies as compared to 3+/Ecad+ cells (FIG. 2A, control; FIG. 13), which is consistent with the inventors previous finding in normal ovarian surface epithelium (20). However, when separated cells 3+/Ecad− cells were treated with MIS or doxorubicin for 14 d, MIS significantly inhibited colony growth of the 3+/Ecad− cells (FIG. 2A, Upper panels; FIG. 2C); whereas surprisingly, the chemotherapeutic agent doxorubicin did the opposite, 3+/Ecad− cells were stimulated by the chemotherapeutic agent doxorubicin (FIG. 2A, FIG. 2B right, Upper panels; FIG. 2C). Treatment of unseparated OVCAR-5 cells in monolayer with doxorubicin, which resulted in a significant inhibition in total viable cell number (FIG. 2D, Left), also decreased the 3+/Ecad+ population (FIG. 2D, Right), but paradoxically increased the absolute number of the 3+/Ecad− stem cells (FIG. 2D, Center). Similar results were observed after dose-dependent treatment with cisplatin (FIG. 14). These results demonstrate that MIS preferentially inhibits 3+/Ecad− cells, whereas chemotherapeutic agents such as Doxorubicin promote or stimulate colony growth, and thus enrich for the 3+/Ecad− ovarian cancer stem cell population.

Example 5

MIS Inhibition of 3+/Ecad− Stem Cell-Enriched Population Correlates with Cell Cycle G1 Arrest and Induction of p15

Figure 2E:
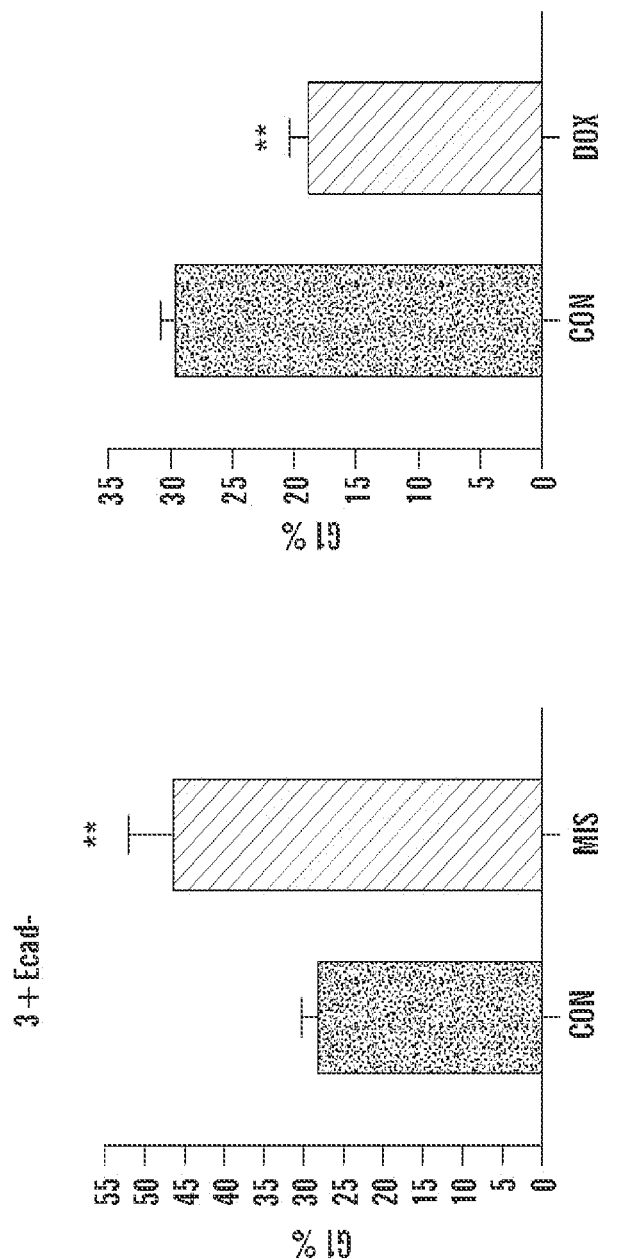
FIG. 2E shows in OVCAR-5 cell cycle analysis, MIS increased the 3+/Ecad− cells in G1 (2E, Left), whereas doxorubicin decreased 3+/Ecad− in G1 (2E, Right) (n=3; $P<0.01$).
Figure 2F:
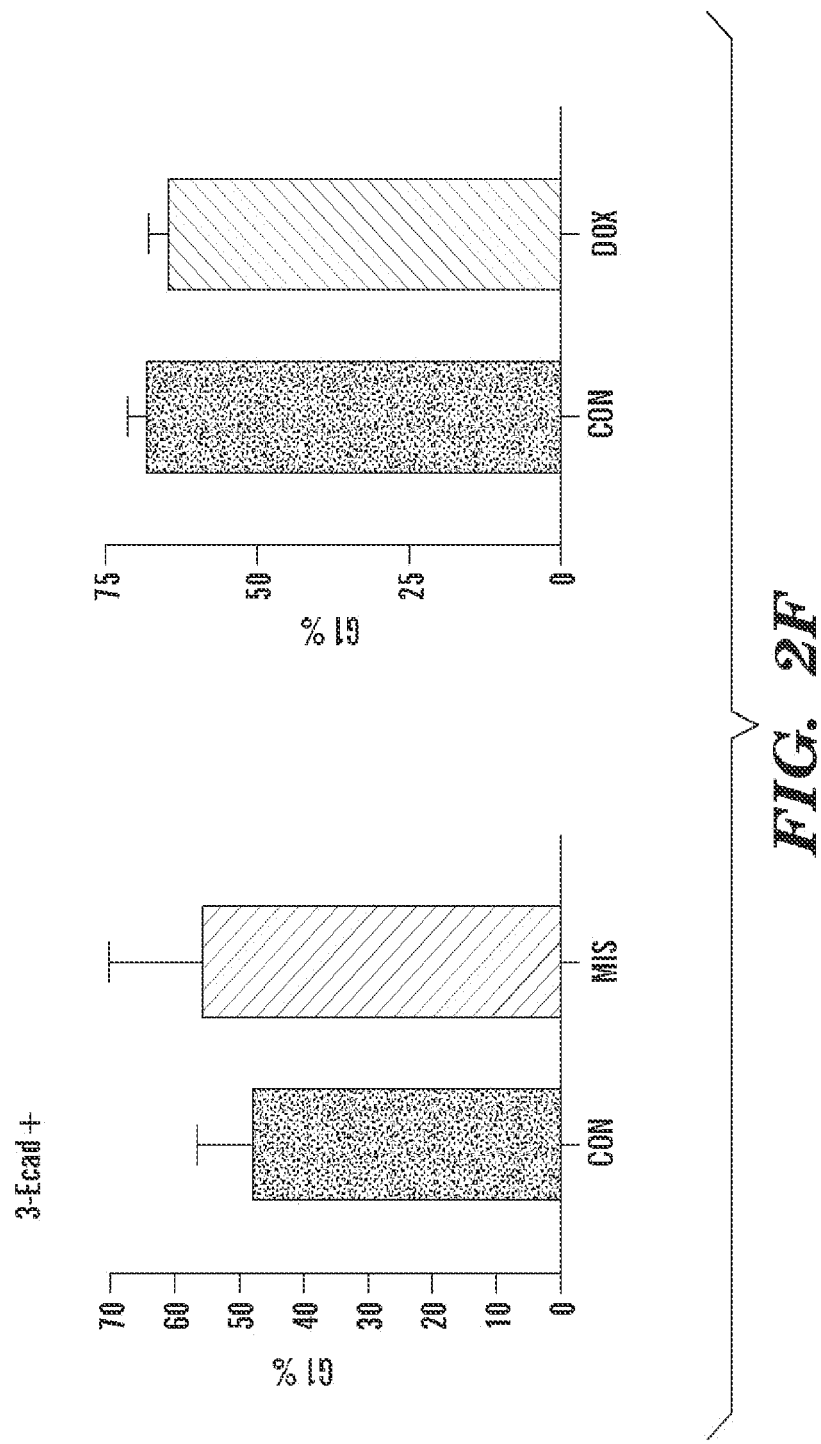
FIG. 2F shows that neither MIS nor doxorubicin affected the G1 distribution of the 3+/Ecad+ population.
Figure 2G:
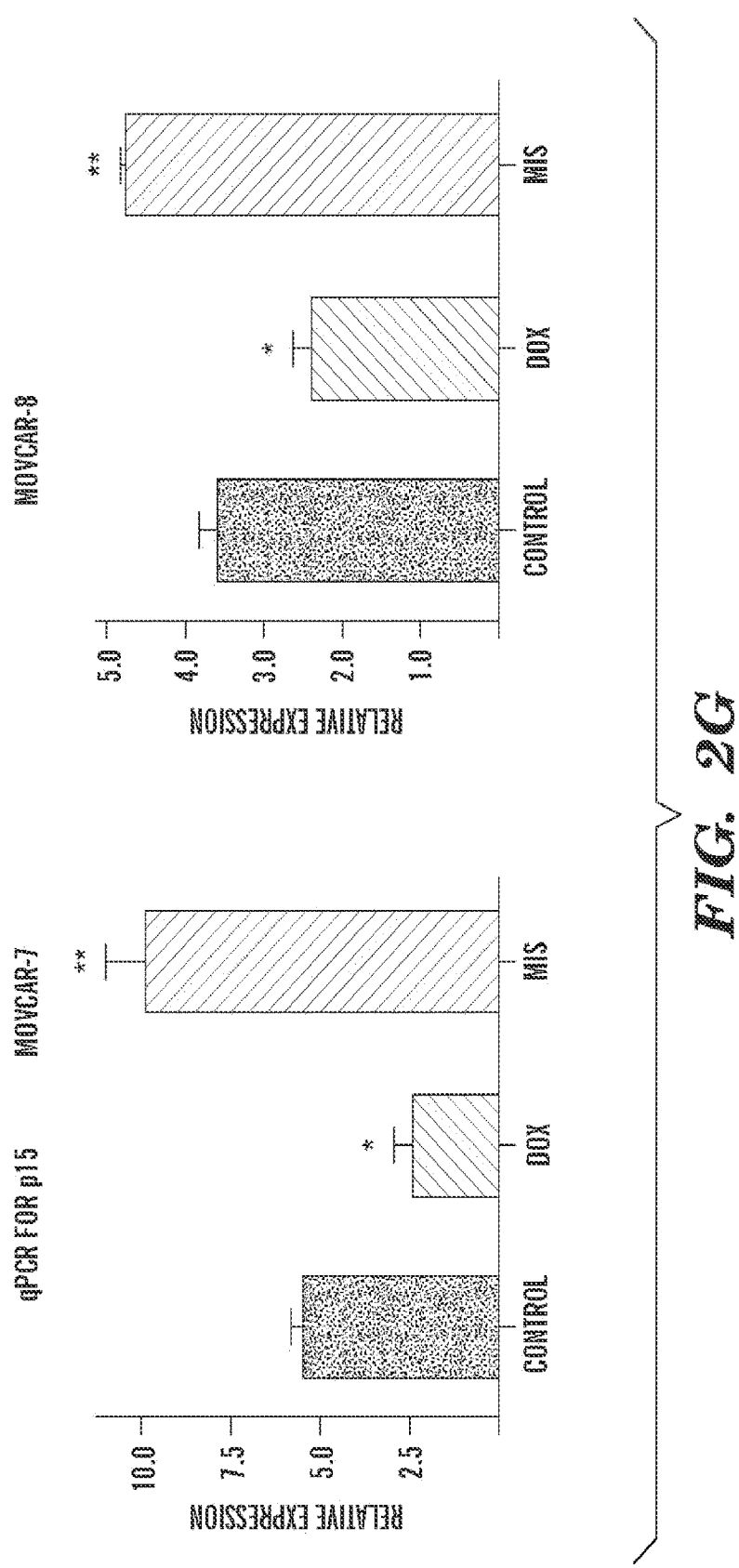
FIG. 2G shows MOVCAR-7 and MOVCAR-8 cell lines were treated with 50 μg/mL of MIS, 60 nM of doxorubicin, or vehicle control for 4 h. MIS increased p15 expression in MOVCAR-7 and -8 (**$P<0.01$); conversely, doxorubicin decreased p15 expression in MOVCAR-7 and -8 (*$P<0.05$).
Figure 6A:
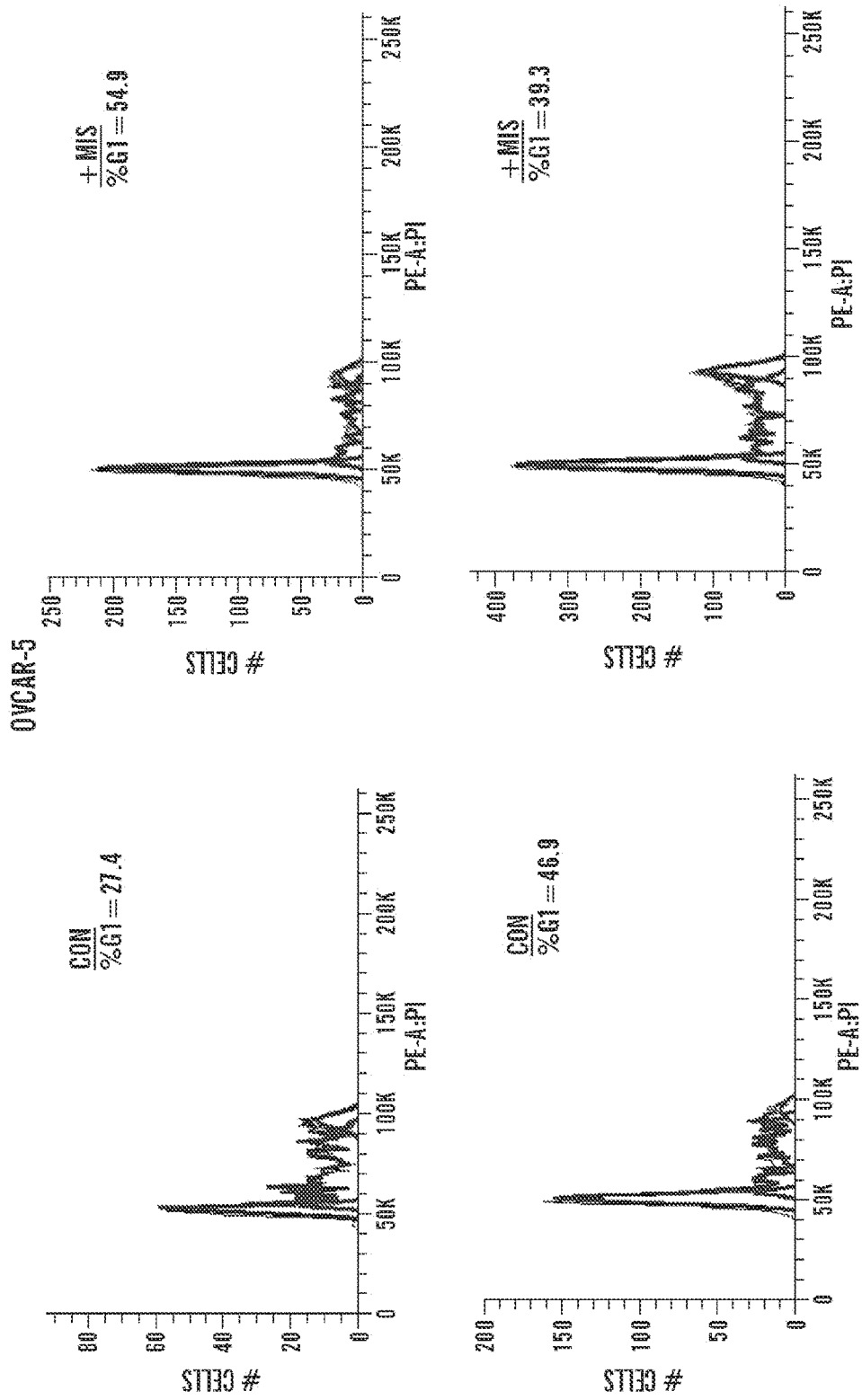
FIGS. 6A-6B show MIS induces G1 cell cycle arrest in ovarian cancer stem/progenitor cells. (A and B).
Figure 6B:
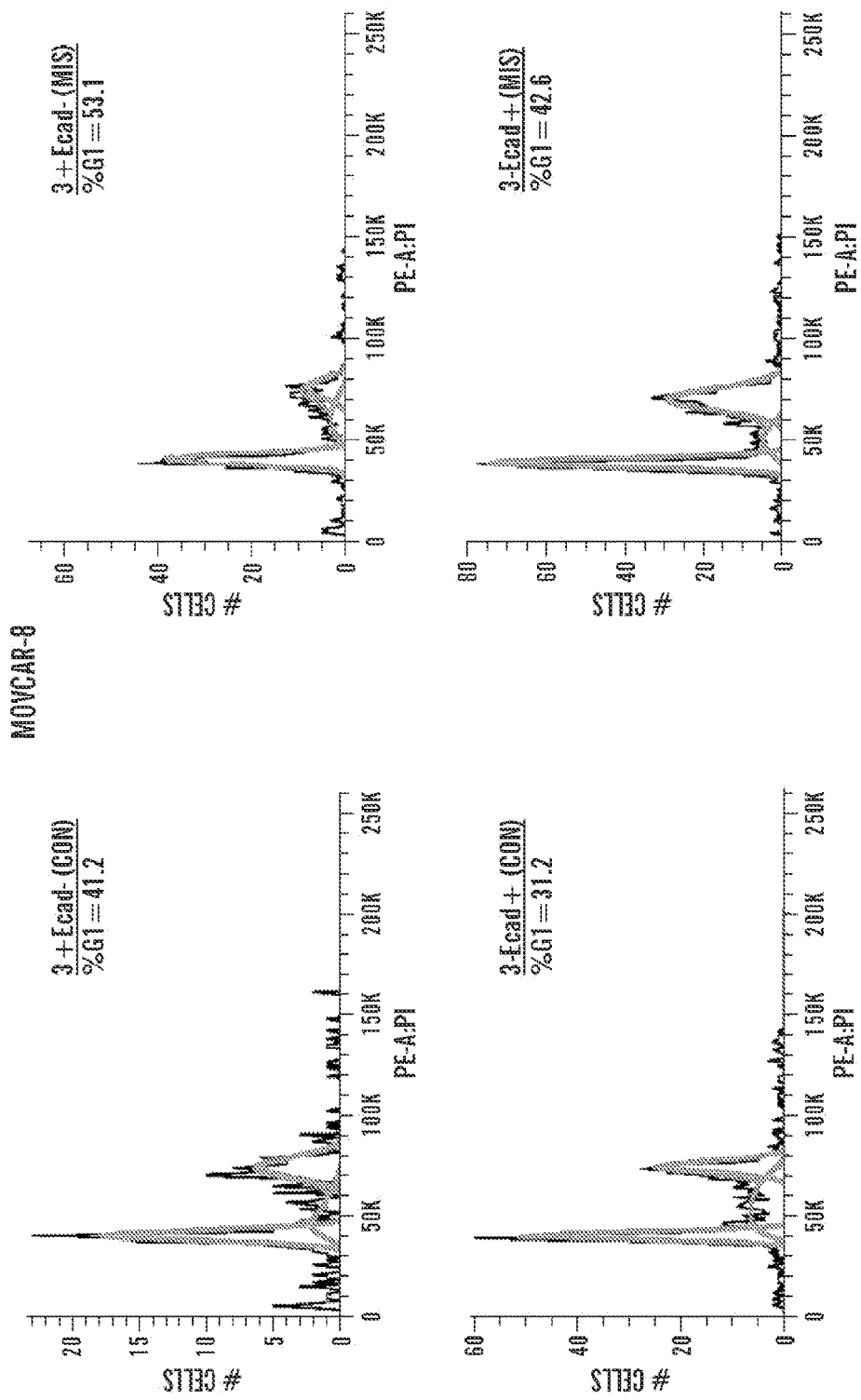
Figure 15:
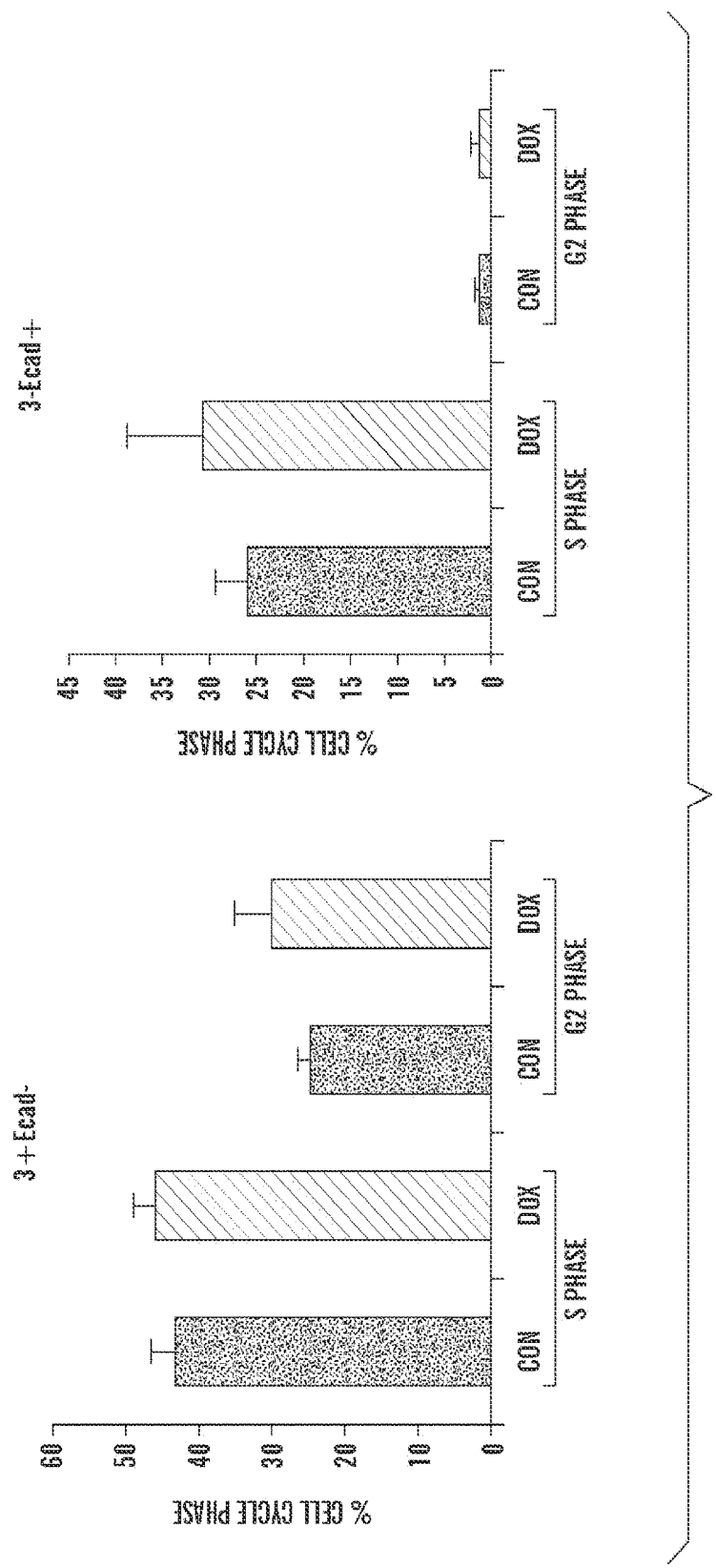
FIG. 15 shows Doxorubicin effects on the cell cycle of 3+Ecad− and 3−Ecad+ OVCAR-5. OVCAR-5 cells were sparsely plated for 24 h in T75 flasks and then treated with doxorubicin (60 nM) for 2 d. Cells were stained with a combination of CD44, CD24, Epcam, and Ecadherin antibodies. Propidium iodide or Hoechst 33342 was used for analysis of cell cycle by flow cytometry. Doxorubicin did not affect the S or G2 distributions of either 3+Ecad− (Left) or 3−Ecad+(Right). (n=3.)
Figure 16:
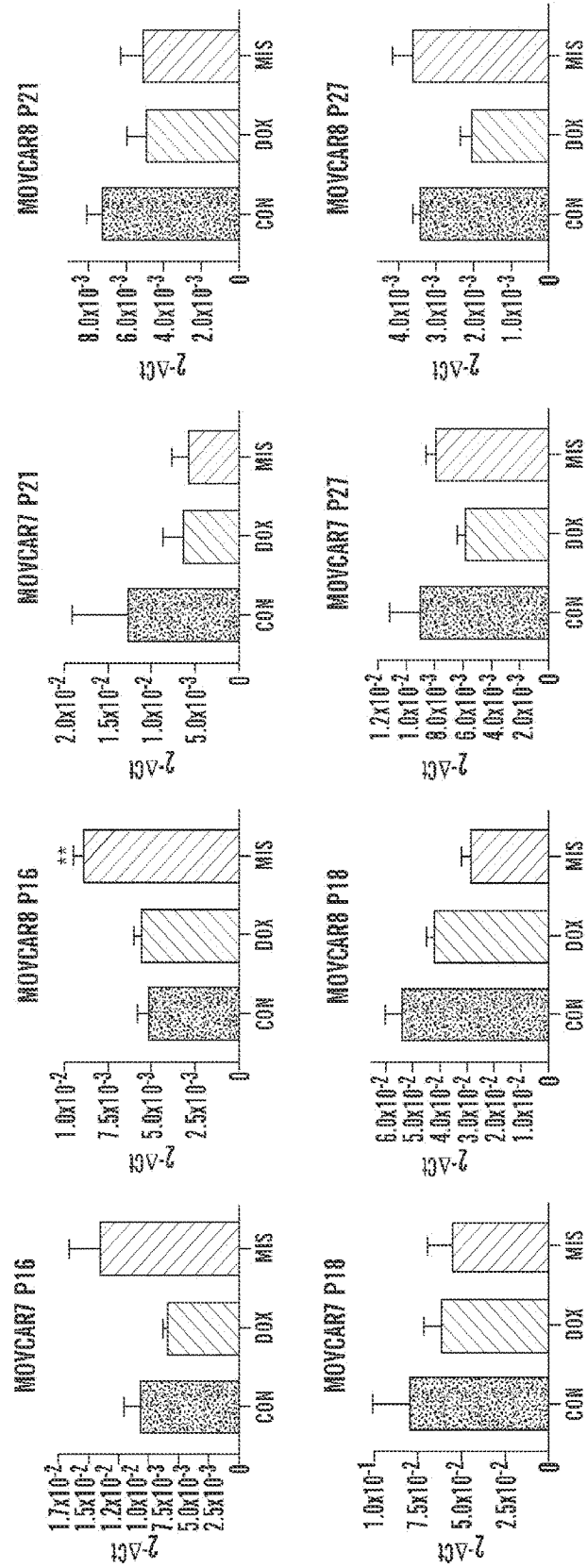
FIG. 16 shows regulation of CDK inhibitor mRNAs by Mullerian inhibiting substance (MIS) and doxorubicin. The MOVCAR-7 and MOVCAR-8 cell lines were treated with 50 µg/mL MIS, 60 nM doxorubicin, or vehicle control for 4 h. Total mRNAs were extracted from these treated MOVCAR-7 or -8 cell lines and analyzed for CDK inhibitors (p16, p18, p19, p21, and p27) and mRNA levels by qPCR relative to GAPDH levels in three experiments performed in triplicate. MIS increased p16 expression in MOVCAR-8 (*P<0.05); however, MIS and doxorubicin did not regulate significantly other CDK inhibitors. Statistical significance was performed by one-way ANOVA, followed by Tukey's posttest.
Figure 16:
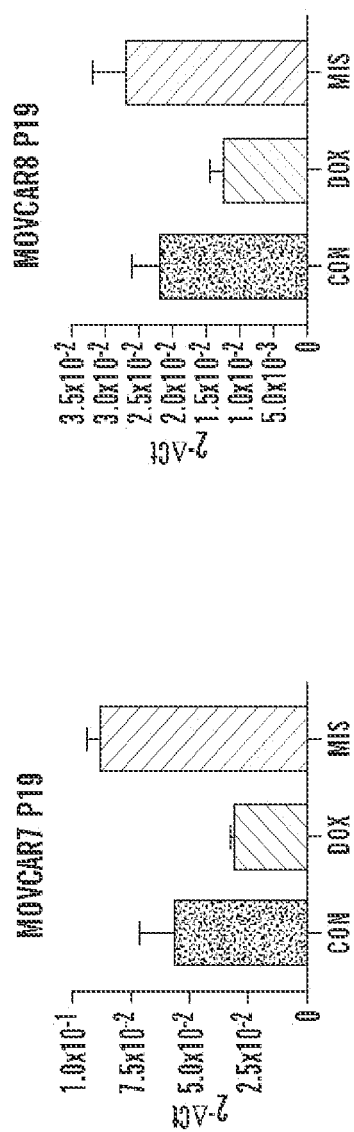

Because cell cycle regulation is important to regulate self-renewal and proliferation (Furukawa, 1998), the inventors next analyzed the comparative cell cycle distribution of 3+/Ecad− and 3+/Ecad+ cells after treatment with MIS or doxorubicin and determined whether MIS-mediated suppression of ovarian cancer stem/progenitor cells growth results from induction of cell cycle arrest. The G1 percentage of the 3+/Ecad− cells was much lower than that of the 3−/Ecad+ cells (FIG. 6A left). MIS treatment significantly increased the percentage of 3+/Ecad− OVCAR-5 cells in G1 (FIG. 2E, Left), but not that of the 3+/Ecad+ OVCAR-5 cells (FIG. 2F, Left and FIG. 6A). By contrast, doxorubicin decreased the percentage of 3+/Ecad− OVCAR-5 cells in G1 (FIG. 2E, Right and FIG. 6A, right), but did not statistically significantly affect the G1 population of 3+/Ecad+ OVCAR-5 cells (FIG. 2F, Right, FIG. 6A, right). Doxorubicin also did not statistically affect the S and G2 distribution of either 3+/Ecad− or 3+/Ecad+ OVCAR-5 cells (FIG. 15). Similar results were demonstrated in 3+/Ecad− MOVCAR-8 cells (FIG. 6B). Moreover, MIS treatment specifically increased the CDK inhibitors p15 (FIG. 2G) and p16 (FIG. 16), tested in the Misr2-directed transgenic mouse ovarian cancer (MOVCAR-7 or -8) cells, because p15 and p16 are mutated in many human ovarian cancer cell lines (21). Conversely, doxorubicin treatment decreased p15 expression in the MOVCAR-7 or -8 cells (FIG. 2G). Meanwhile, MIS and doxorubicin showed a similar trend for p19 and p27, but not for p18 or p21 (FIG. 16). These results demonstrate that MIS inhibits ovarian cancer stem/progenitor cell self-renewal and proliferation through inducing G1 arrest of these cells mediated by p16.

Example 6

Figure 5A:
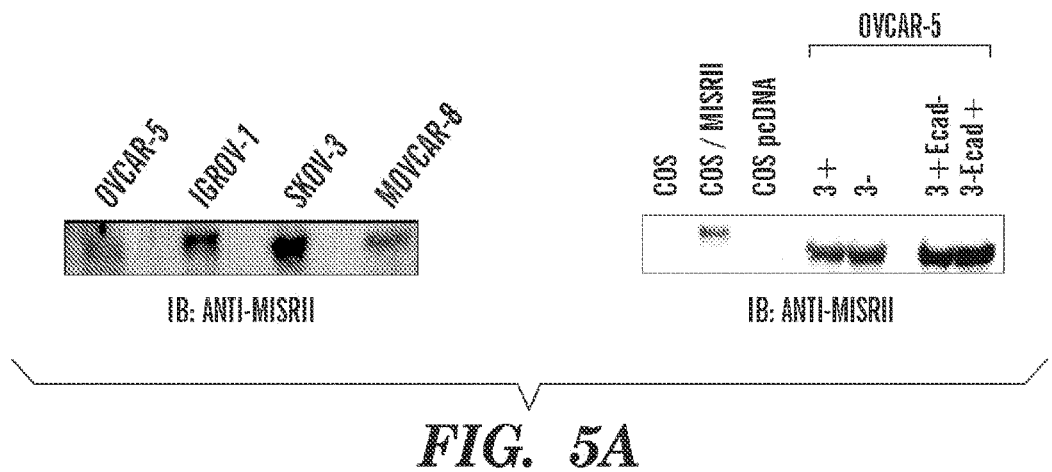
FIGS. 5A-5B show MISRII is expressed in ovarian cancer cell lines and SMAD 1/5/8 is phosphorylated after treatment with purified MIS.
Figure 5B:
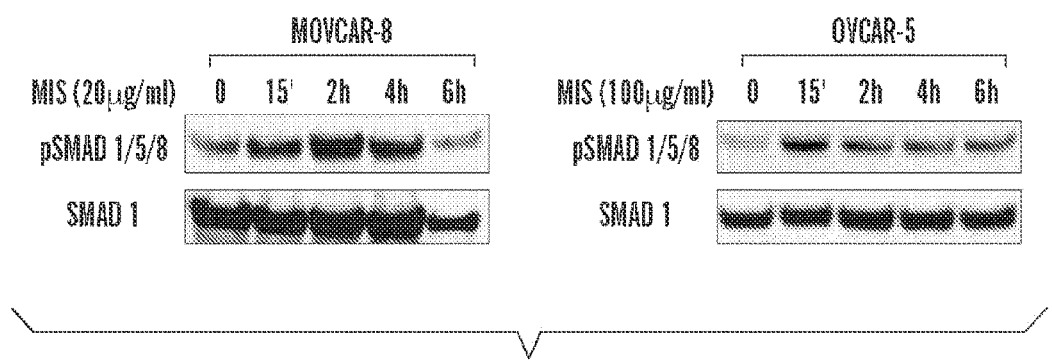

MIS Activates Phosphorylation of SMAD1/5/8 in MIS Receptor-Expressing Cells Signaling of SMAD 1/5/8 occurs in cells which express the MIS Type II receptor (Misr2, also known as MISRII). MISRII was detected by Western analysis in human OVCAR-5, IGROV-1 (Institut Gustave Roussy ovarian cancer cell line), and SKOV-3 cells; in mouse MOVCAR-8 ovarian cancer cell lines (FIG. 5A, Left); and in separated 3+, 3−, 3+/Ecad−, and 3+/Ecad+ OVCAR-5 cells (FIG. 5A, Right). When MOVCAR-8 or OVCAR-5 cells were treated with MIS, SMAD1/5/8 phosphorylation was significantly increased in a dose-dependent manner (FIG. 5B), demonstrating that MIS function is MISRII mediated through MIS-mediated activation of SMAD signalling, which supports previous observations (22).

Example 7

Figure 4A:
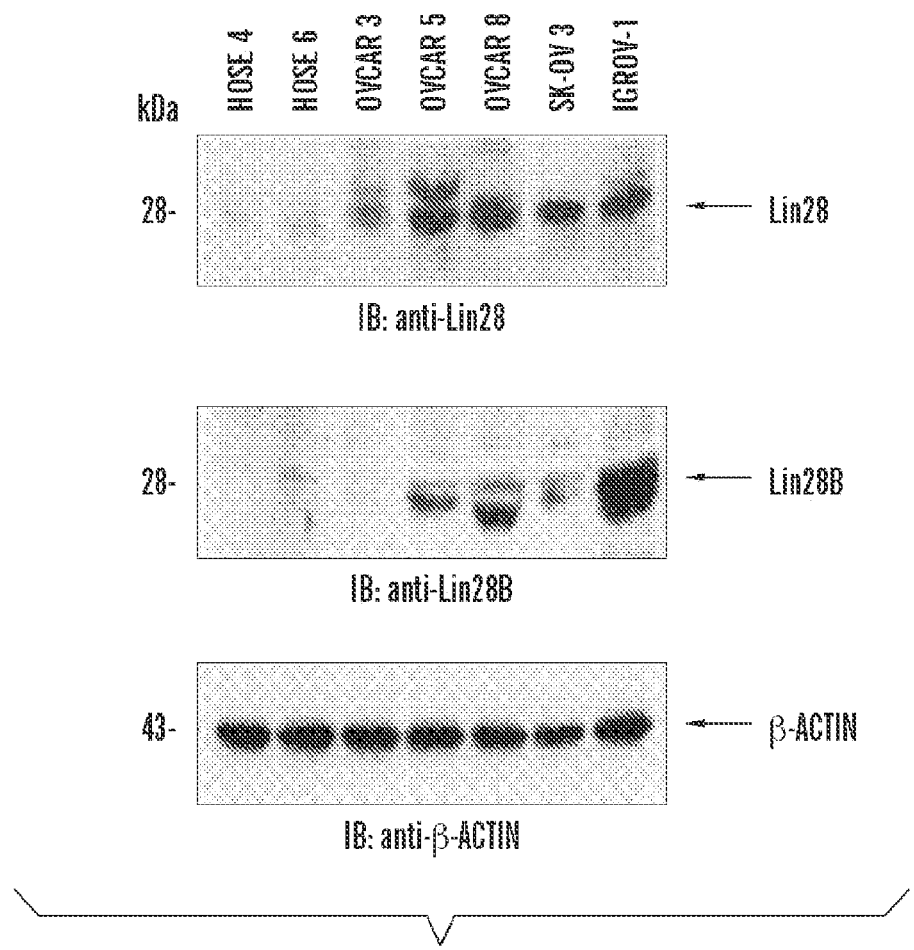
FIGS. 4A-4E show overexpression of Lin28 in 3+/Ecad− stem/progenitor cell enriched population.

Pluripotency Factor LIN28 is Preferentially Expressed in the 3+/Ecad− Stem Cell-Enriched Population After measuring mRNAs by RT-PCR of factors known to induce pluripotency in mouse and human fibroblasts (23, 24, 25), such as OCT3/4, NANOG, SOX2, KLF4, cMYC, and LIN28 (FIG. 8A), the inventors discovered that only LIN28 to be differentially expressed in the 3+/Ecad– stem cell-enriched population in OVCAR-5 xenotransplanted tumors and cell lines. LIN28 protein was strongly expressed in all five human ovarian cancer cell lines tested by Western analysis (FIG. 4A), whereas expression levels were lower in lines derived from normal human ovarian surface epithelium (HOSE-4 and HOSE-6). Let-7 miRNAs, which are suppressed by the miRNA-binding protein LIN28 (17, 18), were reciprocally decreased in most cancer cell lines compared with normal human surface epithelial HOSE cell lines (FIG. 17), with OVCAR-3 as an exception. Quantitative PCR (qPCR) showed higher levels of LIN28 mRNA (FIG. 4D), and flow cytometry showed higher levels of LIN28 protein (FIG. 8B) in 3+/Ecad– OVCAR-5 cells than in 3+/Ecad+ or unseparated OVCAR-5 cells. Moreover, immunofluorescence showed that LIN28 colocalizes with the stem cell markers CD44 (Left), CD24 (Center), and Epcam (Right) (FIG. 4E) in human ovarian cancer OVCAR-5 cells.

Example 8

Misr2 Inactivation Upregulates Lin28 Expression in Transgenic Mouse Ovarian Tumors The pluripotency factor Lin28 is an miRNA binding protein which regulates cancer-related genes. The inventors further examined expression of Lin28 in the ovarian tumors of mice in which Misr2 Cre directed constitutively active (CA) β-catenin was overexpressed (Misr2-$^{Cre-/+}$; ctnnb1$^{ex3/+}$) (26). Misr2 Cre expression drives CA β-catenin expression specifically in the ovary where Misr2 is normally expressed. Lin28 was also examined when these transgenic mice were further crossed with Misr2-Cre$^{-/+}$ to inactivate the second allele of the Misr2 (Misr2-Cre$^{-/-}$; ctnnb1$^{ex3/+}$). The Misr2-Cre–/+; ctnnb1ex3/+ mice grew small indolent tumors in the ovarian epithelium (FIG. 3A, 3D); by contrast the mice also homozygously inactivated for the Misr2 (Misr2-Cre–/–; ctnnb1ex3/+) grew much larger ovarian tumors (FIG. 3B, 3E), indicating that MIS acting through Misr2 is a potent tumor suppressor. Endogenous Lin28, normally expressed at low levels on the surface epithelium of normal ovary of the Misr2-Cre (FIG. 3F and FIG. 4F), was more differentially expressed and progressively upregulated in the malignant epithelium and in small indolent tumors of the Misr2-Cre$^{-/+}$; ctnnb1$^{ex3/+}$ mice (FIG. 3G and FIG. 4G) and more highly expressed in the ovarian tumors of the Misr2-Cre$^{-/-}$; ctnnb1$^{ex3/+}$ mice (FIG. 3H and FIG. 4H), demonstrating that Misr2 expression is negatively correlated with Lin28 expression.

MIS Suppresses Lin28 Expression in Human Ovarian Cancer Cells.

Figure 4B:
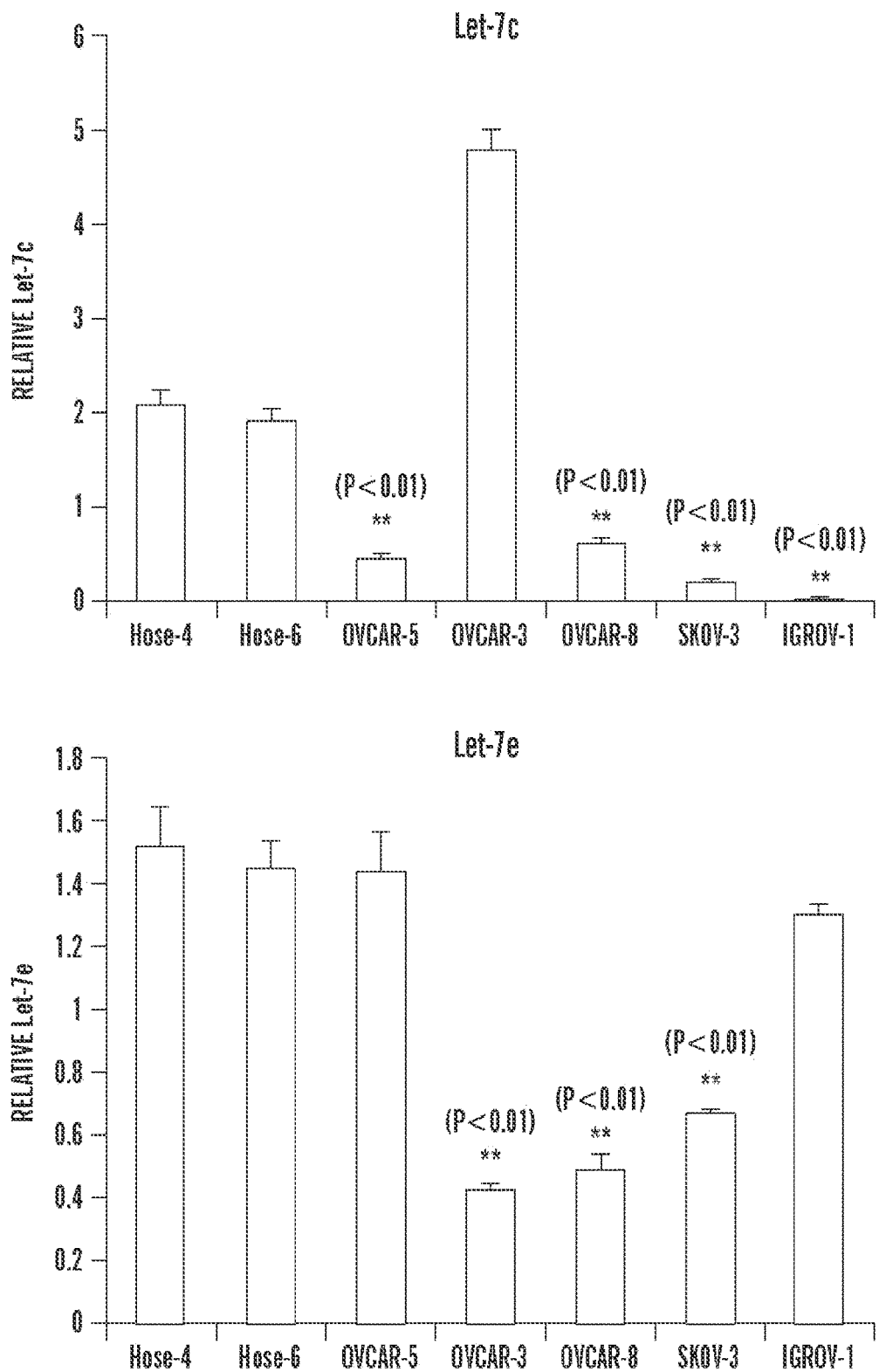
Figure 4C:
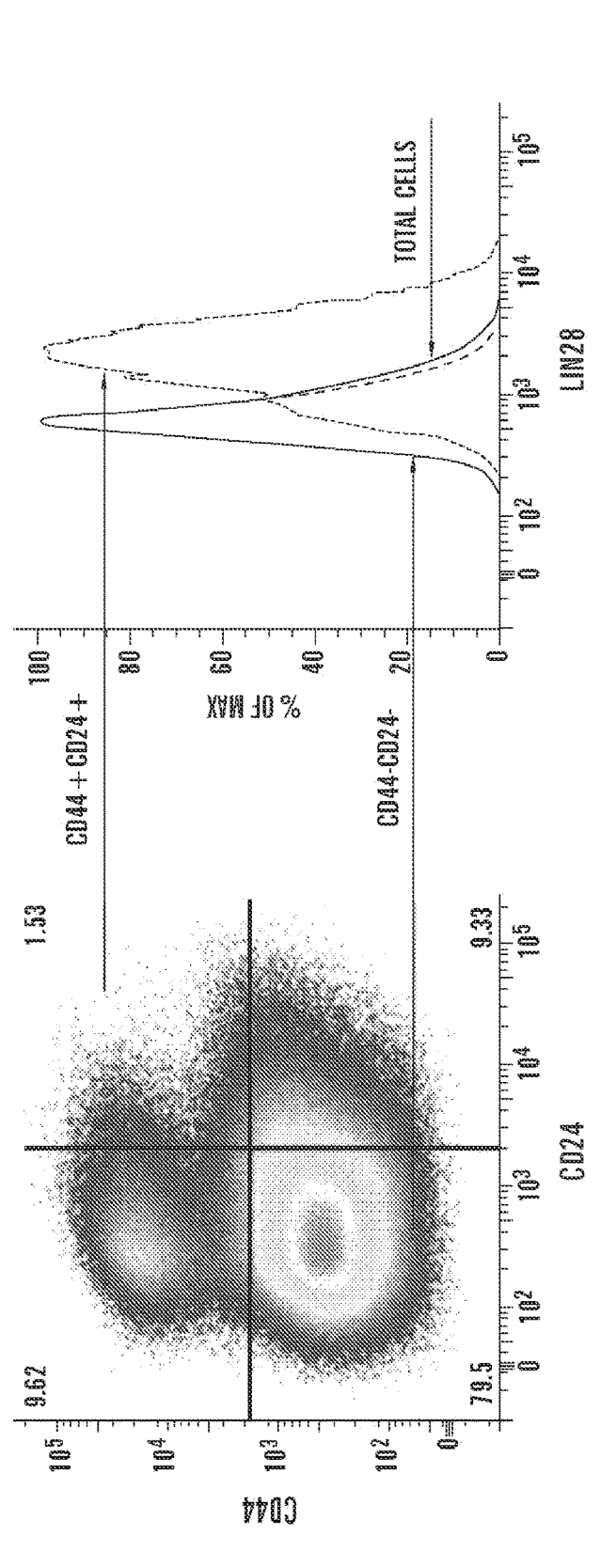
Figure 4D:
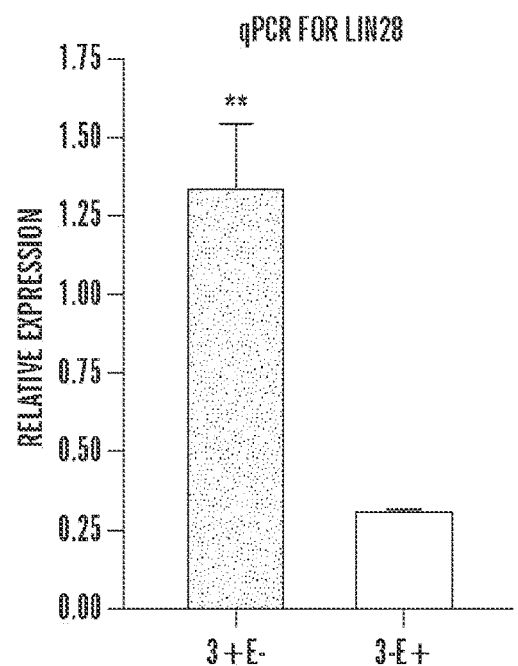
Figure 4E:
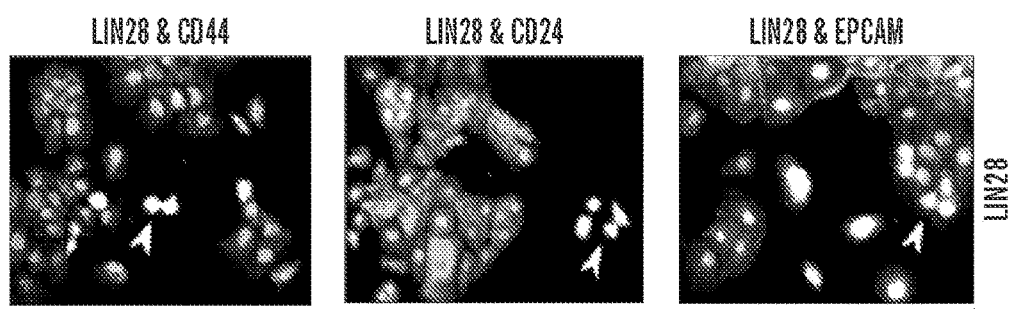

Lin28 and Lin28b were expressed in all five human ovarian cancer cell lines tested by western analysis (FIG. 4A), whereas expression levels were lower in human ovarian surface epithelial cell lines HOSE 4 and HOSE6, demonstrating differential expression in malignant versus nonmalignant cells. Let-7c and -7e miRNAs, which are suppressed by miRNA binding protein Lin28, were reciprocally decreased in most cancer cell lines compared to normal human surface epithelial HOSE cell lines (FIG. 4B). Furthermore, the inventors assessed the association of LIN28 with the stem cell markers. Flow cytometry demonstrated that LIN28 expression in CD44/CD24 double positive OVCAR-5 cells is higher than that in double negative cells or in unselected or neat OVCAR-5 cells (FIG. 4C). Moreover, immunofluorescence demonstrated that Lin28 colocalizes with the stem cell markers CD44 (upper) and Epcam (lower) in human ovarian cancer OVCAR-5 cells (FIG. 4D). Similar results were discovered in 3+/Ecad– stem/progenitor cell enriched population separated from OVCAR-5 or human ovarian cancer ascites (FIG. 4E). The inventors have thus demonstrated that Lin28 is highly expressed in 3+/Ecad– stem/progenitor cell enriched cells. However, no direct effect of exogenously administered MIS could be observed on either separated or unseparated populations of OVCAR-5 cells or on primary ascites, suggesting that the effect of MIS on Lin28 may be indirect (data not shown).

Example 9

The inventors have discovered that, after surgical debulking and paclitaxel and platinum therapies (27, 28), additional attack of the 3+/Ecad– stem cell population should improve the outcomes for this disease. Using a panel of flow cytometry-compatible markers (3+), the inventors have previously reported separating phenotypes by those that are conserved across primary human ovarian cancer ascites, human ovarian cancer cell lines, and normal fimbria and which manifest stem-like characteristics such as enhanced migration and the ability to form colonies in vitro and to form tumors in vivo in NOD/SCID mice after limiting dilution (Wei et al. 2010) (5). Although the markers reported herein enrich for a CD44+/CD24+/EpCam+/Ecad– ovarian cancer cell population ovarian cancers, others such as CD133 (29) and ALDH1 (30) are also encompassed for use in the present invention and can produce similar enrichments. Whatever the selection panel, the practical goal is to use the markers to direct differential therapy for each patient. Importantly, the inventors demonstrate herein that when ovarian cancer cell lines separated by the surface markers CD44+, CD24+, and Epcam+, (3+), and further enriched by negative selection for Ecadherin (3+/Ecad–), when the cells were treated with MIS, there was a significant reduction in absolute colony number and cell number; when treated with doxorubicin, these numbers paradoxically increased, indicating that there is a naive cell population with progenitor characteristics that both escapes detection and is stimulated by currently used clinical chemotherapeutics (31).

Accordingly, the inventors demonstrate herein that the 3+ cells are further enriched for progenitor/stem cell characteristics by negative selection for Ecadherin (3+/Ecad–) This additional negative selection further reduced the percentage of cells from 3-6% to less than 1% in OVCAR5 ovarian cancer cell lines which detected a phenotype which grew tumors faster and larger in vitro and in vivo than did their 3–Ecad+ counterparts. Loss of Ecadherin has been associated with epithelial to mesenchymal transformation during the explosive proliferation which characterizes gastrulation (Anderson, Kathryn, Keystone Symposium) and is previously reported to be a major component of cancer progression characterized by increasing proliferation, invasion, and/or metastasis (Kalluri and Weinberg et al, 2009).

Furthermore, when these more highly separated 3+/Ecad– cells from OVCAR5 were treated with MIS, there was a significant reduction in absolute colony numbers; when treated with Doxorubicin, the colony numbers paradoxically increased significantly.

The pluripotency factor LIN28, which down-regulates the cell cycle regulator miRNA Let-7 (17, 32, 33) to cause G1 arrest and to activate cell cycle inhibitors (p15, p16) (18), is overexpressed in human ovarian cancer cell lines compared with nonmalignant HOSE-4 and HOSE-6, indicating that LIN28 correlates with malignancy. The 3+/Ecad– ovarian cancer cells showed increased protein and mRNA expression of LIN28, both in vitro and in vivo, and reciprocally decreased Let-7 (32, 33). Furthermore, LIN28 coexpressed with CD44, CD24, and Epcam in OVCAR-5 cells (FIG. 4E).

The inventors have made an informative series of transgenic mice in which constitutively active (CA) for β-catenin directed to tissues expressing the MIS receptor Type II (Misr2) (Misr2-Cre$^{-/+}$; β-catenin$^{ex3/+}$) produced thickened coelomic epithelium and indolent small surface tumors in the ovary; additional inactivation of the second allele of the Misr2 (Misr2-Cre$^{-/-}$; β-catenin$^{ex3/+}$) to this transgenic mouse strain led within 2 months to large undifferentiated ovarian carcinomas which expressed the pluripotency factor Lin28. Since LIN28 is normally restricted to the ovarian surface epithelium where Misr2 is coexpressed, it demonstrates that MIS RII (Misr2) negatively correlates with Lin28 expression. These series of transgenic mice with progressively undifferentiated ovarian carcinomas (13) expressed increasing levels of Lin28, which is normally restricted to the ovarian surface epithelium where Misr2 is coexpressed. Misr2 inactivation correlated with up-regulation of Lin28 demonstrating that LIN28 contributes mechanistically, possibly via CDK inhibitors, to the differential regulation of the heterogeneous stem population of ovarian cancer cells.

One characteristic of human embryonic stem cells (hESCs) is the competence for self-renewal and pluripotency. It is possible that most human tumors are heterogeneous, with a rarer population of cancer stem cells which have properties of pluripotency. Recent studies have shown that it is possible to reprogram pluripotency in somatic cells by overexpression of key pluripotency factors. Four transcription factors, OCT3/4, SOX2, KLF4, and c-MYC, were found to be sufficient to induce pluripotency in adult (Takahashi et al, 2006) and human (Park et al, 2008) fibroblasts. LIN28 and LIN28B, which have been used to replace MYC in pluripotency induction protocols, are microRNA (miRNA) binding proteins which downregulate miRNA Let-7 (Viswanathan et al, 2009). Both LIN28 and LIN28b have found to be overexpressed in human ovarian cancer cell lines as compared to human normal ovarian surface epithelial cell lines (HOSE-4 and HOSE-6) indicating differential expression in malignant versus nonmalignant cells. Furthermore, since LIN28 is preferentially overexpressed in the 3+/Ecad− stem/progenitor cell enriched population of human ovarian cancer cells, LIN28 contributes to the resistance of the stem/progenitor population to therapeutics.

MIS is a member of the TGF superfamily, which regulates cell growth, differentiation, and apoptosis by binding to MISRII, which cross-phosphorylates the tissue-specific type I receptors (12) activin-like kinase 2 (ALK2) (22, 34) or ALK3 (35), which further signal by phosphorylating SMAD1/5/8 to activate downstream pathways notable for differentiation and growth inhibition (22, 36). Activation of phospho-SMAD1/5/8 by MIS, like bone morphogenetic proteins, is correlated with G1 arrest, inhibition of CDKs (37), and activation of cell cycle inhibitors (38, 39) in breast cancer cells, which we previously observed under the influence of MIS in OVCAR-8 (40) and in breast cancer cell lines (41). When treated with MIS or doxorubicin, the inventors demonstrated that p15 in both transgenic cell lines showed significant and opposite responses to MIS (FIG. 2G and FIG. 16) and doxorubicin (FIG. 2G), whereas the kinases tested were unaffected (data not shown).

Human embryonic stem cells (hESCs) have properties of self-renewal and pluripotency (Neganova et al, 2009) and show an atypical cell-cycle regulation as characterized by a high proliferation rate and a short G1 phase (Ruiz et al, 2011). When self-renewing normal stem cells are housed in a niche, however, they are conversely G1 arrested and slowly cycling; committed progenitors, in contrast, out of the confines of a niche, are rapidly cycling for effective expansion (Furukawa, 1998). MIS treatment resulted in G1 arrest in the 3+/Ecad− cells when compared to the 3+/Ecad− population; by contrast, doxorubicin increased the percentage in the 3−Ecad+ cells in G1. LIN28 via Let7 produces G1 arrest and induces P16 which we previously observed to be upregulated at the protein level by MIS in OVCAR-8 cells (Ha et al, 2000). Thus, MIS inhibits ovarian cancer cell growth by preventing cell cycle progression of the LIN28 enriched 3+/Ecad− population.

Self-renewing normal somatic stem cells are housed in a niche, where they are slowly cycling, as illustrated by label retention (20, 42); committed progenitors, when released from the confines of a niche, undergo rapid cycling for effective expansion (43). MIS treatment resulted in G1 accumulation in the 3+/Ecad− cells compared with the 3+/Ecad+ population; by contrast, doxorubicin decreased the percentage of the 3+/Ecad− cells in G1, demonstrating that the MIS may be exerting molecular effects similar to those extant in a normal niche. What is demonstrated herein by comparing the same population under doxorubicin stimulation and MIS inhibition in this experimental in vitro artificial niche allows critical molecular comparisons otherwise difficult to ascertain. Although it has long been suspected that cancer stem cells are resistant to chemotherapeutic agents (44, 45), herein the inventors demonstrate that these agents actively stimulate growth of chemotherapeutic naive ovarian cancer cells and indicates that these 3+/Ecad− ovarian cancer stem cells require specific targeting during design of all phases of therapeutic protocols. Multidrug resistance may therefore be considered constitutive rather than therapy induced. Diagnostic and treatment paradigms will need to be individualized to include pretesting of both stem cell-enriched and stem cell-depleted populations for sensitivity of each to chemotherapeutic agents and to biologics such as MIS. Such combinations, however, together can be expected to suppress more completely the entire tumor cell population (10). The 3+/Ecad− can be used in drug screens and other assays to identify additional characteristics of pluripotency and can be used in assays to identify novel drugs to target specifically this small, elusive, and insidious population. The response of this 3+/Ecad− population to inhibition by MIS or its small molecule mimetic SP600125 (5) will further support its pharmaceutical development as a therapeutic in the clinic, and it will be beneficial for treatment of ovarian cancers should be changed to include sensitivity testing of all of the heterogeneous populations when the diagnosis is made The aggregate results demonstrated herein indicate 1) that MIS, which is thought to suppress excess proliferation of the surface epithelium of the normal ovary after ovulation (Szotek et al, 2008), can also act as a potent tumor suppressor of ovarian cancer initiation (Teixeira et al,); 2) that MIS can target, as a receptor mediated event (Masiakos et al, 1999), the stem/progenitor population of the ovarian cancer cell line; 3) that MIS can functionally phosphorylate SMAD 1/5/8, which leads to a cascade of downstream events that result in G1 arrest to suppress tumor growth of this population in vitro and in vivo.

In the future, diagnostic and treatment paradigms will need to be individualized to include separate pretesting of stem/progenitor cell enriched and non stem cell enriched populations for sensitivity of each to chemotherapeutic agents and biologics such as MIS. Analysis of the transgenic animal models with progressive loss of Misr2 provides additional strong evidence that MIS is a tumor suppressor that should be developed as a therapeutic for human ovarian cancer, to be used in combination with chemotherapeutic agents or with other agents that prove to be synergistic with MIS. Such combinations will suppress the entire tumor population, while MIS subsequently can be used alone, to prevent the recurrence attributable to the stem/progenitor population. LIN28, a pluripotency factor, is also enriched in this population, providing both another marker and a therapeutic target for this evasive yet controlling cellular species.

Using the discovery herein, multidrug resistance is likely to predominantly constitutive as pluripotency factors play an important role in stem cell-mediated drug resistance since the 3+/Ecad− population that responded poorly to chemotherapeutic agents responded well to MIS and its small molecule mimetic SP600125 (Wei et al, 2010). By determining if a subject or patient has a 3+/Ecad− population of ovarian cancer stem cells in a sample, e.g., in primary ascites, it would be highly useful for determining the manner in which ovarian cancers are treated, and can also include sensitivity testing of all of the heterogeneous populations of ovarian cancers when the diagnosis is made. This 3+/Ecad− population chemotherapeutic drug resistant population with seminal characteristics of pluripotency is highly likely to be responsible for recurrence and metastases in subject and can also be used to as a ovarian cancer stem cell population in an assays to discover novel drugs to target specifically this small, elusive, and insidious population. Additionally, the consistent response of this 3+/Ecad− population to MIS makes it an essential target for treating ovarian cancer in subjects, as well as in diagnosis and prognostic methods to identify ovarian cancer in a subject.

REFERENCES

The references in the specification and Examples section are incorporated herein in their entirety by reference.

Zhan Y, et al., Müllerian inhibiting substance regulates its receptor/SMAD signaling and causes mesenchymal transition of the coelomic epithelial cells early in Müllerian duct regression. Development. 2006 June; 133(12):2359-69.

Furukawa Y. Cell cycle regulation of hematopoietic stem cells. Hum Cell. 1998 June; 11(2):81-92.

Ruiz S, et al. A high proliferation rate is required for cell reprogramming and maintenance of human embryonic stem cell identity. Curr Biol. 2011 Jan. 11; 21(1):45-52.

1. Al-Hajj M, Wicha M S, Benito-Hernandez A, Morrison S J, Clarke M F (2003) Prospective identification of tumorigenic breast cancer cells. Proc Natl Acad Sci USA 100:3983-3988.
2. Bapat S A, Mali A M, Koppikar C B, Kurrey N K (2005) Stem and progenitor-like cells contribute to the aggressive behavior of human epithelial ovarian cancer. Cancer Res 65:3025-3029.
3. Reya T, Morrison S J, Clarke M F, Weissman I L (2001) Stem cells, cancer, and cancer stem cells. Nature 414 (6859):105-111.
4. Szotek P P, et al. (2006) Ovarian cancer side population defines cells with stem cell-like characteristics and Mullerian Inhibiting Substance responsiveness. Proc Natl Acad Sci USA 103:11154-11159.
5. Wei X, et al. (2010) Mullerian inhibiting substance preferentially inhibits stem/progenitors in human ovarian cancer cell lines compared with chemotherapeutics. Proc Natl Acad Sci USA 107:18874-18879.
6. Josso N (1973) In vitro synthesis of Müllerian-inhibiting hormone by seminiferous tubules isolated from the calf fetal testis. Endocrinology 93:829-834.
7. Scully R E (1977) Ovarian tumors. A review. Am J Pathol 87:686-720.
8. Song J Y, et al. (2009) The expression of Müllerian inhibiting substance/anti-Müllerian hormone type II receptor protein and mRNA in benign, borderline and malignant ovarian neoplasia. Int J Oncol 34:1583-1591.
9. Masiakos P T, et al. (1999) Human ovarian cancer, cell lines, and primary ascites cells express the human Mullerian inhibiting substance (MIS) type II receptor, bind, and are responsive to MIS. Clin Cancer Res 5:3488-3499.
10. Pieretti-Vanmarcke R, et al. (2006) Mullerian Inhibiting Substance enhances subclinical doses of chemotherapeutic agents to inhibit human and mouse ovarian cancer. Proc Natl Acad Sci USA 103:17426-17431.
11. Auersperg N, et al. (1999) E-cadherin induces mesenchymal-to-epithelial transition in human ovarian surface epithelium. Proc Natl Acad Sci USA 96:6249-6254.
12. Zhan Y, et al. (2006) Müllerian inhibiting substance regulates its receptor/SMAD signaling and causes mesenchymal transition of the coelomic epithelial cells early in Müllerian duct regression. Development 133:2359-2369.
13. Tanwar P S, et al. (2009) Constitutive activation of beta-catenin in uterine stroma and smooth muscle leads to the development of mesenchymal tumors in mice. Biol Reprod 81:545-552.
14. Kalluri R, Weinberg R A (2009) The basics of epithelial-mesenchymal transition. J Clin Invest 119:1420-1428.
15. Onder T T, et al. (2008) Loss of E-cadherin promotes metastasis via multiple downstream transcriptional pathways. Cancer Res 68:3645-3654.
16. Uchikado Y, et al. (2005) Slug expression in the E-cadherin preserved tumors is related to prognosis in patients with esophageal squamous cell carcinoma. Clin Cancer Res 11: 1174-1180.
17. Heo I, et al. (2008) Lin28 mediates the terminal uridylation of let-7 precursor micro-RNA. Mol Cell 32:276-284.
18. Viswanathan S R, Daley G Q (2010) Lin28: A microRNA regulator with a macro role. Cell 140:445-449.
19. Che M, et al. (2001) Ovarian mixed-epithelial carcinomas with a microcystic pattern and signet-ring cells. Int J Gynecol Pathol 20:323-328.
20. Szotek P P, et al. (2008) Normal ovarian surface epithelial label-retaining cells exhibit stem/progenitor cell characteristics. Proc Natl Acad Sci USA 105:12469-12473.
21. Bandera C A, Tsui H W, Mok S C, Tsui F W (2003) Expression of cytokines and receptors in normal, immortalized, and malignant ovarian epithelial cell lines. Anticancer Res 23: 3151-3157.
22. Clarke T R, et al. (2001) Müllerian inhibiting substance signaling uses a bone morphogenetic protein (BMP)-like pathway mediated by ALK2 and induces SMAD6 expression. Mol Endocrinol 15:946-959.
23. Takahashi K, Yamanaka S (2006) Induction of pluripotent stem cells from mouse embryonic and adult fibroblast cultures by defined factors. Cell 126:663-676.
24. Yu J, et al. (2007) Induced pluripotent stem cell lines derived from human somatic cells. Science 318:1917-1920.
25. Park I H, Lerou P H, Zhao R, Huo H, Daley G Q (2008) Generation of human-induced pluripotent stem cells. Nat Protoc 3:1180-1186.

26. Tanwar P S, et al. (2010) Focal Mullerian duct retention in male mice with constitutively activated beta-catenin expression in the Mullerian duct mesenchyme. Proc Natl Acad Sci USA 107:16142-16147.
27. Matulonis U A, et al. (2008) Phase II study of carboplatin and pemetrexed for the treatment of platinum-sensitive recurrent ovarian cancer. J Clin Oncol 26:5761-5766.
28. Morgan R J, Jr., et al.; National Comprehensive Cancer Network (2008) Ovarian cancer. Clinical practice guidelines in oncology. J Natl Compr Canc Netw 6:766-794.
29. Curley M D, et al. (2009) CD133 expression defines a tumor initiating cell population in primary human ovarian cancer. Stem Cells 27:2875-2883.
30. Landen C N, Jr., et al. (2010) Targeting aldehyde dehydrogenase cancer stem cells in ovarian cancer. Mol Cancer Ther 9:3186-3199.
31. Sharma S V, et al. (2010) A chromatin-mediated reversible drug-tolerant state in cancer cell subpopulations. Cell 141(1):69-80.
32. Büssing I, Slack F J, Grosshans H (2008) let-7 microRNAs in development, stem cells and cancer. Trends Mol Med 14:400-409.
33. Krogan N J, et al. (2004) High-definition macromolecular composition of yeast RNA processing complexes. Mol Cell 13:225-239.
34. Visser J A, et al. (2001) The serine/threonine transmembrane receptor ALK2 mediates Müllerian inhibiting substance signaling. Mol Endocrinol 15:936-945.
35. Jamin S P, Arango N A, Mishina Y, Hanks M C, Behringer R R (2002) Requirement of Bmpr1a for Müllerian duct regression during male sexual development. Nat Genet 32: 408-410.
36. Massagué J, Wotton D (2000) Transcriptional control by the TGF-beta/Smad signaling system. EMBO J 19:1745-1754.
37. Alarcón C, et al. (2009) Nuclear CDKs drive Smad transcriptional activation and turnover in BMP and TGF-beta pathways. Cell 139:757-769.
38. Hannon G J, Beach D (1994) p15INK4B is a potential effector of TGF-beta-induced cell cycle arrest. Nature 371:257-261.
39. Reynisdóttir I, Polyak K, Iavarone A, Massagué J (1995) Kip/Cip and Ink4 Cdk inhibitors cooperate to induce cell cycle arrest in response to TGF-beta. Genes Dev 9:1831-1845.
40. Ha T U, et al. (2000) Mullerian inhibiting substance inhibits ovarian cell growth through an Rb-independent mechanism. J Biol Chem 275:37101-37109.
41. Segev D L, et al. (2000) Mullerian inhibiting substance inhibits breast cancer cell growth through an NFkappa B-mediated pathway. J Biol Chem 275:28371-28379.
42. Kobielak K, Stokes N, de la Cruz J, Polak L, Fuchs E (2007) Loss of a quiescent niche but not follicle stem cells in the absence of bone morphogenetic protein signaling. Proc Natl Acad Sci USA 104:10063-10068.
43. Jung P, et al. (2011) Isolation and in vitro expansion of human colonic stem cells. Nat Med 17:1225-1227.
44. Gupta P B, et al. (2009) Identification of selective inhibitors of cancer stem cells by high-throughput screening. Cell 138:645-659.
45. Zhang S, et al. (2008) Identification and characterization of ovarian cancer-initiating cells from primary human tumors. Cancer Res 68:4311-4320.
46. Lau K M, Mok S C, Ho S M (1999) Expression of human estrogen receptor-alpha and -beta, progesterone receptor, and androgen receptor mRNA in normal and malignant ovarian epithelial cells. Proc Natl Acad Sci USA 96:5722-5727.
47. Johnson S W, Laub P B, Beesley J S, Ozols R F, Hamilton T C (1997) Increased platinum-DNA damage tolerance is associated with cisplatin resistance and cross-resistance to various chemotherapeutic agents in unrelated human ovarian cancer cell lines. Cancer Res 57:850-856.
48. Connolly D C, et al. (2003) Female mice chimeric for expression of the simian virus 40 TAg under control of the MISIIR promoter develop epithelial ovarian cancer. Cancer Res 63:1389-1397.
49. Hamilton T C, et al. (1983) Characterization of a human ovarian carcinoma cell line (NIH:OVCAR-3) with androgen and estrogen receptors. Cancer Res 43:5379-5389.
50. Fogh J, Wright W C, Loveless J D (1977) Absence of HeLa cell contamination in 169 cell lines derived from human tumors. J Natl Cancer Inst 58:209-214.
51. Bénard J, et al. (1985) Characterization of a human ovarian adenocarcinoma line, IGROV1, in tissue culture and in nude mice. Cancer Res 45:4970-4979.
52. Ragin R C, Donahoe P K, Kenneally M K, Ahmad M F, MacLaughlin D T (1992) Human Müllerian inhibiting substance: Enhanced purification imparts biochemical stability and restores antiproliferative effects. Protein Expr Purif 3:236-245.
53. Donahoe P K, Ito Y, Price J M, Hendren, W H, III (1977) Müllerian inhibiting substance activity in bovine fetal, newborn and prepubertal testes. Biol Reprod 16:238-243.
54. Preffer F, Dombkowski D (2009) Advances in complex multiparameter flow cytometry technology: Applications in stem cell research. Cytometry B Clin Cytom 76:295-314.

The invention claimed is:

1. A method to detect the presence of ovarian cancer stem cells in a population of ovarian cancer cells, the method comprising;
    (a) contacting the population of ovarian cancer cells with an anti-CD24 antibody, an anti-CD44 antibody, an anti-EpCam antibody and an anti-E-Cadherin antibody; and
    (b) detecting whether an ovarian cancer cell is positive for the expression of CD24, CD44, EpCam and negative for the expression of E-Cadherin by detecting positive binding between; CD24 and the anti-CD24 antibody, CD44 and the anti-CD44 antibody, EpCam and the anti-EpCam antibody and detecting negative binding between E-Cadherin and the anti-E-Cadherin antibody, wherein the detected ovarian cancer stem cells that are positive for the expression of CD24, CD44, EpCam and negative for the expression of E-Cadherin are responsive to inhibition of proliferation by MIS.

2. The method of claim 1, wherein the ovarian cancer stem cells are resistant to chemotherapeutic agents.

3. The method of claim 2, wherein the chemotherapeutic agent is selected from the group consisting of: dexorubicin, taxol, cisplatin, paclitaxel and derivatives thereof.

4. The method of claim 1, wherein the population of ovarian cancer cells is present in a biological sample, wherein the biological sample comprises any of the group consisting of: ovarian cells, ascites, ovarian cell line, ovarian cancer biopsy sample.

5. A method of diagnosing and treating a subject with ovarian cancer comprising ovarian cancer stem cells, the method comprising:
    (a) contacting a population of ovarian cancer cells obtained from the subject with an anti-CD24 antibody, an anti-CD44 antibody, an anti-EpCam antibody and an anti-E-Cadherin antibody; and
    (b) detecting whether an ovarian cancer stem cell is present in the population of ovarian cancer cells, by detecting whether an ovarian cancer cell is positive for the expression of CD24, CD44, EpCam and negative for the expression of E-Cadherin by detecting positive binding between; CD24 and the anti-CD24 antibody, CD44 and the anti-CD44 antibody, EpCam and the anti-EpCam antibody and detecting negative binding between E-Cadherin and the anti-E-Cadherin antibody;
    (c) diagnosing the subject with ovarian cancer comprising ovarian cancer stem cells when an ovarian cancer cell positive for the expression of CD24, CD44, EpCam and negative for the expression of E-Cadherin is detected; and
    (d) administering a pharmaceutically effective amount of MIS or a MIS mimetic to the diagnosed subject.

6. The method of claim 5, wherein the MIS is recombinant human MIS (rhMIS) polypeptide or a pro-hormone or homodimer thereof.

* * * * *